(12) United States Patent
Wang et al.

(10) Patent No.: US 10,676,500 B2
(45) Date of Patent: Jun. 9, 2020

(54) PROCESS FOR PREPARATION OF SULFONYL CARBAMATE BILE ACID DERIVATIVES

(71) Applicant: Enanta Pharmaceuticals, Inc., Watertown, MA (US)

(72) Inventors: Guoqiang Wang, Belmont, MA (US); Yong He, Lexington, MA (US); Brett Granger, Sudbury, MA (US); Xuechao Xing, Wilmington, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 15/948,370

(22) Filed: Apr. 9, 2018

(65) Prior Publication Data
US 2018/0291058 A1    Oct. 11, 2018

Related U.S. Application Data

(60) Provisional application No. 62/483,044, filed on Apr. 7, 2017.

(51) Int. Cl.
*C07J 41/00* (2006.01)
*C07J 43/00* (2006.01)
(Continued)

(52) U.S. Cl.
CPC ......... *C07J 41/005* (2013.01); *C07J 41/0055* (2013.01); *C07J 43/003* (2013.01); *C07J 9/005* (2013.01); *C07J 51/00* (2013.01)

(58) Field of Classification Search
CPC ........ C07J 41/005; C07J 9/005; C07J 43/003; C07J 41/0055; C07J 51/00
See application file for complete search history.

(56) References Cited

U.S. PATENT DOCUMENTS

| | | |
|---|---|---|
| 4,202,876 A | 5/1980 | Monks et al. |
| 5,466,815 A | 11/1995 | Enhsen et al. |

(Continued)

FOREIGN PATENT DOCUMENTS

| | | |
|---|---|---|
| CN | 105175473 A | 12/2015 |
| CN | 106478759 A | 3/2017 |

(Continued)

OTHER PUBLICATIONS

Zaragoza Dorwald, Side Reactions in Organic Synthesis, 2005, WILEY-VCH Verlag GmbH & Co. KGaA, Weinheim, Preface. p. IX. (Year: 2005).*

(Continued)

*Primary Examiner* — Paul A Zucker
(74) *Attorney, Agent, or Firm* — Edgar W. Harlan; Carolyn S. Elmore; Elmore Patent Law Group, P.C.

(57) ABSTRACT

The present invention relates to processes for preparing compounds of Formula (I) and compounds of Formula (II):

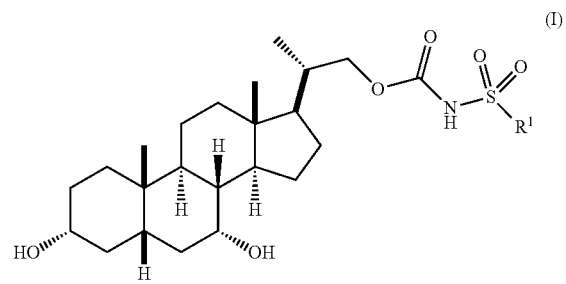

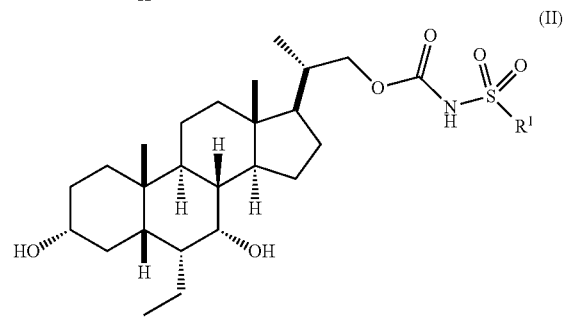

These compounds are useful as FXR or TGR5 modulators. The present invention also relates to processes for the preparation of the compounds of Formula (III), Formula (IV), Formula (V), and Formula (VI),

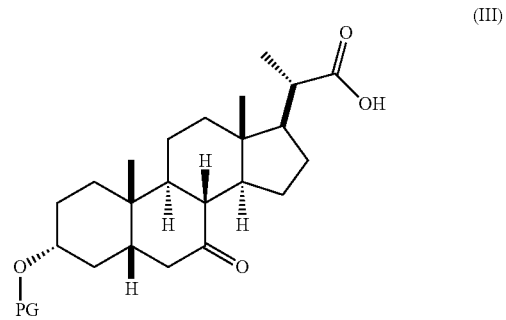

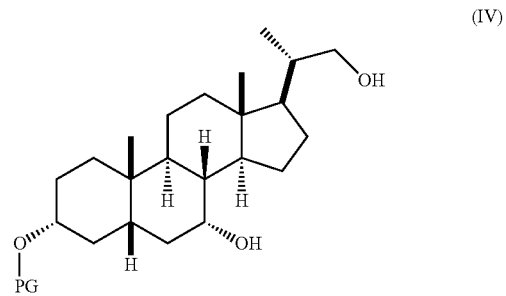

(Continued)

-continued

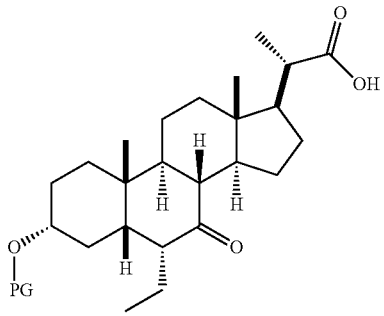

(V)

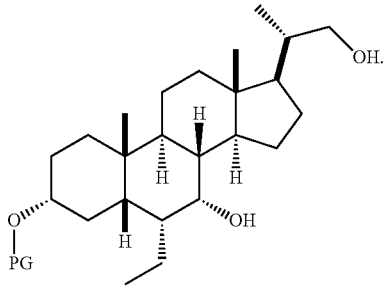

(VI)

The present invention also relates to a process for the preparation of compounds (VII), (VIII) and (IX),

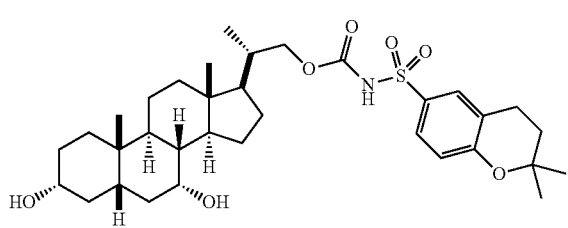

(VII)

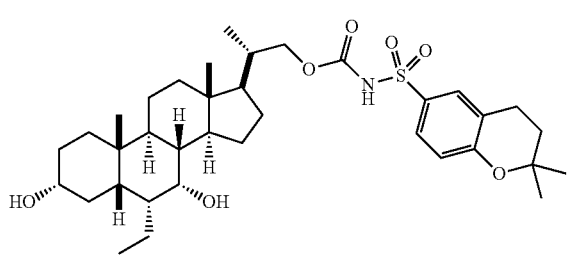

(VIII)

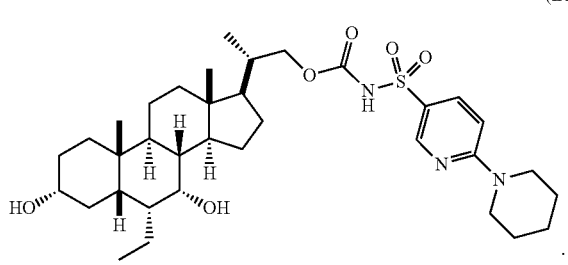

(IX)

8 Claims, No Drawings

(51) Int. Cl.
C07J 51/00 (2006.01)
C07J 9/00 (2006.01)

(56) References Cited

U.S. PATENT DOCUMENTS

| 5,512,558 | A | 4/1996 | Enhsen et al. |
| 5,646,316 | A | 7/1997 | Jacobson et al. |
| 5,656,277 | A | 8/1997 | Berlati et al. |
| 7,858,608 | B2 * | 12/2010 | Pellicciari ............... C07J 41/00 514/182 |
| 2005/0054559 | A1 | 3/2005 | Gallop et al. |
| 2007/0142340 | A1 | 6/2007 | Pellicciari |
| 2008/0039435 | A1 | 2/2008 | Pellicciari |
| 2008/0182832 | A1 | 7/2008 | Pellicciari et al. |
| 2008/0214515 | A1 | 9/2008 | Ferrari et al. |
| 2009/0062526 | A1 | 3/2009 | Yu et al. |
| 2009/0163474 | A1 | 6/2009 | Zhang et al. |
| 2010/0063018 | A1 | 3/2010 | Pellicciari et al. |
| 2010/0324004 | A1 | 12/2010 | McLane et al. |
| 2011/0172198 | A1 | 7/2011 | Pellicciari |
| 2013/0116218 | A1 | 5/2013 | Kaplan et al. |
| 2013/0345188 | A1 | 12/2013 | Steiner et al. |
| 2014/0057886 | A1 | 2/2014 | Pellicciari et al. |
| 2014/0186438 | A1 | 7/2014 | Manku et al. |
| 2014/0187633 | A1 | 7/2014 | Manku et al. |
| 2014/0206657 | A1 | 7/2014 | Yu et al. |
| 2014/0371190 | A1 | 12/2014 | Pellicciari et al. |
| 2015/0112089 | A1 | 4/2015 | Finch et al. |
| 2016/0130297 | A1 | 5/2016 | Or et al. |
| 2016/0145295 | A1 | 5/2016 | Or et al. |
| 2016/0145296 | A1 | 5/2016 | Wang et al. |
| 2016/0176917 | A1 | 6/2016 | Wang et al. |
| 2016/0185815 | A1 | 6/2016 | Wang et al. |
| 2016/0229886 | A1 | 8/2016 | Shen et al. |
| 2016/0289262 | A1 | 10/2016 | Wang et al. |
| 2017/0101434 | A1 | 4/2017 | Pellicciari et al. |
| 2017/0240585 | A1 | 8/2017 | Wang et al. |
| 2017/0240586 | A1 | 8/2017 | Or et al. |
| 2017/0240587 | A1 | 8/2017 | Or et al. |
| 2017/0260225 | A1 | 9/2017 | Pellicciari et al. |
| 2018/0148469 | A1 | 5/2018 | Wang et al. |
| 2018/0148470 | A1 | 5/2018 | Li et al. |
| 2018/0237471 | A1 | 8/2018 | Wang et al. |
| 2018/0291058 | A1 | 10/2018 | Wang et al. |

FOREIGN PATENT DOCUMENTS

| CN | 106518946 A | 3/2017 |
| EP | 583566 A2 | 2/1994 |
| EP | 1364645 A1 | 11/2003 |
| EP | 1947108 A1 | 7/2008 |
| EP | 3290429 A1 | 3/2018 |
| JP | H1160594 A | 3/1999 |
| JP | H11109628 A | 4/1999 |
| WO | 198702367 A2 | 4/1987 |
| WO | 0037077 A1 | 6/2000 |
| WO | 0228881 A1 | 4/2002 |
| WO | 2003030612 A2 | 4/2003 |
| WO | 03086303 A2 | 10/2003 |
| WO | 2005089316 A2 | 9/2005 |
| WO | 2007089907 A2 | 8/2007 |
| WO | 2007095174 A2 | 8/2007 |
| WO | 2007111994 A2 | 10/2007 |
| WO | 2008009407 A2 | 1/2008 |
| WO | 2008091540 A2 | 7/2008 |
| WO | 2010014836 A3 | 2/2010 |
| WO | 2011020615 A1 | 2/2011 |
| WO | 2013007387 A1 | 1/2013 |
| WO | 2013020108 A2 | 2/2013 |
| WO | 2013166176 A1 | 11/2013 |
| WO | 2013192097 A1 | 12/2013 |
| WO | 2014036379 A2 | 3/2014 |
| WO | 2014184271 A1 | 11/2014 |
| WO | 2015017813 A2 | 2/2015 |
| WO | 2015181275 A1 | 12/2015 |

(56) References Cited

FOREIGN PATENT DOCUMENTS

| WO | 2016173493 A2 | 11/2016 |
|---|---|---|
| WO | 2016173524 A1 | 11/2016 |
| WO | 2016205475 A | 12/2016 |
| WO | 2017027396 A1 | 2/2017 |
| WO | 2017053826 A1 | 3/2017 |
| WO | 2017129125 A1 | 8/2017 |

OTHER PUBLICATIONS

U.S. Appl. No. 16/222,380, filed Dec. 17, 2018.
Macchiarulo, A. et al., "Charting the chemical space of target sites: insights into the binding modes of amine and amidine groups", Journal of chemical information and modeling, 49(4), Mar. 18, 2009, 900-912.
Okada, J, "Preparation of bile acid derivatives and their use as nasal absorption enhancers", Database CA [Online] Chemical Abstracts Service, Columbus, Ohio, US; retrieved from STN Database accession No. 1999:142390.
Roda, A. et al., "Effect of Basic Cholane Derivatives on Intestinal Cholic Acid Metabolism: In Vitro and in Vivo Activity", Journal of Pharmaceutical Sciences, vol. 81, No. 3, 1992, 237-240.
Okahata, "Base-catalyzed proton abstraction from.beta.-(p-nitrophenoxy) propiophenone in the presence of Single-chain, double-chain, and triple-chain ammonium bilayer membrane aggregates", The Chemical Society of Japan, vol. 3, Mar. 10, 1980, 442-449.
Macchiarulo, et al., "Probing the Binding Site of Bile Acids in TGR5," Medicinal Chemistry Letters, 4 (12):1158-1162, 2013.
Sato, et al., "Novel Potent and Selective Bile Acid Derivatives as TGR5 Agonists: Biological Screening, Structure—Activity Relationships, and Molecular Modeling Studies," J. Med. Chem., 51:1831-1841, 2008.
Mosesin-4' at www.chemspider.com/ Chemical-Structure.10375019.html (retrieved from the internet Oct. 11, 2016).
Pellicciari, et al., "6α-Ethyl-Chenodeoxycholic Acid (6-ECDCA), a Potent and Selective FXR Agonist Endowed with Anticholestatic Activity," Journal of Medicinal Chemistry, 45(17):3569-3572, 2002.
Silverman, "Prodrugs and Drug Delivery Systems," The Organic Chemistry of Drug Design and Drug Action, pp. 352-399, 1992.
Banker, et al., Modern Pharmaceutics, 3rd edition, 1996.
Bundgaard, "Design of Prodrugs: Bioreversible derivatives for various functional groups and chemical entities," Design of Prodrugs, Chapter 1, 1985.
Wolff, Burger's Medicinal Chemistry and Drug Discovery, 5(1):975-977, 1995.
Kim, et al., "Synthesis and Antimicrobial Activity of New 3α-Hydroxy-23,24-bisnorcholane Polyamine Carbamates," Bioorganic & Medicinal Chemistry Letters, 11:3065-3068, 2001.
Solaja, et al., "Novel 4-Aminoquinolines Active against Chloroquine-Resistant and Sensitive P. falciparum Strains that also Inhibit Botulinum Serotype A," J. Med. Chem., 51:4388-4391, 2008.
Willemen, et al., "Alkyl Derivatives of Cholic Acid as Organogelators: One-Component and Two-Component Gels," Langmuir, 18(19):7102-7106, 2002.
Pore, et al., "Design and synthesis of fluconazole/bile acid conjugate using click reaction", Tetrahedron, 62:11178-11186, 2006.
Nikolaienko, et al., "Rapid way to fluorescent cholic-based chemosensor precursors", Synthetic Organic Chemistry, pp. 1-4, 2011.
Sepe, et al., "Farnesoid X receptor modulators (2011-2014): a patent review," Expert Opinion on Therapeutic Patents, 25:8, 885-896, 2015.
Crawley, "Farnesoid X Receptor Modulators: a patent review," Expert Opinion on Therapeutic Patents, 20(8):1047-1057, 2010.
Briere, et al., "Novel small molecule agonist of TGR5 possesses anti-diabetic effects but causes gallbladder filling in mice." PLOS one, 10(8):1-17, 2015.
Okahata, et al., "Catalytic Hydrolysis of p-Nitrophenyl Esters in the Presence of Representative Ammonium Aggregates. Specific Activation of a Cholesteryl Nucleophile Bound to a Dialkylammonium Bilayer Membrane." Bulletin of hte Chemical Society of Japan, 52(12):3647-3653, 1979.
Sajisha, et al., "Remarkable isomer-selective gelation of aromatic solvents by a polymorph of a urea-linked bile acid-amino acid conjugate," RSC Advances, 4(81):43167-43171, 2014. Abstract only.
Mayorquin-Torres, et al., "Application of palladium-catalyzed carboxyl anhydride-boronic acid cross coupling in the synthesis of novel bile acids analogs with modified side chains". Steroids, (101):21-27, 2015.
Ali, et al., "Recent advances in the development of farnesoid X receptor agonists," Ann Transl Med, 3(1):5, pp. 1-16, 2015.
PUBCHEM-CID-122592927, Created Date: Dec. 8, 2016.
PUBCHEM-CID-122592945, Created Date: Dec. 8, 2016.
Pellicciari, R., et al., "Bile Acid Derivatives as Ligands of the Farnesoid X Receptor. Synthesis, Evaluation, and Structure—Activity Relationship of a Series of Body and Side Chain Modified Analogues of Chenodeoxycholic Acid", Journal of Medicinal Chemistry, American Chemical Society, 47:4559-4569, 2004.
Okahata, Y., et al., "Base-catalyzed proton abstraction from .beta.-(p-nitrophenoxy)propiophenone in the presence of single-chain, double-chain, and triple-chain ammonium bilayer membrane aggregates", Database CA [Online] Chemical Abstracts Service, Database accession No. 1980:549272, abstract, 1980.
Pellicciari, et al. "Back Door Modulation of the Farnesoid X Receptor: Design, Synthesis and Biological Evaluation of a Series of Side Chain Modified Chenodeoxycholic Acid Derivatives", Journal of Medicinal Chemi, American Chemical Society, 49:4208-4215, 2006.
Gioiello Antimo, et al., "Extending SAR of bile acids as FXR ligands: discovery of 23-N-(carbocinnamyloxy)-3 [alpha],7[alpha]dihydroxy-6[alpha]-ethyl-24-nor-5[beta]-cholan-23-amine", Bioorganic & Medicinal Chemistry, 19(8):2650-2658, 2011.
Griffiths, et al., "Charge-remote fragmentation of bile acids derivatized with amino-sulphonic acids," Rapid Communication in Mass Spectrometry, 7(3):235-240, 1993.
Coleman, J. P., et al., "Metabolic Fate and Hepatocyte Toxicity of Reverse Amide Analogs of Conjugated Ursodeoxycholate in the Rat," J. Steroid Biochem. Molec. Biol., 64(1/2): 91-101, 1998.
Opsenica, I. M., et al., "4-Amino-7-chloroquinolines: Probing Ligand Efficiency Provides Botulinum Neurotoxin Serotype A Light Chain Inhibitors with Significant Antiprotozoal Activity," J. Med. Chem., (56):5860-5871, 2013.
Fini, A., et al."Basic Cholane Derivatives. XI: Comparison between Acid and Basic Derivatives," Journal of Pharmaceutical Sciences, (81)7:726-730, 1992.
Fini, A., et al., "Quantitative Structure-Antimicrobial Activity Relationship in 5B-Cholanyl-24-benzylamine Derivatives," Journal of Pharmaceutical Sciences, (79)7:603-605, 1990.
Ballatore, C., et al., "Carboxylic Acid (Bio)Isosteres in Drug Design," ChemMedChem., (8)3: 385-395, 2013.
Honorio, K. M., et al., "Hologram QSAR Studies on Farnesoid X Receptor Activators," Letters in Drug Design & Discovery, (3):261-267, 2006.
Meijide, F. et al., "Spontaneous Formation in the Solid State of Carbamate Derivatives of Bile Acids", Crystal Growth and Design, 11(1), 2011, 356-361.
Videnovic, M. et al., "Second Generation Steroidal 4-Aminoquinolines Are Potent, Dual-Target Inhibitors . . . ", J. Med. Chem., 57(10), Apr. 17, 2014, 4134-4153.

* cited by examiner

PROCESS FOR PREPARATION OF SULFONYL CARBAMATE BILE ACID DERIVATIVES

RELATED APPLICATIONS

This application claims the benefit of U.S. Provisional Application No. 62/483,044, filed on Apr. 7, 2017. The entire teachings of the above application are incorporated herein by reference.

TECHNICAL FIELD

The present invention relates to processes and intermediates useful in the preparation of biologically active molecules useful as FXR or TGR5 modulators, especially relates to bile acid derivatives and methods for their preparation and use.

BACKGROUND OF THE INVENTION

Farnesoid X Receptor (FXR) is an orphan nuclear receptor initially identified from a rat liver cDNA library (BM. Forman, et al., *Cell*, 1995, 81(5), 687-693) that is most closely related to the insect ecdysone receptor. FXR is a member of the nuclear receptor family of ligand-activated transcription factors that includes receptors for the steroid, retinoid, and thyroid hormones (DJ. Mangelsdorf, et al., *Cell*, 1995, 83(6), 841-850). The relevant physiological ligands of FXR are bile acids (D. Parks et al., *Science*, 1999, 284(5418), 1362-1365). The most potent one is chenodeoxycholic acid (CDCA), which regulates the expression of several genes that participate in bile acid homeostasis. Farnesol and derivatives, together called farnesoids, are originally described to activate the rat orthologue at high concentration but they do not activate the human or mouse receptor. FXR is expressed in the liver, throughout the entire gastrointestinal tract including the esophagus, stomach, duodenum, small intestine, colon, ovary, adrenal gland and kidney. Beyond controlling intracellular gene expression, FXR seems to be also involved in paracrine and endocrine signaling by upregulating the expression of the cytokine Fibroblast Growth Factor (J. Holt et al., *Genes Dev.*, 2003, 17(13), 1581-1591; T. Inagaki et al., *Cell Metab.*, 2005, 2(4), 217-225).

Small molecule compounds which act as FXR modulators have been disclosed in the following publications: WO 2000/037077, WO 2002/072598, WO 2003/015771, WO 2003/099821, WO 2004/00752, WO 2004/048349, WO 2005/009387, WO 2005/082925, US 2005/0054634, WO 2007/052843, WO 2007/070796, WO 2007/076260, WO 2007/092751, WO 2007/095174, WO 2007/140174, WO 2007/140183, US 2007/0142340, WO 2008/000643, WO 2008/002573, WO 2008/025539, WO 2008/025540, WO 2008/051942, WO 2008/073825, WO 2008/157270, US 2008/0299118, US 2008/0300235, WO 2009/005998, WO 2009/012125, WO 2009/027264, WO 2009/062874, WO 2009/127321, WO 2009/149795, US 2009/0131409, US 2009/0137554, US 2009/0163474, US 2009/0163552, US 2009/0215748, WO 2010/043513, WO 2011/020615, WO 2011/117163, WO 2012/087519, WO 2012/087520, WO 2012/087521, WO 2013/007387, WO 2013/037482, WO 2013/166176, WO 2013/192097, WO 2014/184271, US 2014/0186438, US 2014/0187633, WO 2015/017813, WO 2015/069666, WO 2016/073767, WO 2016/116054, WO 2016/103037, WO 2016/096116, WO 2016/096115, WO 2016/097933, WO 2016/081918, WO 2016/127924, WO 2016/130809, WO 2016/145295, WO 2016/173524, CN 106632294, CN 106588804, US 2017/0196893, WO 2017/062763, WO 2017/053826, CN 106518708, CN 106518946, CN 106478759, CN 106478447, CN 106478453, WO 2017/027396, WO 2017/049172, WO 2017/049173, WO 2017/049176, WO 2017/049177, WO 2017/118294, WO 2017/128896, WO 2017/129125, WO 2017/133521, WO 2017/147074, WO 2017/147174, WO 2017/145041, and WO 2017/156024 A1.

Further small molecule FXR modulators have been recently reviewed (R. C. Buijsman et al. *Curr. Med. Chem.* 2005, 12, 1017-1075).

TGR5 receptor is a G-protein-coupled receptor that has been identified as a cell-surface receptor that is responsive to bile acids (BAs). The primary structure of TGR5 and its responsiveness to bile acids has been found to be highly conserved in TGR5 among human, bovine, rabbit, rat, and mouse, and thus suggests that TGR5 has important physiological functions. TGR5 has been found to be widely distributed in not only lymphoid tissues but also in other tissues. High levels of TGR5 mRNA have been detected in placenta, spleen, and monocytes/macrophages. Bile acids have been shown to induce internalization of the TGR5 fusion protein from the cell membrane to the cytoplasm (Kawamata et al., *J. Bio. Chem.*, 2003, 278, 9435). TGR5 has been found to be identical to hGPCR19 reported by Takeda et al., *FEBS Lett.* 2002, 520, 97-101.

TGR5 is associated with the intracellular accumulation of cAMP, which is widely expressed in diverse cell types. While the activation of this membrane receptor in macrophages decreases pro-inflammatory cytokine production, (Kawamata, Y., et al., *J. Biol. Chem.* 2003, 278, 9435-9440) the stimulation of TGR5 by BAs in adipocytes and myocytes enhances energy expenditure (Watanabe, M., et al. *Nature.* 2006, 439, 484-489). This latter effect involves the cAMP-dependent induction of type 2 iodothyronine deiodinase (D2), which by, locally converting T4 into T3, gives rise to increased thyroid hormone activity. Consistent with the role of TGR5 in the control of energy metabolism, female TGR5 knock-out mice show a significant fat accumulation with body weight gain when challenged with a high fat diet, indicating that the lack of TGR5 decreases energy expenditure and elicits obesity (Maruyama, T., et al., *J. Endocrinol.* 2006, 191, 197-205). In addition and in line with the involvement of TGR5 in energy homeostasis, bile acid activation of the membrane receptor has also been reported to promote the production of glucagon-like peptide 1 (GLP-1) in murine enteroendocrine cell lines (Katsuma, S., *Biochem. Biophys. Res. Commun.*, 2005, 329, 386-390). On the basis of all the above observations, TGR5 is an attractive target for the treatment of disease e.g., obesity, diabetes and metabolic syndrome.

In addition to the use of TGR5 agonists for the treatment and prevention of metabolic diseases, compounds that modulate TGR5 modulators are also useful for the treatment of other diseases e.g., central nervous diseases as well as inflammatory diseases (WO 01/77325 and WO 02/84286). Modulators of TGR5 also provide methods of regulating bile acid and cholesterol homeostasis, fatty acid absorption, and protein and carbohydrate digestion.

There is a need for the development of FXR and/or TGR5 modulators for the treatment and prevention of disease.

SUMMARY OF THE INVENTION

The present invention relates to processes for preparing compounds of Formula (I) and compounds of Formula (II):

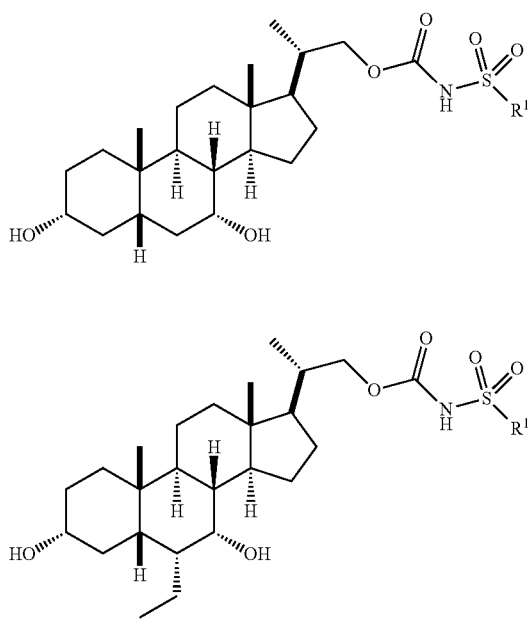

or a pharmaceutically acceptable salt thereof, wherein
R$^1$ is selected from the group consisting of:
1) substituted or unsubstituted —C$_1$-C$_8$ alkyl;
2) substituted or unsubstituted —C$_2$-C$_8$ alkenyl;
3) substituted or unsubstituted —C$_2$-C$_8$ alkynyl;
4) substituted or unsubstituted —C$_3$-C$_8$ cycloalkyl;
5) substituted or unsubstituted aryl;
6) substituted or unsubstituted arylalkyl;
7) substituted or unsubstituted 3- to 12-membered heterocycloalkyl;
8) substituted or unsubstituted heteroaryl;
9) substituted or unsubstituted heteroarylalkyl; and
10) NR$_a$R$_b$; wherein, R$_a$ and R$_b$ are each independently selected from hydrogen, substituted or unsubstituted —C$_1$-C$_8$ alkyl, substituted or unsubstituted —C$_2$-C$_8$ alkenyl, substituted or unsubstituted —C$_2$-C$_8$ alkynyl, substituted or unsubstituted —C$_3$-C$_8$ cycloalkyl. Alternatively R$_a$ and R$_b$ are taken together with the nitrogen atom to which they attached to form a 3- to 12-membered hetercyclic ring.

A preferred embodiment of a compound of Formula (I) is compound (VII):

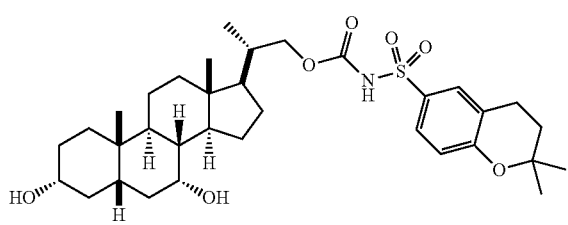

A preferred embodiment of a compound of Formula (II) is compound (VIII):

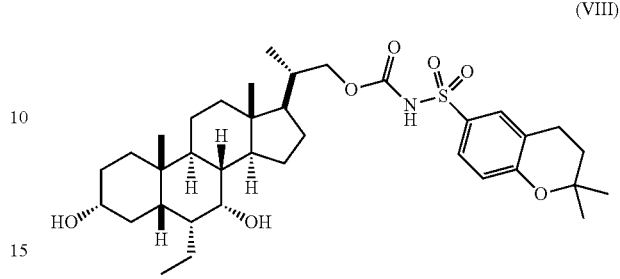

Another preferred embodiment of a compound of Formula (II) is compound (IX):

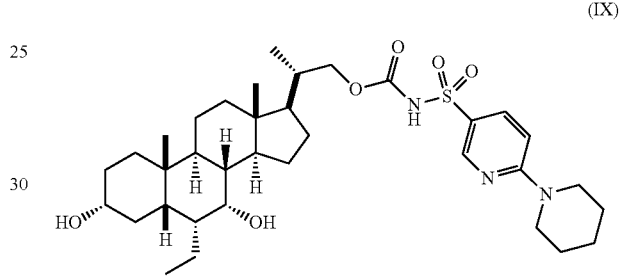

In certain embodiments, the present invention relates to methods of preparing the compound of Formula (III) which is an intermediate in the synthesis of compounds of Formula (I) and Formula (II).

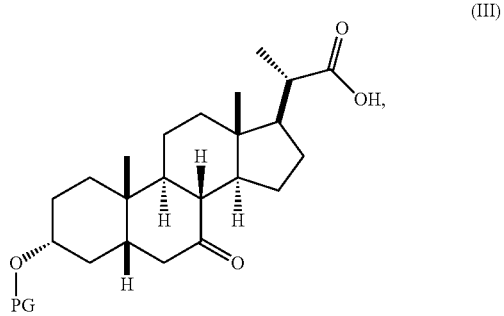

wherein PG is a hydroxyl protecting group such as, but not limited to, acetyl, THP, MOM, MEM, SEM, or a silyl group, such as TBS, TES, TMS, TIPS, or TBDPS. Preferably PG is TBS.

In certain embodiments, the present invention relates to methods of preparing a compound of Formula (IV) which is an intermediate in the synthesis of compounds of Formula (I).

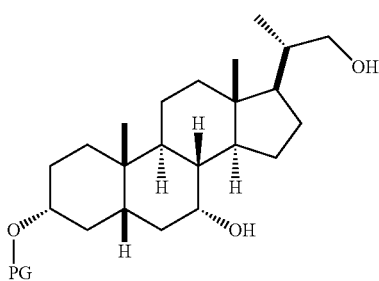
(IV)

In certain embodiments, the present invention relates to methods of preparing the compound of Formula (V) which is an intermediate in the synthesis of compounds of Formula (II).

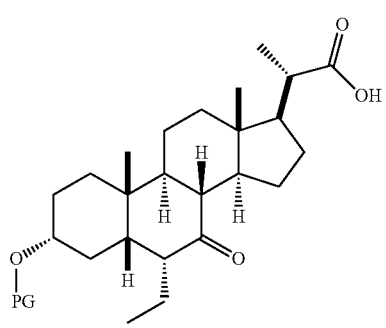
(V)

In certain embodiments, the present invention relates to methods of preparing the compound of Formula (VI) which is a useful intermediate in the synthesis of compounds of Formula (II).

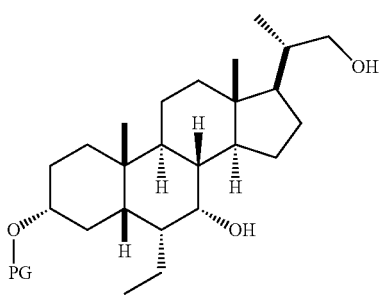
(VI)

In one embodiment, the process for preparing a compound of Formula (I) comprises the steps of:

1(a) converting compound 1 (CDCA) to the compound of Formula (III)

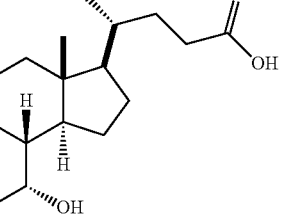
1 (CDCA)

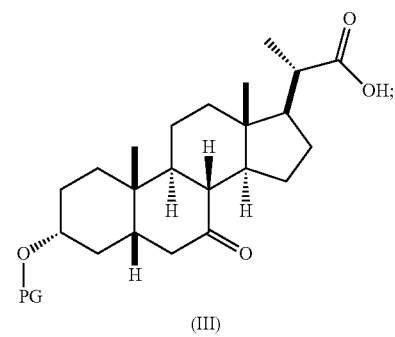
(III)

2(a) converting the compound of Formula (III) to the compound of Formula (IV)

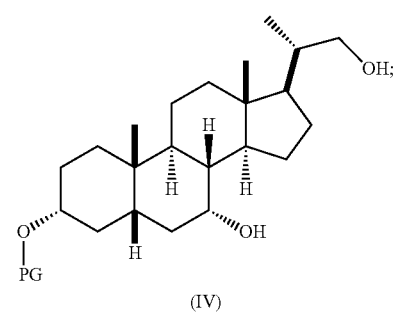
(III)

(IV)

3(a) converting the compound of Formula (IV) to the compound of Formula (I)

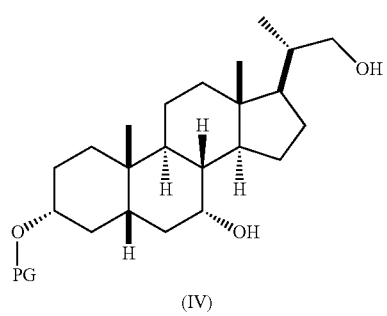

(IV)

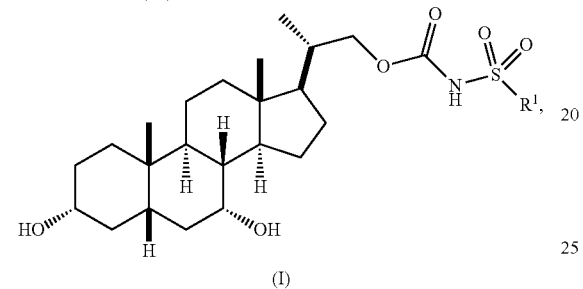

(I)

wherein PG, and R¹ is as previously defined.

In one embodiment, the process for preparing a compound of Formula (II) comprises the steps of:

1(a) converting compound 1 (CDCA) to the compound of Formula (III)

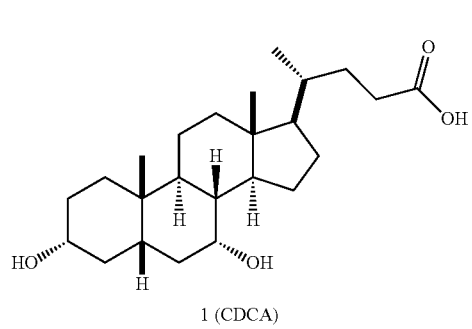

1 (CDCA)

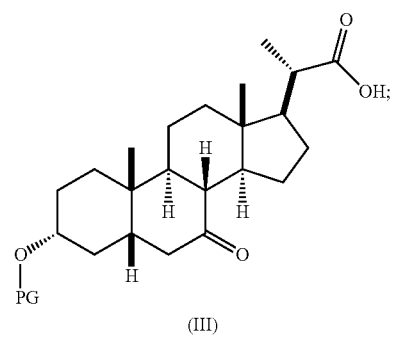

(III)

2(b) converting the compound of Formula (III) to the compound of Formula (V)

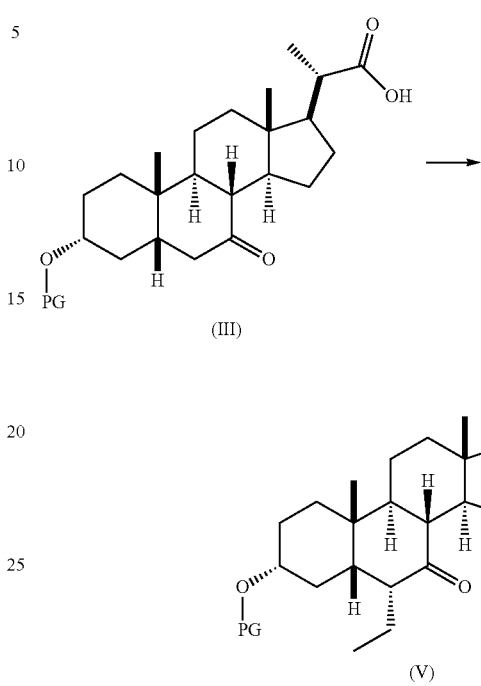

(III)

(V)

3(b) converting the compound of Formula (V) to the compound of Formula (VI)

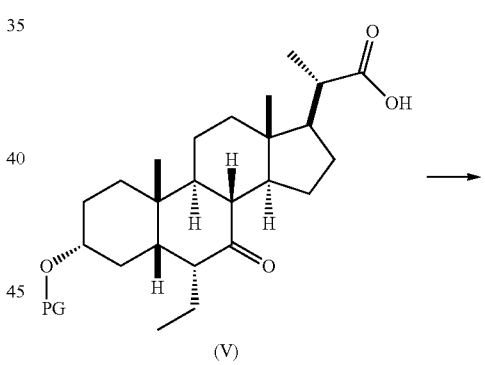

(V)

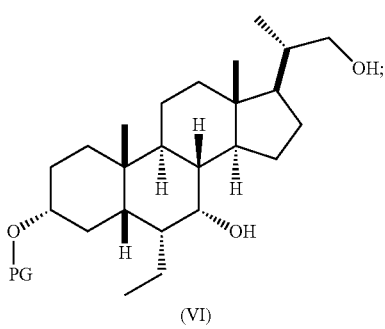

(VI)

4(b) converting the compound of Formula (VI) to the compound of Formula (II)

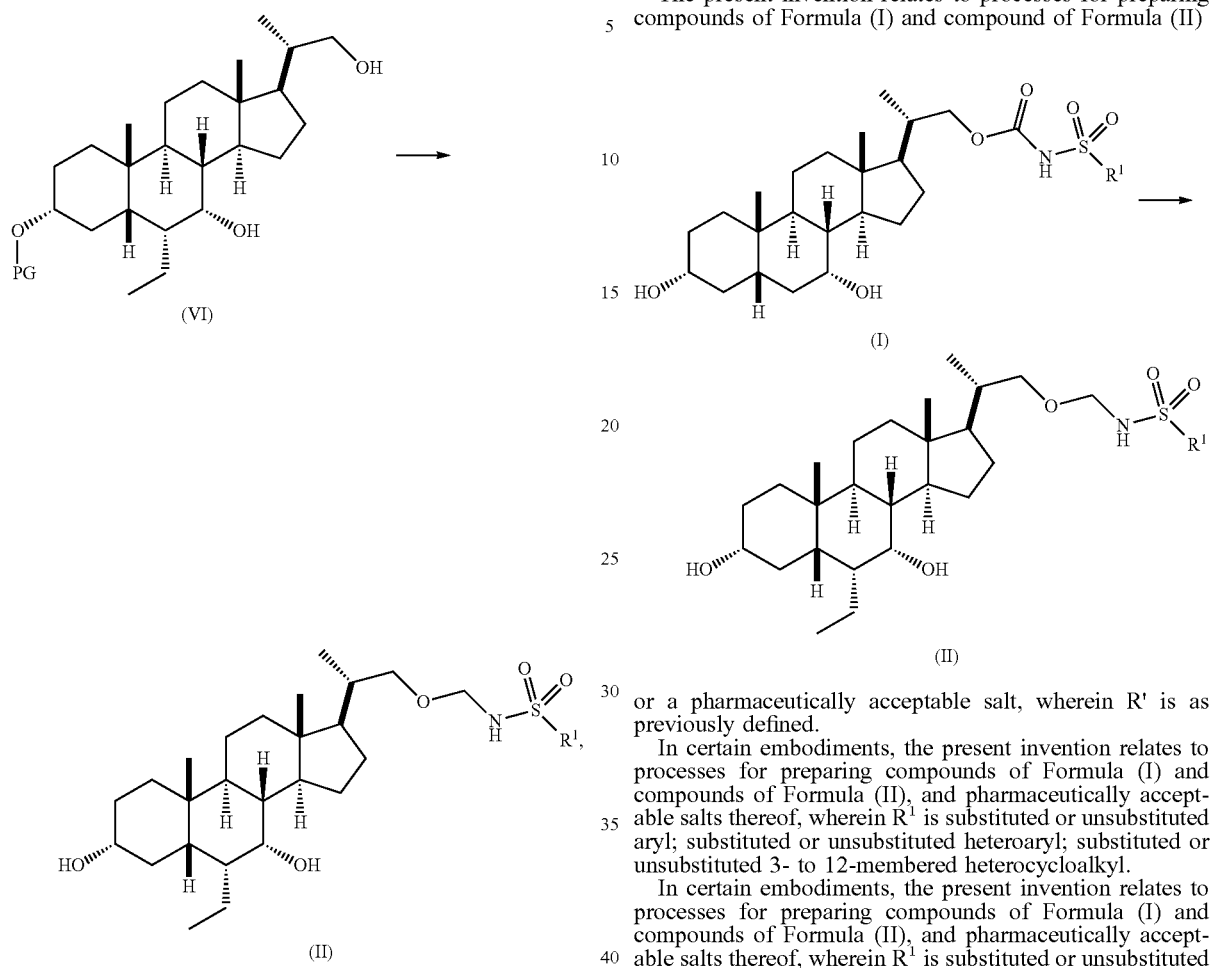

wherein PG and R¹ are as previously defined.

The invention further relates to methods for increasing product yield and decreasing process steps for intermediate and large scale production of compounds of Formula (I), Formula (II), Formula (III), Formula (IV), Formula (V), and Formula (VI).

The compounds of Formula (I), Formula (II), compound (VII), compound (VIII) and compound (IX) are useful for the treatment of a chronic liver disease, such as a disease selected from the group consisting of primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, and alpha 1-antitrypsin deficiency (WO2016/086218A1).

DETAILED DESCRIPTION OF THE INVENTION

The present invention relates to processes for preparing compounds of Formula (I) and compound of Formula (II)

or a pharmaceutically acceptable salt, wherein R¹ is as previously defined.

In certain embodiments, the present invention relates to processes for preparing compounds of Formula (I) and compounds of Formula (II), and pharmaceutically acceptable salts thereof, wherein R¹ is substituted or unsubstituted aryl; substituted or unsubstituted heteroaryl; substituted or unsubstituted 3- to 12-membered heterocycloalkyl.

In certain embodiments, the present invention relates to processes for preparing compounds of Formula (I) and compounds of Formula (II), and pharmaceutically acceptable salts thereof, wherein R¹ is substituted or unsubstituted phenyl; or substituted or unsubstituted pyridyl.

In certain embodiments, the present invention relates to processes for prearing compounds of Formula (I) and compounds of Formula (II), and pharmaceutically acceptable salts thereof, wherein R¹ is substituted or unsubstituted

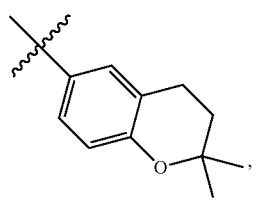 [SMILES: *c1ccc2c(c1)CCC(C)(C)O2 ; ","]

or substituted or unsubstituted

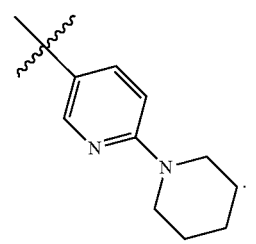 [SMILES: *c1ccc(N2CCCCC2)nc1 ; "."]

In another embodiment, the present invention relates to processes for preparing compound (VII).

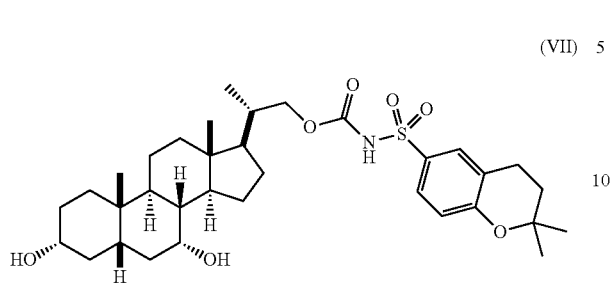
(VII)

In another embodiment, the present invention relates to processes for preparing compound (VIII).

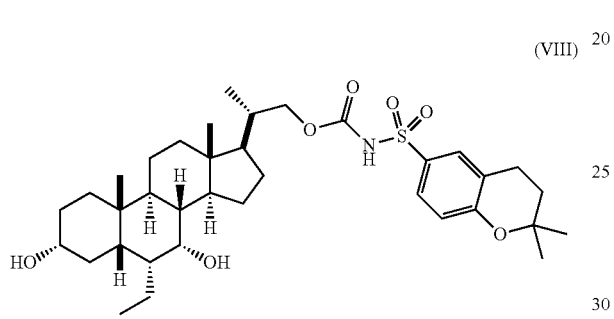
(VIII)

In another embodiment, the present invention relates to the processes for preparing compound (IX).

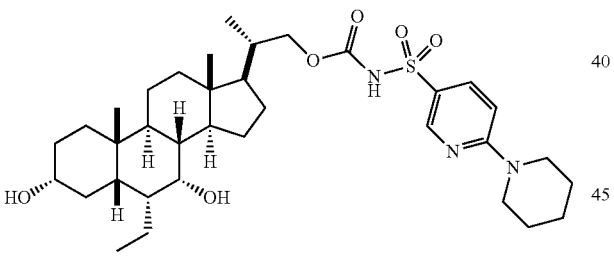
(IX)

In one embodiment, step 1(a) is set forth in scheme 1. The method comprises steps 1(a)(i): esterifying chenodeoxycholic acid (CDCA, compound 1) with a $C_1$-$C_6$-alkanol, preferably methanol or ethanol, more preferably methanol, to produce compound 2; 1(a)(ii): reacting compound 2 with a strong base in the presence of a suitable hydroxyl protecting agent and an electrophilic halogen source to produce compound 3; 1(a)(iii): eliminating the $R^2$ group in compound 3 to produce compound 4; 1(a)(iv): deprotecting compound 4 to produce compound 5; 1(a)(v): protecting compound 5 to produce compound 6; and 1(a)(vi): oxidatively cleaving and oxidizing compound 6 to produce compound (III).

Scheme 1

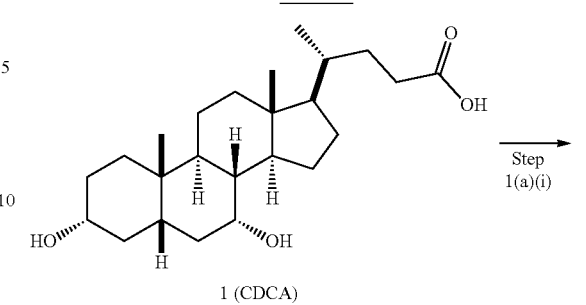
1 (CDCA)

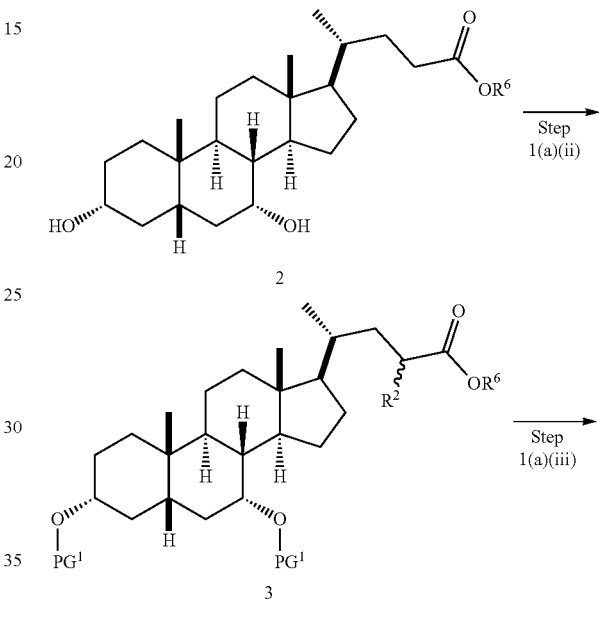
2

3

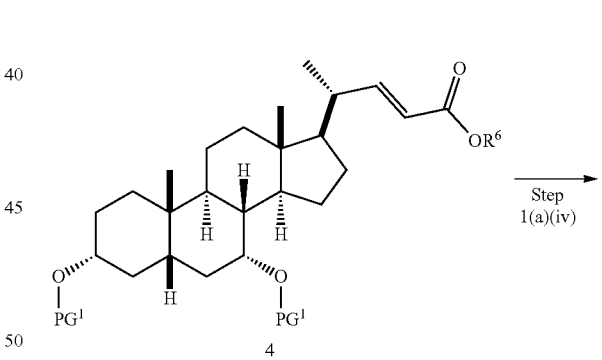
4

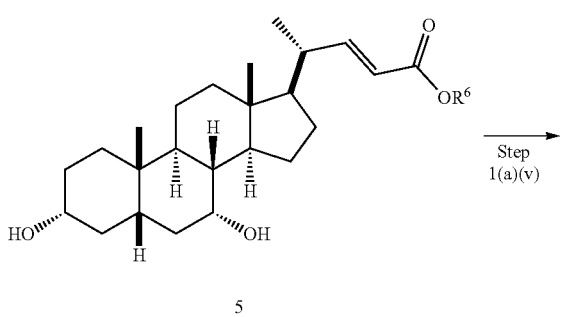
5

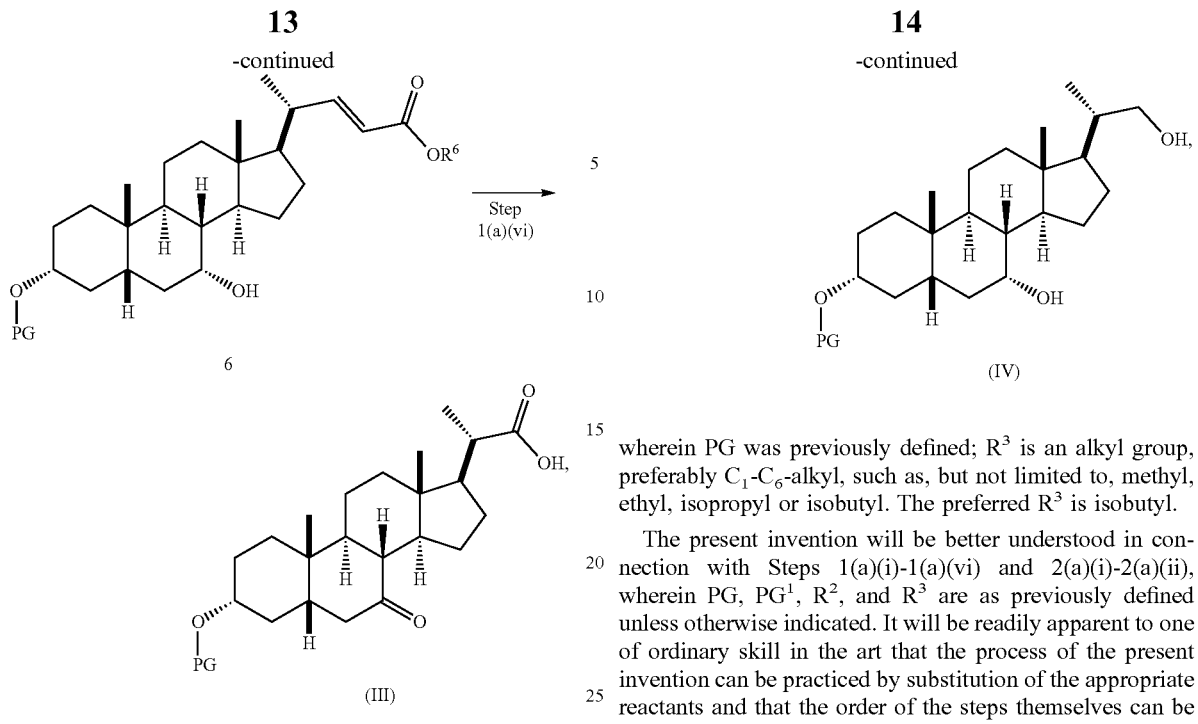

(III)

wherein PG is previously defined; PG¹ is a hydroxyl protecting group preferably selected from silyl groups, such as, but not limited to, TMS, TES, TBS, TIPS, and TBDPS; and $R^2$ is selected from Cl, Br, and I. The preferred PG¹ is TMS. The preferred PG is TBS. $R^6$ is $C_1$-$C_6$-alkyl, preferably methyl or ethyl and more preferably methyl.

Step 2(a) is conducted as set forth in scheme 2. Thus, in step 2(a)(i) the compound (III) reacts with chloroformate reagent $R_3OC(O)C_1$ to produce anhydride compound 7, followed by step 2(a)(ii), reducing compound 7 to produce compound (IV).

Scheme 2

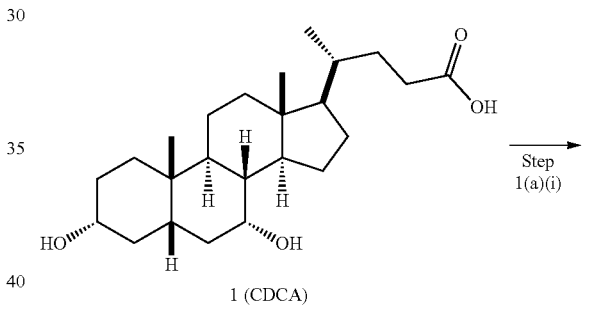

wherein PG was previously defined; $R^3$ is an alkyl group, preferably $C_1$-$C_6$-alkyl, such as, but not limited to, methyl, ethyl, isopropyl or isobutyl. The preferred $R^3$ is isobutyl.

The present invention will be better understood in connection with Steps 1(a)(i)-1(a)(vi) and 2(a)(i)-2(a)(ii), wherein PG, PG¹, $R^2$, and $R^3$ are as previously defined unless otherwise indicated. It will be readily apparent to one of ordinary skill in the art that the process of the present invention can be practiced by substitution of the appropriate reactants and that the order of the steps themselves can be varied.

Step 1(a)(i), Converting Compound 1 to Compound 2:

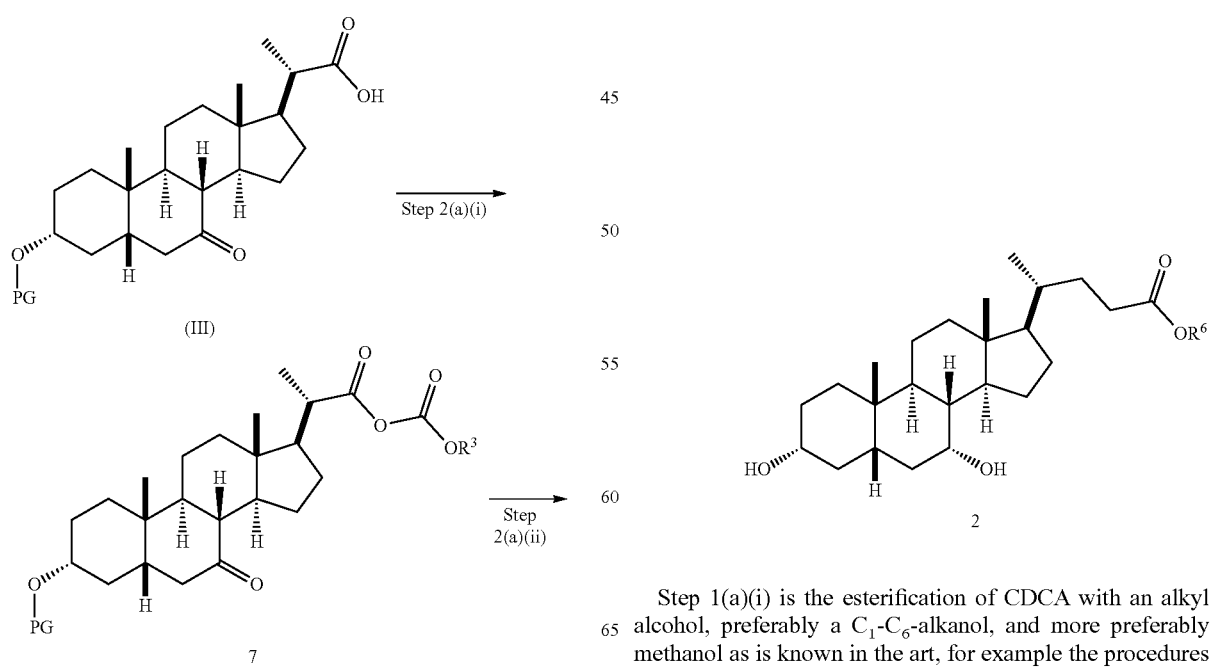

Step 1(a)(i) is the esterification of CDCA with an alkyl alcohol, preferably a $C_1$-$C_6$-alkanol, and more preferably methanol as is known in the art, for example the procedures described in *Tetrahedron*, 57(8), 1449-1481; 2001.

Step 1(a)(ii), converting compound 2 to compound 3:

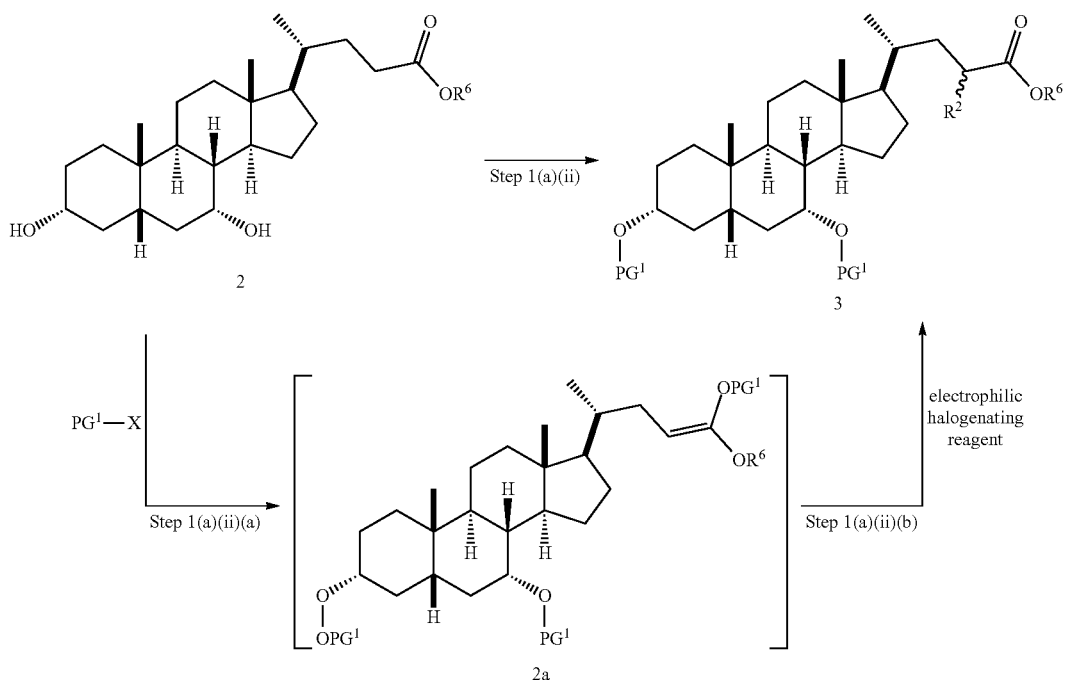

Step 1(a)(ii) is the conversion of compound 2 to compound 3 via halogenation of an intermediate silyl ketene acetal 2a. The silyl ketene acetal intermediate 2a is directly generated in situ by reacting compound 2 with a strong base, such as, but not limited to, LDA in the presence of a suitable hydroxyl protecting agent $PG^1$-X, wherein X is selected from Cl, Br, I, and OTf. The preferred hydroxyl protecting agent is TMS-$C_1$. In one aspect, the temperature is from −100° C. to −50° C. In one aspect, the temperature is from −90° C. to −60° C. In one aspect, the temperature is from −80 to −70° C. The silyl ketene acetal intermediate 2a reacts with an electrophilic halogenating reagent, such as, but not limited to, $Br_2$, $I_2$, I—Cl, I—Br, NBS, NIS, and 1,3-dibromo-5,5-dimethylhydantoin to give compound 3. The preferred electrophilic halogenating reagent is $I_2$.

Step 1(a)(iii), converting compound 3 to compound 4:

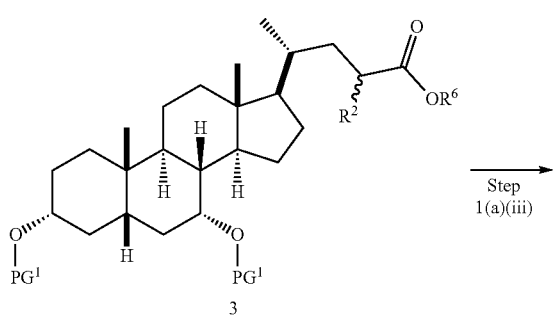

Step 1(a)(iii) is the elimination of H—$R^2$ from compound 3 to form compound 4. Compound 3 is treated with a suitable organic base, such as, but not limited to, DIPEA, $Et_3N$, DBU, DBN, or DABCO, in a solvent or solvent mixture such as, but not limited to, THF, DCM, acetonitrile, or toluene. The preferred organic base is DBU. In a preferred aspect, the solvent is THF. In a preferred aspect, compound 3 from Step 1(a)(ii) is used directly without further purification. The reaction can be carried out at a temperature ranging from −10° C. to 50° C. In a preferred aspect, the reaction temperature is from 0° C. to 30° C. In another preferred aspect, the reaction temperature is about 25° C.

Step 1(a)(iv), converting compound 4 to compound 5:

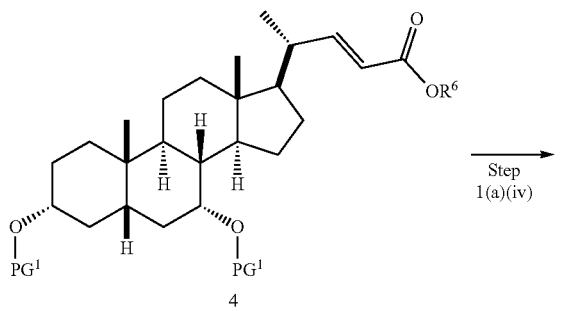
4

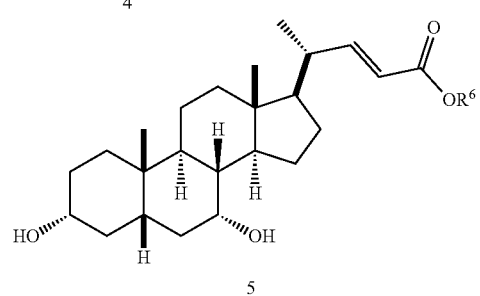
5

Step 1(a)(iv) is the removal of the protecting group, PG¹ of compound 4 to form compound 5. The protecting group can be removed under suitable deprotection conditions as are known in the art. For example, PG¹ can be removed by a deprotecting reagent such as, but not limited to, TBAF, or an acid such as HCl. Preferably compound 4 is treated with an acid in an aprotic solvent. In a preferred aspect of Step 1(a)(iv), compound 4 from Step 1(a)(iii) is used directly without further purification. Preferably compound 4 is treated with an acid, such as HCl, in an aprotic solvent such as, but not limited to, THF, 1,4-dioxane, MTBE, Et₂O, or a mixture of two. The preferred solvent is 1,4-dioxane. The reaction can be carried out at a temperature ranging from −10° C. to 50° C. In a preferred aspect, the reaction temperature is from 0° C. to 30° C. In another preferred aspect, the reaction temperature is about 25° C. In yet another preferred aspect, compound 4 is treated with HCl in 1,4-dioxane at room temperature to give compound 5. Compound 5 can be purified by column chromatography to provide compound 5. The overall yield for the conversion of compound 1 to compound 5 is greater than 60% after the purification of compound 5.

Step 1(a)(v), converting compound 5 to compound 6:

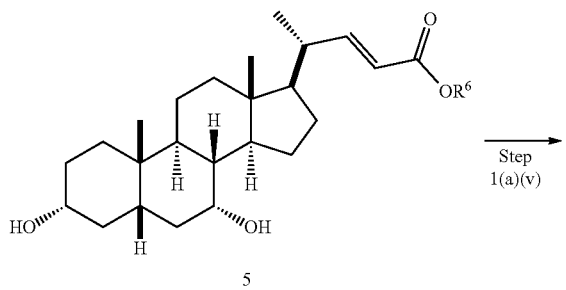
5

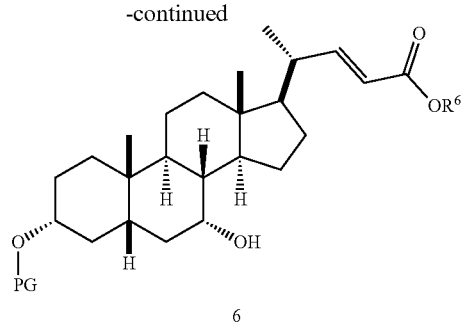
6

Step 1(a)(v) is the protection of the 3-hydroxyl of compound 5 with a suitable hydroxyl protecting agent PG-X, wherein X is a suitable leaving group, preferably Cl, Br, I, or OTf, in the presence of an organic base such as, but not limited to, imidazole, TEA, DIPEA to produce compound 6. The preferred hydroxyl protecting agent is TBS-Cl. The preferred organic base is imidazole. The reaction can be carried out at a temperature ranging from −10° C. to 50° C. In a preferred aspect, the reaction temperature is from 0° C. to 30° C. In another preferred aspect, the reaction temperature is about 25° C.

Step 1(a)(vi), converting compound 6 to compound III:

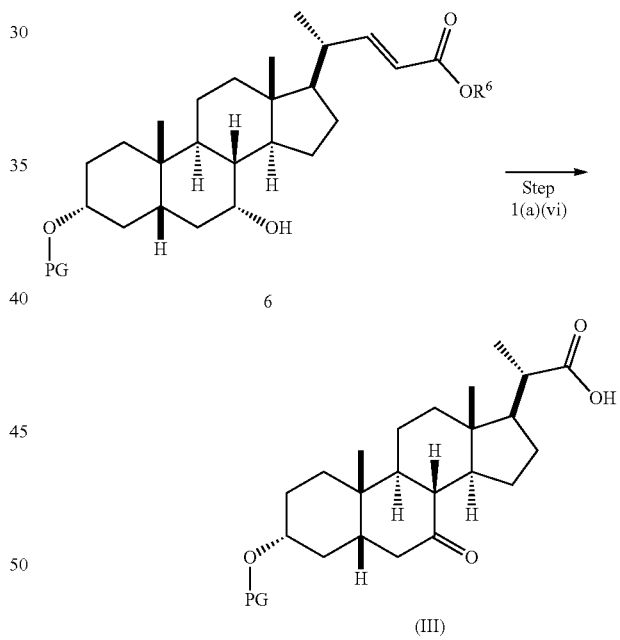

Step 1(a)(vi) is dihydroxylation, oxidative cleavage, and 7-OH oxidation of compound 6 with a suitable catalyst such as, but not limited to, RuCl₃ in the presence of a stoichiometric oxidant such as, but not limited to, NaIO₄, n-Bu₄N⁺ IO₄⁻, and NMO to produce compound (III). The reaction is conducted in the presence of a suitable base such as, but not limited to, K₂CO₃, Na₂CO₃, and 2,6-lutidine. The preferred oxidant is NaIO₄. The preferred base is K₂CO₃. The reaction is carried out in a solvent such as, but not limited to, H₂O, CCl₄, CH₃CN or EtOAc. The preferred solvent is a mixture of H₂O, CH₃CN, and EtOAc. The reaction can be carried out at a temperature ranging from −10° C. to 50° C. In a preferred aspect, the reaction temperature is from 0° C. to 30° C. In another preferred aspect, the reaction temperature is about 25° C. Compound (III) can be crystallized from organic solvent or solvent mixture such as, but not limited to, hexanes/EtOAc to provide compound (III) with purity greater than 95%.

Step 2(a)(i), converting compound (III) to compound 7:

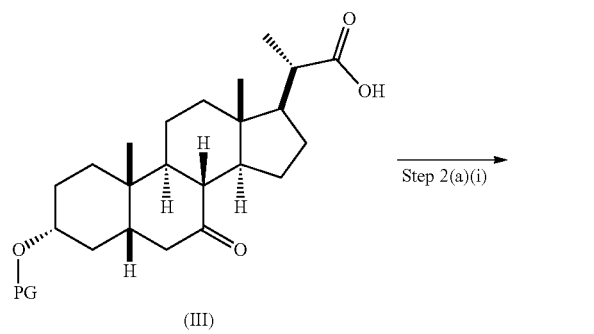

Step 2(a)(i) is the reaction of compound (III) with chloroformate $R^3OCOCl$ in the presence of an organic base such as, but not limited to, TEA or DIPEA to produce mixed anhydride 7. Step 2(a)(i) is preferably conducted in an aprotic solvent such as, but not limited to, DCM. The preferred chloroformate is isobutyl chloroformate, wherein $R^3$ is isobutyl. The preferred organic base is TEA. Compound 7 is isolated and used for next step reaction without purification.

Step 2(a)(ii), converting compound 7 to compound (IV):

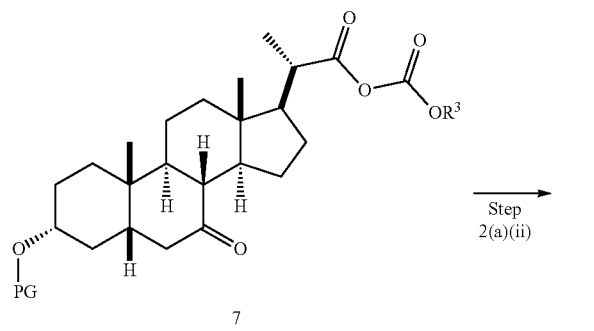

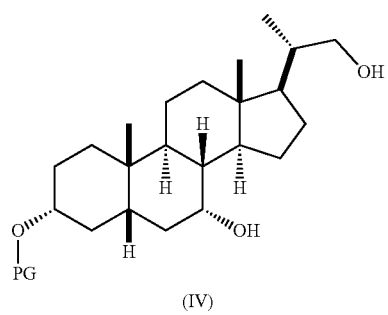

Step 2(a)(ii) is the reaction of compound 7 with a suitable reducing agent such as, but not limited to, $NaBH_4$, $LiBH_4$, $LiAlH_4$, or DIBAL to produce compound (IV). Step 2(a)(ii) is preferably carried out in a mixture of a protic and non-protic solvent, such as, but not limited to a mixture of water and THF. The reaction can be carried out at a temperature ranging from −10° C. to 50° C. In a preferred aspect, the reaction temperature is from 0° C. to 30° C. In another preferred aspect, the reaction temperature is about 25° C.

In one embodiment, Step 2(b) is conducted as set forth in scheme 3. The method comprises the steps of 2(b)(i): the simultaneous TBS deprotection and esterification of compound (III) to produce compound 8; 2(b)(ii): reacting compound 8 with a strong base in the presence of a suitable hydroxyl protecting agent to produce enol ether compound 9; 2(b)(iii): reacting compound 9 with acetaldehyde to produce compound 10; 2(b)(iv): hydrogenating compound 10 to produce compound 11; 2(b)(v): reacting compound 11 with base in a protic solvent or a mixture of a protic solvent and a non-protic solvent to produce compound (12); and 2(b)(vi): protecting compound 12 to produce compound (V).

Scheme 3

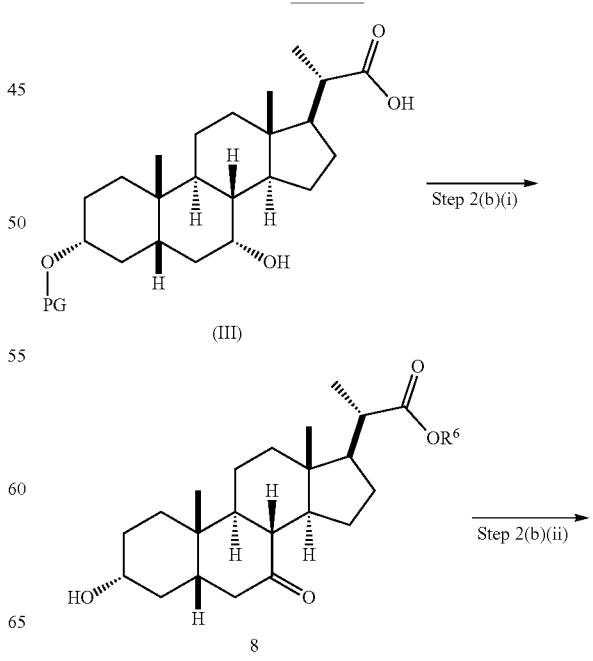

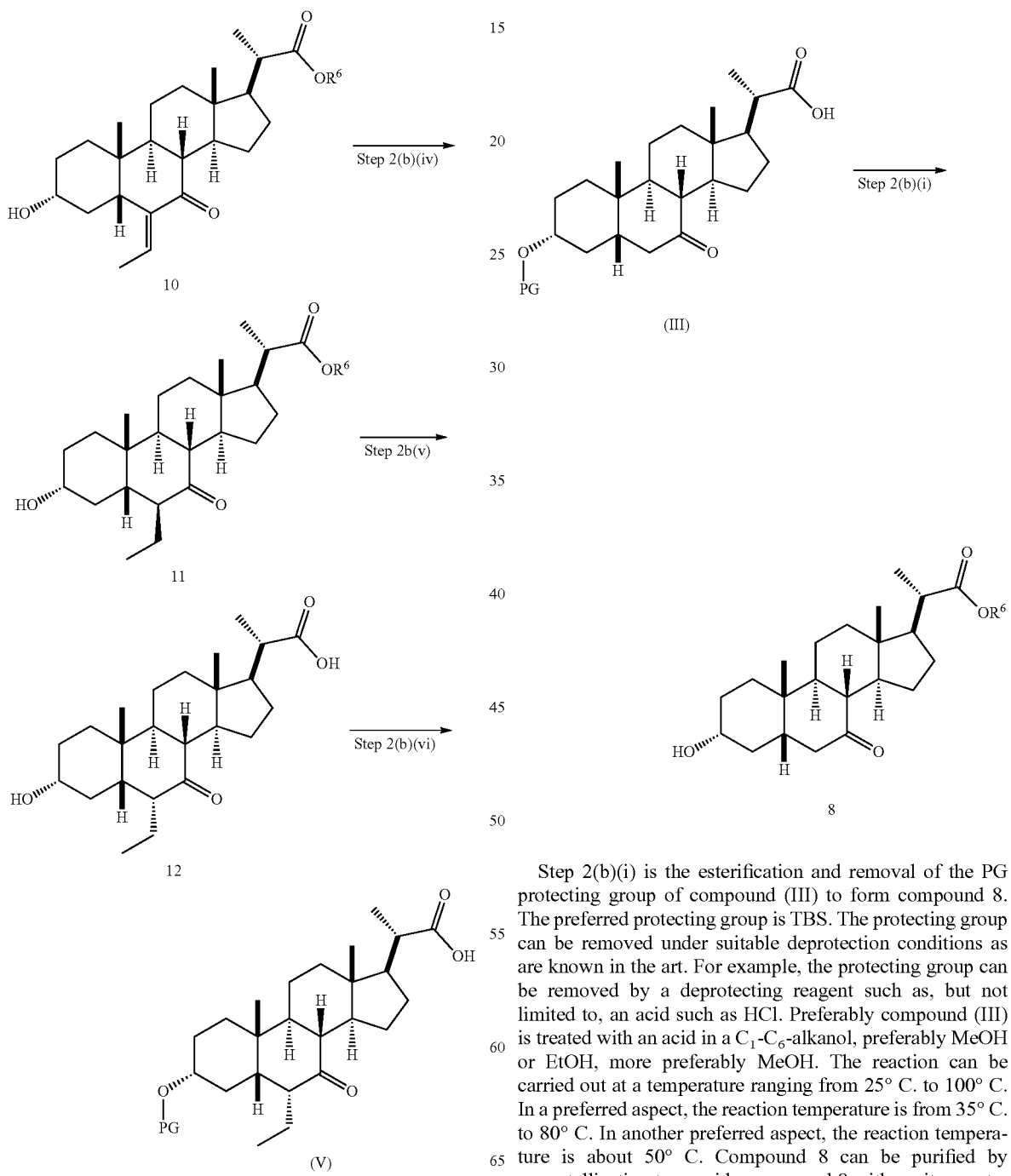

wherein PG is as previously defined; $PG^3$ is a hydroxy protecting group selected from silyl groups, such as, but not limited to, TMS, TES, TBS, TIPS, and TBDPS. The preferred $PG^3$ is TMS. $R_6$ is as previously defined.

The present invention will be better understood in connection with Steps 2(b)(i) to 2(b)(vi), wherein PG, $PG^3$ and $R^3$ are as previously defined unless otherwise indicated. It will be readily apparent to one of ordinary skill in the art that the process of the present invention can be practiced by substitution of the appropriate reactants and that the order of the steps themselves can be varied.

Step 2(b)(i), converting compound (III) to compound 8:

Step 2(b)(i) is the esterification and removal of the PG protecting group of compound (III) to form compound 8. The preferred protecting group is TBS. The protecting group can be removed under suitable deprotection conditions as are known in the art. For example, the protecting group can be removed by a deprotecting reagent such as, but not limited to, an acid such as HCl. Preferably compound (III) is treated with an acid in a $C_1$-$C_6$-alkanol, preferably MeOH or EtOH, more preferably MeOH. The reaction can be carried out at a temperature ranging from 25° C. to 100° C. In a preferred aspect, the reaction temperature is from 35° C. to 80° C. In another preferred aspect, the reaction temperature is about 50° C. Compound 8 can be purified by recrystallization to provide compound 8 with purity greater than 95%.

Step 2(b)(ii), converting compound 8 to compound 9:

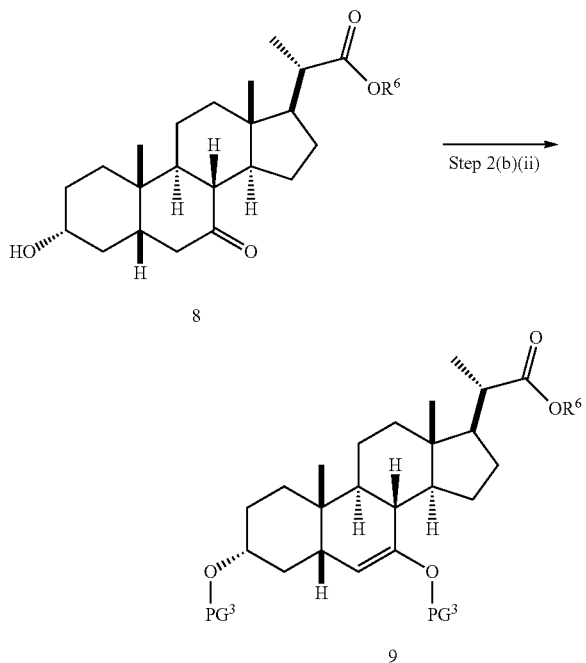

Step 2(b)(ii) is the formation of the silyl ether compound 9 by reacting compound 8 with a silylating agent in the presence of a base in an aprotic solvent, such as, but not limited to DCM and THF.

In one aspect of Step 2(b)(ii), the silylating agent is TMSCl, and the base is a strong organic base such as, but not limited to, NaHMDS, LiHMDS or LDA, and the reaction occurs at a lower temperature, such as about −78° C.

In another preferred aspect of Step 2(b)(ii), the silylating agent is TMSOTf and is used together with an organic base such as, but not limited to, TEA or DIPEA at a reaction temperature ranging from −20° C. to 30° C. In a preferred aspect, the reaction temperature is from about −5° C. to about 15° C. In another aspect, the temperature is about 0° C. The molar ratio of TMSOTf to compound 8, preferably ranges from 3 to 12. In one aspect, the molar ratio is 3 to 6. In one aspect, the molar ratio is 4.5 to 5.5.

In a preferred aspect, compound 9 can be used directly in Step 2(b)(iii) without purification.

Prior to conducting Step 2(b)(iii), it is preferred to remove the residual water in the crude compound 9 from Step 2(b)(ii) to control the decomposition of compound 9. In one aspect, compound 9 produced in Step 2(b)(ii) is dissolved in an aprotic solvent, such as, but not limited to, DCM, heptane, hexanes, or toluene, and is washed extensively with water to remove trace amount of the base. The water content is limited to <0.5% (Karl Fisher titration) by co-distillation with an anhydrous aprotic solvent, such as DCM, hexane, heptane, toluene, or THF.

Step 2(b)(iii), converting compound 9 to compound 10:

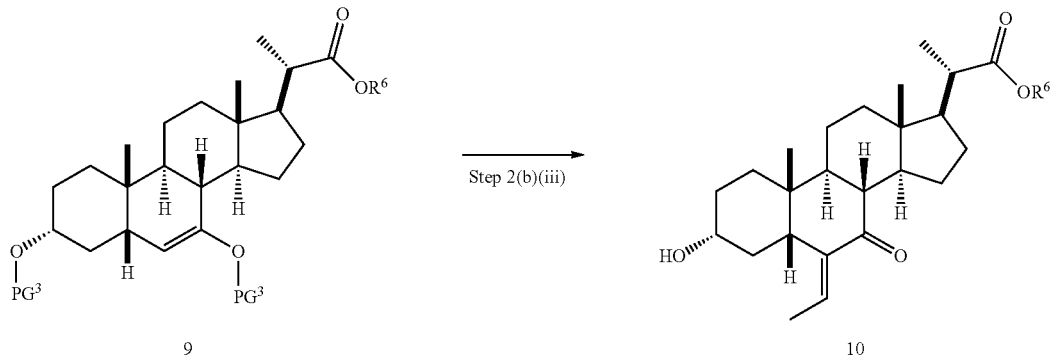

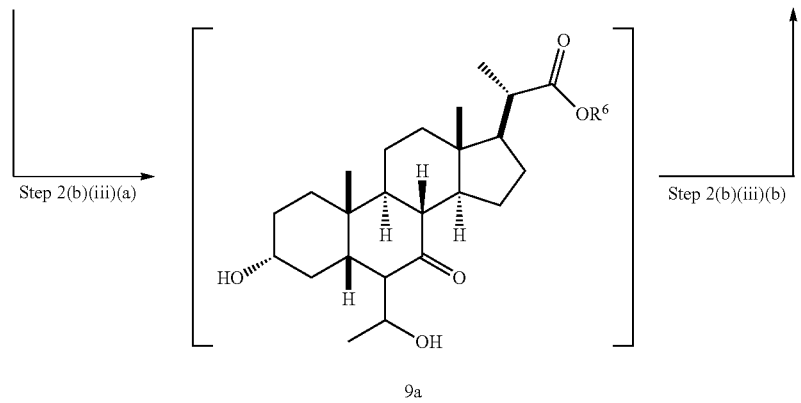

Step 2(b)(iii) is an aldol reaction of compound 9 with acetaldehyde to produce intermediate compound 9a, followed by elimination to form compound 10 in the presence of a Lewis acid, such as, but not limited to, BF$_3$.Et$_2$O or Ti(OiPr)$_4$. In one aspect of Step 2(b)(iii), the Lewis acid is BF$_3$.Et$_2$O. The reaction is carried out in an aprotic solvent, such as, but not limited to, DCM. The reaction temperature is preferably from about −78° C. to 25° C. In one aspect, the reaction temperature is from about −78° C. to about −50° C. In another preferred aspect, the reaction temperature is about −60° C.

Following the reaction of compound 9 with acetaldehyde at about −78° C. to about −50° C. (step 2(b)(iii)(a)), the aldol product compound 9a is formed initially as the major product. Methanol is then added to the reaction mixture to quench the reaction and facilitate the elimination to form the olefin compound 10 (step 2(b)(iii)(b). Alternatively the reaction is allowed to proceed at a higher temperature, such as from −10° C. to room temperature, without the addition of methanol to facilitate the olefin formation to provide compound 10.

In one aspect of Step 2(b)(iii), compound 10 is a mixture of E- and Z-olefin isomers as illustrated by the structures of compound 10A below. The E/Z ratio can be 1/1 to >9/1.

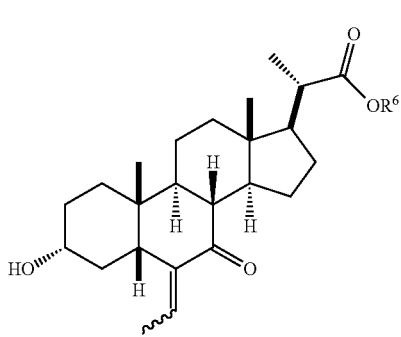

10A

Compound 10 can be purified by column chromatography to provide compound 10 with purity greater than 95%. In a preferred aspect, compound 10 can be used directly in Step 2(b)(iv) without purification.

In one aspect of Step 2(b)(iii), E-isomer compound 10 is obtained as the dominant isomer (E-isomer 10 is greater than 80% and Z-isomer is less than 20%). In another aspect, the E-isomer is greater than 90% and Z-isomer is less than 10%. In another aspect, the E-isomer is greater than 95% and Z-isomer is less than 5%.

In one aspect of Step 2(b)(iii), the crude product 10 contains less than 5% of ketone compound 8. In another aspect, the crude product 10 contains less than 3% of ketone compound 8. In another aspect, the crude product 10 contains less than 2% of ketone compound 8.

Step 2(b)(iv), converting compound 10 to compound 11:

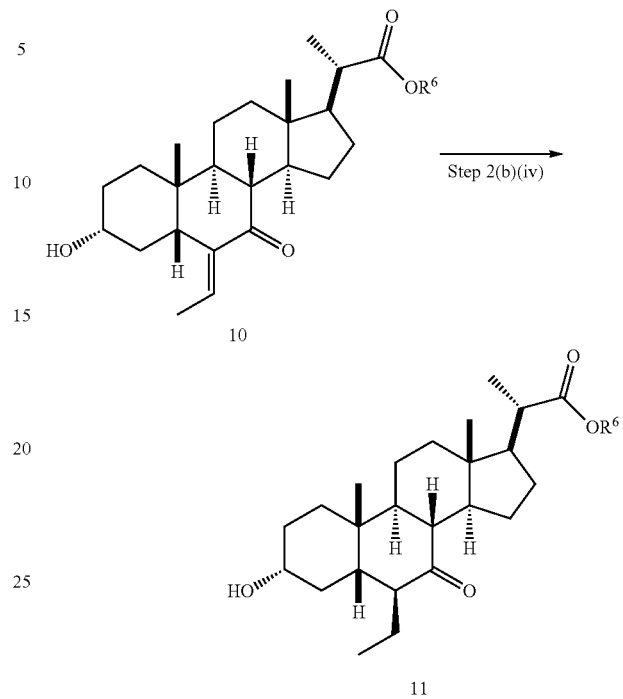

In Step 2(b)(iv), compound 10 from Step 2(b)(iii) is converted to compound 11 via a catalytic hydrogenation to reduce the olefin. In one aspect of Step 2(b)(iv), compound 10 from Step 2(b)(iii) has been purified via column chromatography. In a preferred aspect of Step 2(b)(iv), the crude product 10 obtained after work-up of Step 2(b)(iii) is used directly without purification. In one aspect of Step 2(b)(iv), the crude product 10 contains both E- and Z olefin isomers (10A). The percentage of Z-isomer preferably ranges from 0% to 50%.

The catalytic hydrogenation is carried out in the presence of a catalyst such as, but not limited to, palladium on carbon (Pd/C), Pd(OAc)$_2$, Pd(OH)$_2$ and PtO$_2$. The preferred catalyst is Pd/C. The palladium content of this Pd/C can range from about 5% to about 10%. The amount of catalyst can be rang from about 1 mol % to about 10 mol %. The hydrogen source can be, but is not limited to, hydrogen gas and ammonium formate. The pressure of hydrogen gas preferably ranges from atmospheric pressure to about 500 psi. In one aspect of Step 2(b)(iv), the pressure of hydrogen gas is atmospheric pressure. In one aspect, the pressure of hydrogen gas is from about 50 to about 150 psi. The reaction temperature preferably ranges from about 5° C. to about 120° C. In one aspect, the reaction temperature is from about 5° C. to about 80° C. In one aspect of Step 2(b)(iv), the reaction temperature is from about 20° C. to about 50° C. In one aspect, the reaction temperature is about 25° C. The reaction can be conducted in a protic or aprotic solvent or mixture of two solvents. Suitable solvents include, but are not limited to, methanol, ethanol, isopropanol, tert-butanol, and THF. In one aspect of Step 2(b)(iv), the solvent is a mixture of methanol and THF. In another one aspect of Step 2(b)(iv), ethanol and THF mixture is used as the solvent.

In certain embodiments, compound 11 is produced as a mixture of the 6α-ethyl isomer and the 6β-ethyl isomer. In certain embodiments, the 6β-ethyl isomer is the dominant isomer in the product. In one aspect of Step 2(b)(iv), the crude compound 11 contains less than 20% of 6α-ethyl isomer. In one aspect of Step 2(b)(iv), the crude compound 11 contains less than 10% of 6α-ethyl isomer. In one aspect of Step 2(b)(iv), the crude compound 11 contains less than 5% of 6α-ethyl isomer. Compound 11 can be used directly in Step 2(b)(v) without purification.

Although compound 11 is shown above as the 6β-ethyl isomer, in embodiments in which the compound is a mixture of the 6-alpha and 6-beta-ethyl isomers, it can be represented as compound 11A below.

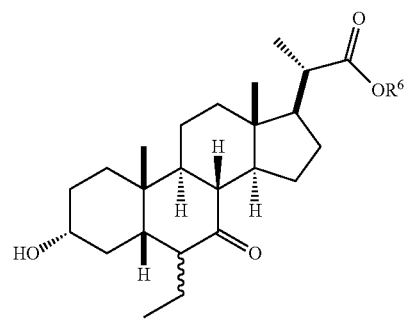

11A

Step 2(b)(v), converting compound 11 to compound 12:

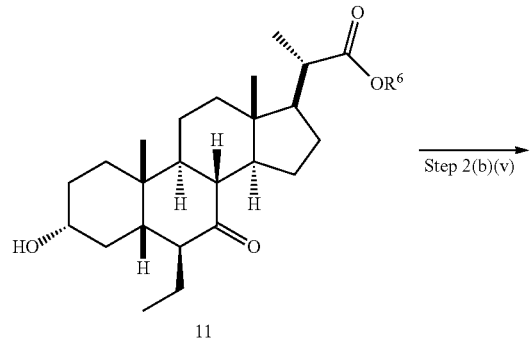

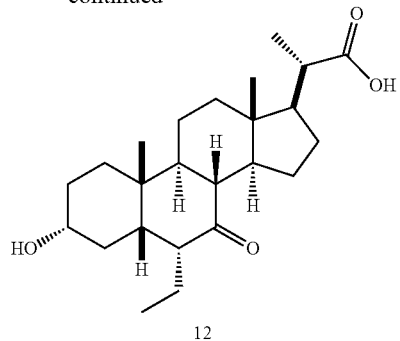

12

Step 2(b)(v) is the epimerization of the 6β-ethyl isomer of compound 11 to the 6α-ethyl isomer, compound 12, under basic conditions. In one aspect of Step 2(b)(v), the crude product obtained from Step 2(b)(iv), which contains both 6β-ethyl isomer and 6α-isomer, is used in the Step 2(b)(vi) without further purification.

The base can be, but is not limited to, sodium hydroxide or potassium hydroxide. In one aspect, the base is an aqueous sodium hydroxide solution. In one aspect of Step 2(b)(vi), the base is a 50% solution of sodium hydroxide in water.

In one aspect of Step 2(b)(v), the crude product of Step 2(b)(iv) is directly used in Step 2(b)(v) after removal of the catalyst, such as Pd/C, by filtration. In one aspect of Step 2(b)(v), the crude product 11 is used after the removal of the catalyst and the solvent.

Step 2(b)(v) is preferably carried out in a protic solvent such as, but not limited to methanol or ethanol, or a mixture of a protic and non-protic solvent, such as, but not limited to a mixture of methanol or ethanol and THF.

In one aspect of Step 2(b(v), the solvent is ethanol. In another aspect of Step 2(b)(v), the solvent is methanol. In another aspect of Step 2(b)(v), the solvent is a mixture of ethanol and THF. In another aspect of Step 2(b)(v), the solvent is a mixture of methanol and THF. Compound 12 can be used directly in Step 2(b)(vi) without purification.

Step 2(b)(vi), converting compound 12 to compound (V):

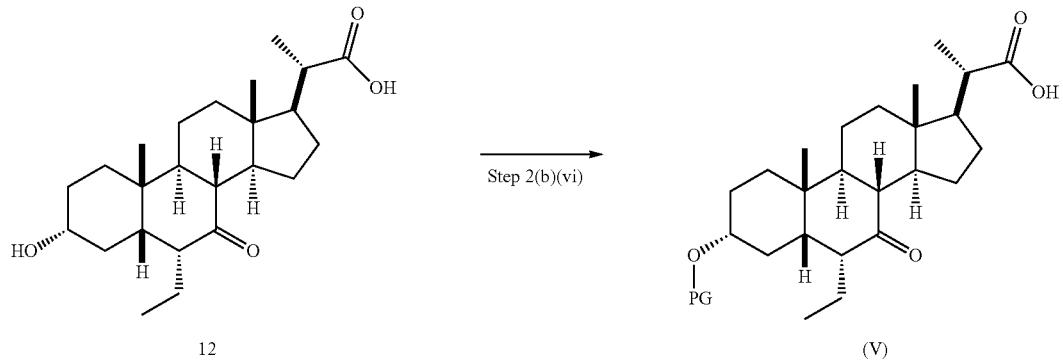

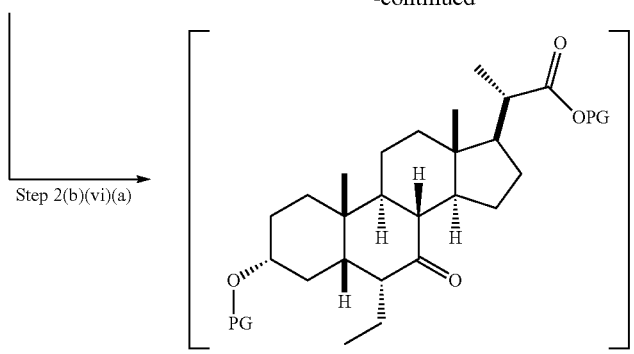

12a

Step 2(b)(vi) is the protection of the 3-hydroxyl and acid of compound 12 with a suitable hydroxyl protecting agent PG-X, wherein X is a suitable leaving group, preferably Cl, Br, I, or OTf, in the presence of an organic base such as, but not limited to, imidazole, TEA, DIPEA to produce intermediate compound 12a, followed by deprotection of the carboxylic acid with a suitable base in a protic solvent to produce compound (V). The preferred hydroxyl protecting agent is TBS-Cl. The preferred organic base is imidazole. The preferred base is $K_2CO_3$. The preferred protic solvent is MeOH. The reaction can be carried out at a temperature ranging from −10° C. to 50° C. In a preferred aspect, the reaction temperature is from 0° C. to 30° C. In another preferred aspect, the reaction temperature is about 25° C.

Compound (V) can be crystallized from organic solvent or mixture of organic solvents such as, but not limited to hexanes/$CH_2Cl_2$ to provide compound (V) with purity greater than 95%.

In one embodiment, Step 3(b) is conducted as set forth in scheme 4. The method comprises the steps of 3(b)(i): reacting compound (V) with a suitable acylating reagent to produce compound 13; and 3(b)(ii): reducing compound 13 to produce compound (VI).

Scheme 4

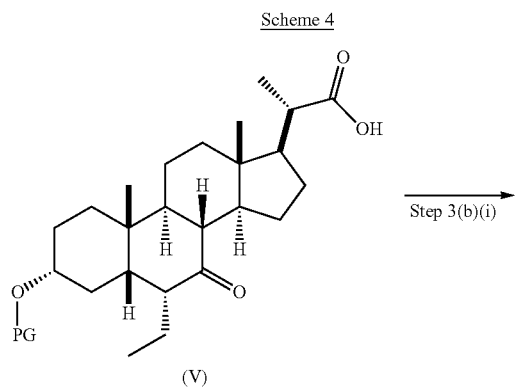

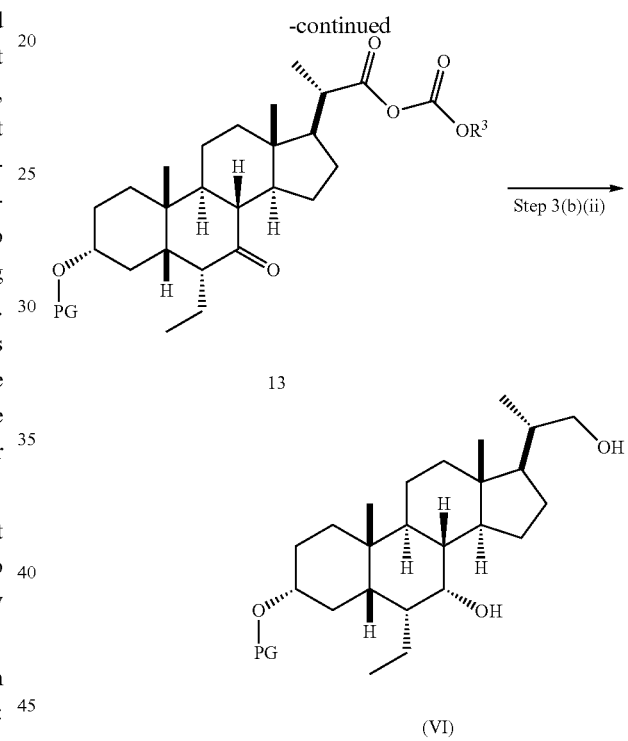

wherein $R^3$ is as previously defined.

The process of the present application has never been reported in the art. The synthesis of compound (VI) has been described in US 2016/0289262 from obeticholic acid in 6 steps. The synthesis of obeticholic acid was reported in US 2013/0345188 starting from KLCA in 6 steps. Overall, the known process of preparing alcohol compound (VI) involved a 12-step synthesis from KLCA. This previous process included low yielding steps, and required multiple column chromatography steps, which is expensive and not suitable for large scale commercialization. Additionally several toxic and dangerous reagents were used. The process of the present invention of preparing compound (V) takes six steps from compound (III) with good overall yield and requires only one column chromatography operations. Key intermediates, such as compound 12, can be obtained via crystallization in high purity. Also compound (V) can be obtained via crystallization in high purity. Compound (V) can be converted to compound (VI) via mixed anhydride formation followed by reduction.

Step 3(b)(i), converting compound (V) to compound 13:

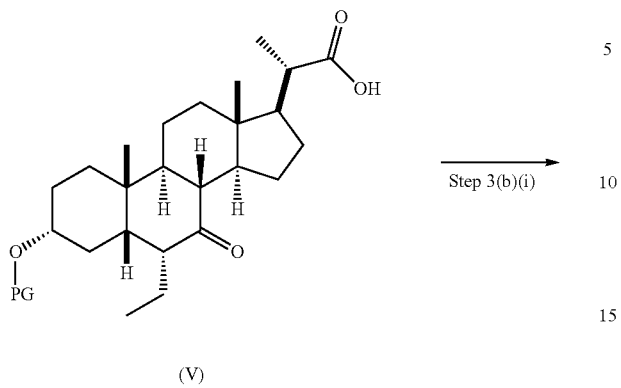

(V)

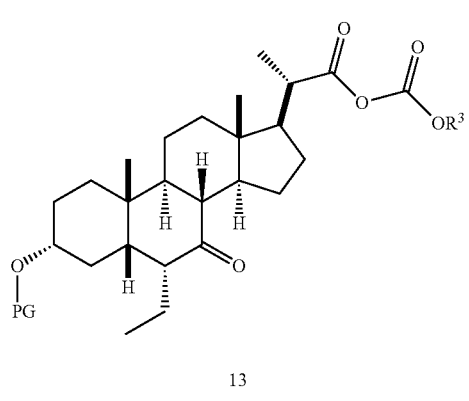

13

Step 3(b)(i) is the reaction of compound (V) with a suitable chloroformate R³OCOCl in the presence of an organic base such as, but not limited to, TEA or DIPEA to produce mixed anhydride 13. Step 3(b)(i) can be conducted in an aprotic solvent such as, but not limited to, DCM. The preferred chloroformate is isobutyl chloroformate, wherein R³ is isobutyl. The preferred organic base is TEA. Compound 13 is isolated in crude form and used without further purification.

Step 3(b)(ii), converting compound 13 to compound (VI):

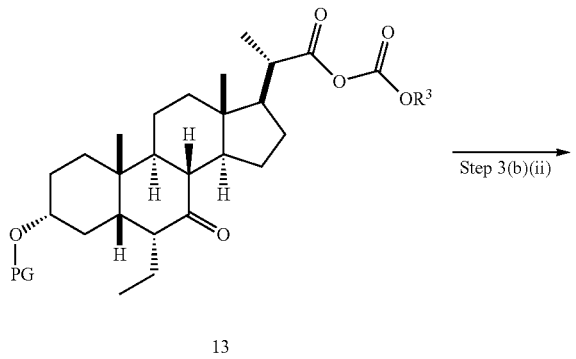

13

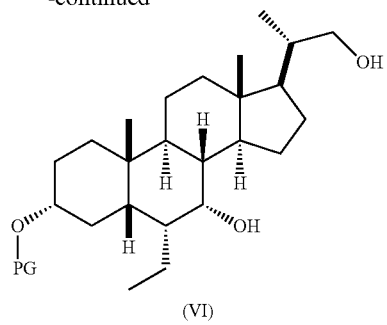

(VI)

Step 3(b)(ii) is the reaction of compound 13 with a suitable reducing agent such as, but not limited to, NaBH₄, LiBH₄, LiAlH₄, or DIBAL to produce compound (VI). Step 3(b)(ii) is preferably carried out in a mixture of a protic and non-protic solvent, such as, but not limited to a mixture of water and THF. The reaction can be carried out at a temperature ranging from −10° C. to 50° C. In a preferred aspect, the reaction temperature is from 0° C. to 30° C. In another preferred aspect, the reaction temperature is about 25° C.

Compound VI can be purified by column chromatography to provide compound VI with purity greater than 95%.

Process for Preparing a Compound of Formula (I)

The current invention also includes a process for preparing a compound of Formula (I) starting with the compound (IV) as shown in Scheme 5.

Scheme 5

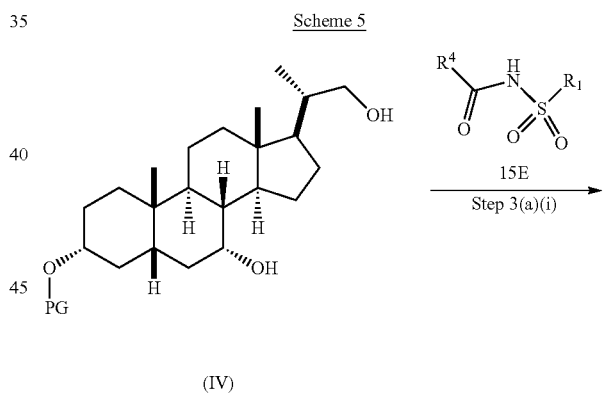

(IV)

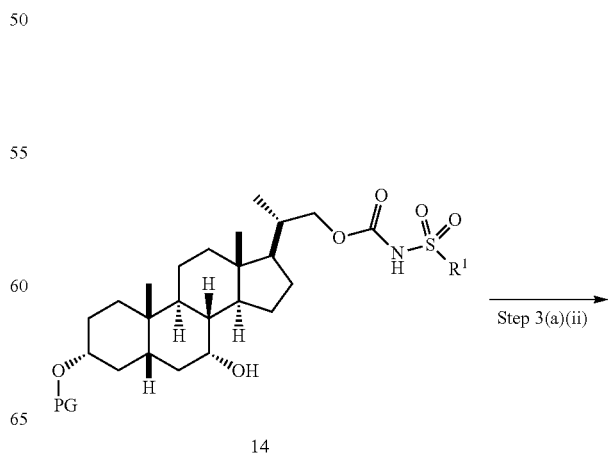

14

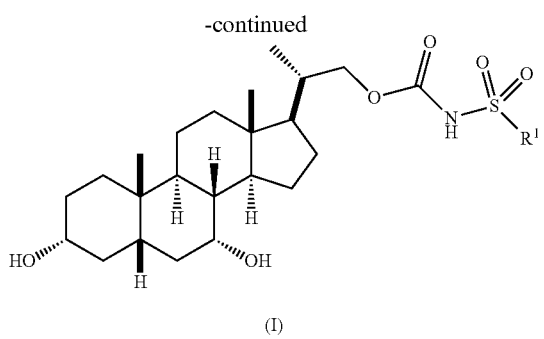

(I)

wherein R⁴ is imidazol-1-yl, alkyl-O— aryl-O, Cl, or CCl₃; R¹ is as previously defined.

Step 3(a)(i), converting compound (IV) to compound of formula 14:

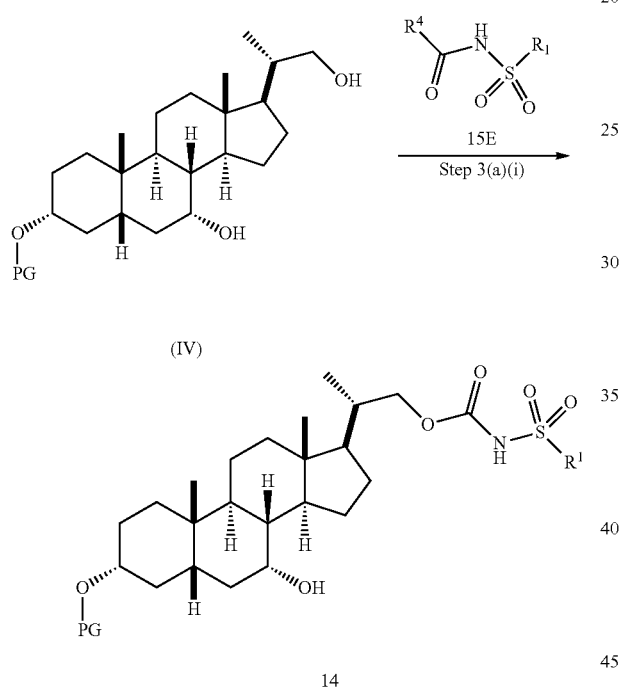

Step 3(a)(i) involves converting the compound (IV) to a compound of formula 14, wherein R¹ is as previously defined, by reacting the compound (IV) with a compound represented by 15E,

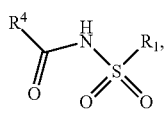

wherein, R⁴ is imidazol-1-yl, alkyl-O— aryl-O, Cl, or CCl₃, and R¹ is as previously defined, in the presence of an organic base. The reaction is preferably carried in an aprotic solvent, such as, but not limited to, THF, DCM or toluene. In one preferred aspect, the reaction solvent is THF. Suitable organic bases include, but are not limited to, triethylamine, and diisopropylethylamine. DMAP, ranging from 1 mol % to 50 mol %, can be added to facilitate the reaction. The reaction temperature preferably ranges from about 0° C. to about 80° C. In one aspect, the reaction is carried out at about 0° C. In another aspect, the reaction is carried out at about room temperature (about 25° C.). In yet another aspect, the reaction is carried out at about 50° C.

Preferably R⁴ in compound 15E is imidazol-1-yl, MeO—, EtO- or PhO—. More preferably R⁴ is PhO—.

Step 3(a)(ii) converting compound of formula 14 to compound of Formula (I):

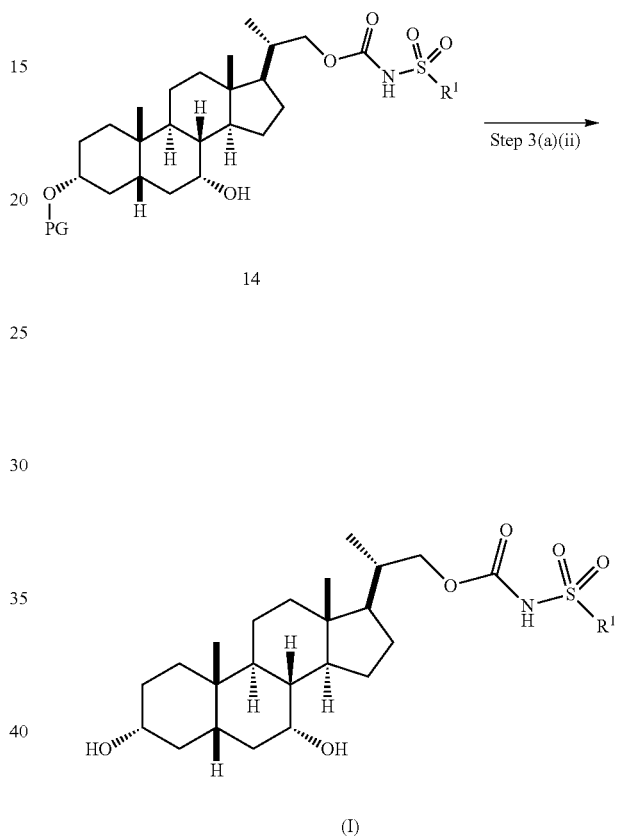

Step 3(a)(ii) is the removal of the PG protecting group of compound 14 to form compound (I), wherein R¹ is as previously defined. The PG protecting group can be removed under suitable deprotection conditions as are known in the art. The preferred PG protecting group is the TBS, Preferably, the protecting group is removed by a deprotecting reagent such as, but not limited to, TBAF, or an acid such as HCl. Preferably compound 14 is treated with an acid in a protic solvent. Preferably compound 14 is treated with an acid, such as HCl, in a protic solvent such as, but not limited to, MeOH, EtOH, i-PrOH, H₂O, or a mixture of two. The preferred solvent is MeOH. The reaction can be carried out at a temperature ranging from −10° C. to 50° C. In a preferred aspect, the reaction temperature is from 0° C. to 30° C. In another preferred aspect, the reaction temperature is about 25° C.

Process to Prepare Compound (VII)

The process of the current invention also includes a process for preparing compound (VII) starting from compound (IV) following the process described in Scheme 6.

Scheme 6

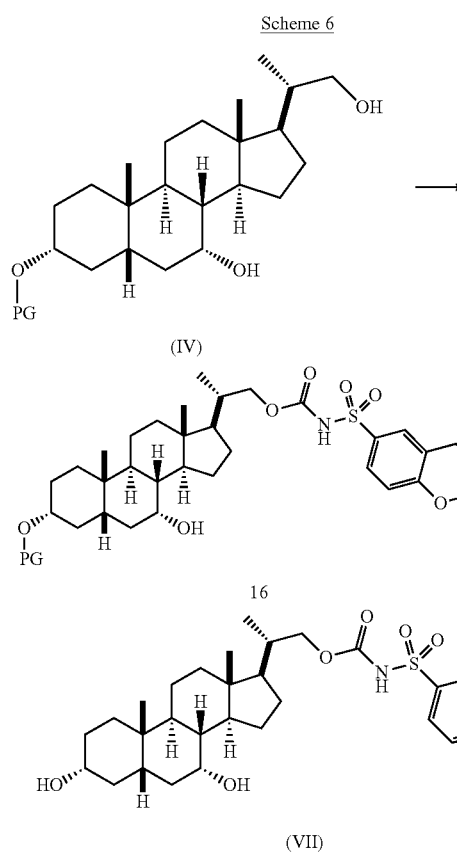

The process involves the conversion of alcohol compound (IV) to a sulfonyl carbamate 16 with an appropriate reagent, such as an agent selected from 15A, 15B, 15C and 15D, in the presence of an organic base.

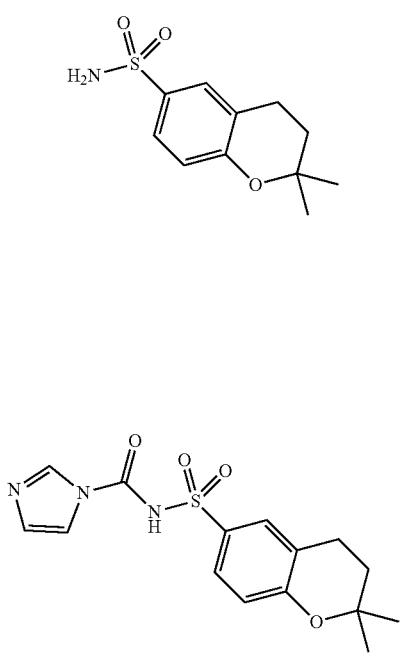

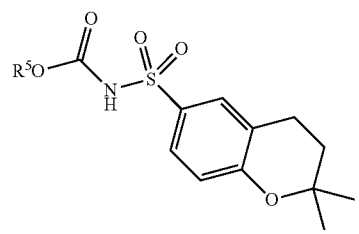

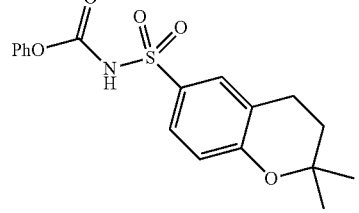

In one aspect, the reagent is 15B which can be formed by reacting sulfonamide compound 15A with CDI.

In another aspect, the reagent is sulfonylcarbamate compound 15C, wherein $R^5$ is alkyl or aryl, preferably methyl, ethyl, or phenyl. The preferred reagent is 15D.

In one aspect, the alcohol compound (IV) reacts with 15D in an aprotic solvent, such as, but not limited to, THF, DCM or toluene. In one preferred aspect, the reaction solvent is THF. Suitable organic bases include, but are not limited to, triethylamine, diisopropylethylamine. DMAP, ranging from 1 mol % to 50 mol %, can be added to facilitate the reaction. The reaction temperature preferably ranges from about 0° C. to about 80° C. In one aspect, the reaction is carried out at about 0° C. In another aspect, the reaction is carried out at about room temperature (about 25° C.). In yet another aspect, the reaction is carried out at a 50° C. Compound 16 can be purified by column chromatography to provide compound 16 with purity greater than 95%.

In one aspect, compound 16 reacts with a deprotecting reagent such as, but not limited to, TBAF, or an acid such as HCl. Preferably compound 16 is treated with an acid in a protic solvent. Preferably compound 16 is treated with an acid, such as HCl, in a protic solvent such as, but not limited to, MeOH, EtOH, i-PrOH, H₂O, or a mixture of two. The preferred solvent is MeOH. The reaction can be carried out at a temperature ranging from −10° C. to 50° C. In a preferred aspect, the reaction temperature is from 0° C. to 30° C. In another preferred aspect, the reaction temperature is about 25° C. Compound (VII) can be purified by column chromatography to provide compound (VII) with purity greater than 95%.

Process to Prepare a Compound of Formula (II)

The current invention also includes a process for preparing a compound of formula (II) starting with the compound (VI) as shown in Scheme 7.

Scheme 7

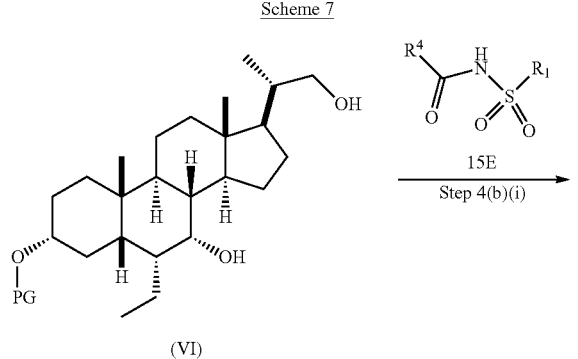

(VI)

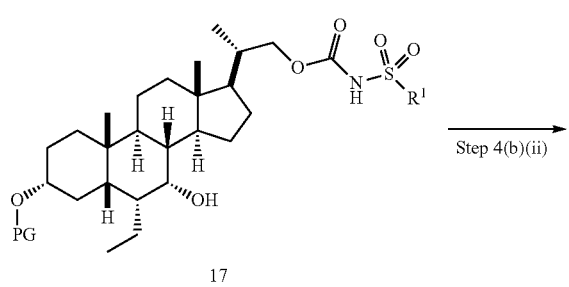

17

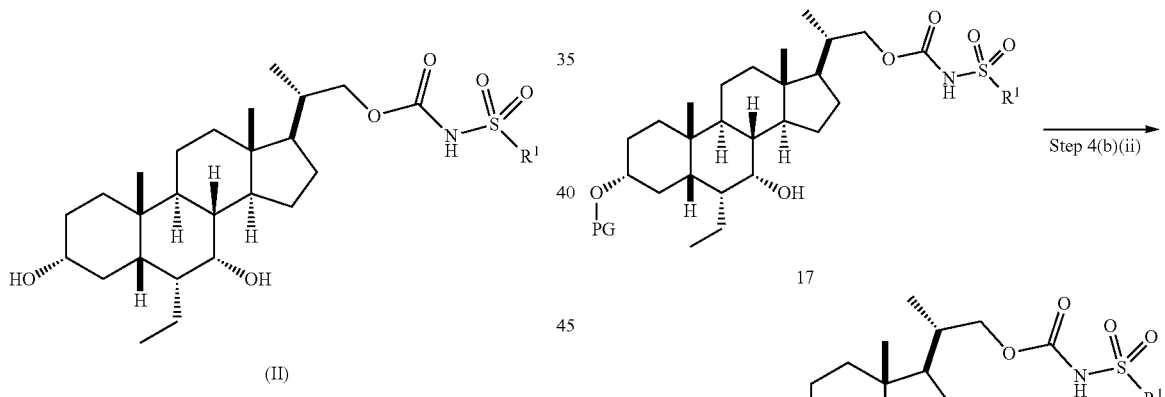

(II)

Step 4(b)(i), converting the compound (VI) to compound of formula 17:

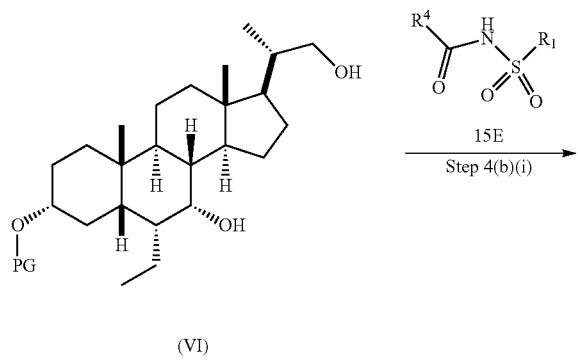

(VI)

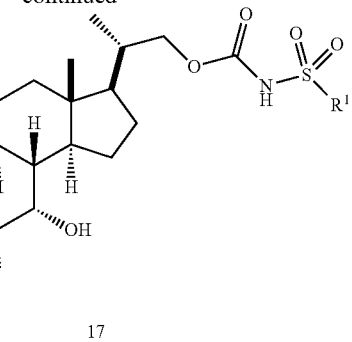

17 wherein $R^1$ and $R^4$ are as previously defined. Preferably $R^4$ in compound 15E is imidazol-1-yl, MeO—, EtO- or PhO—. More preferably, $R^4$ is PhO—.

The reaction is preferably carried in an aprotic solvent, such as, but not limited to, THF, DCM or toluene. In one preferred aspect, the reaction solvent is THF. Suitable organic bases include, but are not limited to, triethylamine, diisopropylethylamine, and DMAP. The reaction temperature preferably ranges from about 0° C. to about 80° C. In one aspect, the reaction is carried out at about 0° C. In another aspect, the reaction is carried out at about room temperature (about 25° C.). In yet another aspect, the reaction is carried out at about 50° C.

Step 4(b)(ii), converting compound of formula 17 to compound of Formula (II):

Step 4(b)(ii) is the removal of the PG protecting group of compound of formula 17 to form compound (II), wherein PG, and $R^1$ is as previously defined. The PG protecting group can be removed under suitable deprotection conditions as are known in the art. The preferred PG protecting group is the TBS, Preferably, the protecting group is removed by a deprotecting reagent such as, but not limited to, TBAF, or an acid such as HCl. Preferably compound of formula 17 is treated with an acid in a protic solvent. Preferably compound of formula 17 is treated with an acid, such as HCl, in a protic solvent such as, but not limited to, MeOH, EtOH, PrOH, H₂O, or a mixture of two. The preferred solvent is MeOH. The reaction can be carried out at a temperature ranging from −10° C. to 50° C. In a preferred aspect, the reaction temperature is from 0° C. to 30° C. In another preferred aspect, the reaction temperature is about 25° C.

Process to Prepare Compound (VIII)

The process of the current invention also includes a process of preparation of compound (VIII) starting from the compound (VI) following the process described in Scheme 8.

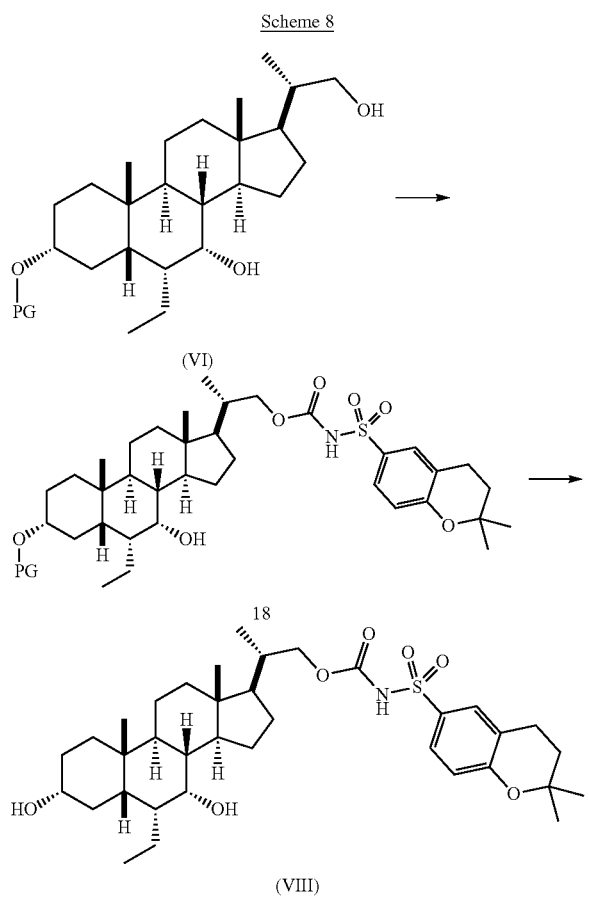

The process involves the conversion of alcohol compound (VI) to a sulfonyl carbamate compound 18, followed by deprotection to produce compound (VIII). The conditions for the process described for Scheme 8 are the same as were previously defined for Scheme 7.

The process involves the conversion of alcohol the compound (VI) to a sulfonyl carbamate 18 with an appropriate reagent (for example, selected from 15A-15D) in the presence of organic base.

In one aspect, the reagent is 15B which can be formed by reacting sulfonamide compound 15A with CDI.

In another aspect, the reagent can be sulfonylcarbamate compound 15C, wherein R⁵ is alkyl or aryl, preferably methyl, ethyl, or phenyl. The preferred reagent is 15D.

In one aspect, the alcohol compound (VI) reacts with 15D in an aprotic solvent, such as, but not limited to, THF, DCM or toluene. In one preferred aspect, the reaction solvent is THF. Suitable organic bases include, but are not limited to, triethylamine and diisopropylethylamine. DMAP, ranging from 1 mol % to 50 mol %, can be added to facilitate the reaction. The reaction temperature preferably ranges from about 0° C. to about 80° C. In one aspect, the reaction is carried out at about 0° C. In another aspect, the reaction is carried out at about room temperature (about 25° C.). In yet another aspect, the reaction is carried out at a 50° C. Compound 18 can be purified by column chromatography to provide compound 18 with purity greater than 95%.

In one aspect, compound 18 reacts with a deprotecting reagent such as, but not limited to, TBAF, or an acid such as HCl. Preferably compound 18 is treated with an acid in a protic solvent. Preferably compound 18 is treated with an acid, such as HCl, in a protic solvent such as, but not limited to, MeOH, EtOH, i-PrOH, H₂O, or a mixture of two. The preferred solvent is MeOH. The reaction can be carried out at a temperature ranging from −10° C. to 50° C. In a preferred aspect, the reaction temperature is from 0° C. to 30° C. In another preferred aspect, the reaction temperature is about 25° C. Compound (VIII) can be purified by column chromatography to provide compound (VIII) with purity greater than 95%.

Process to Prepare Compound (IX)

The process of the current invention also includes a process of preparation of compound (IX) starting from the compound (VI) following the process described in Scheme 9.

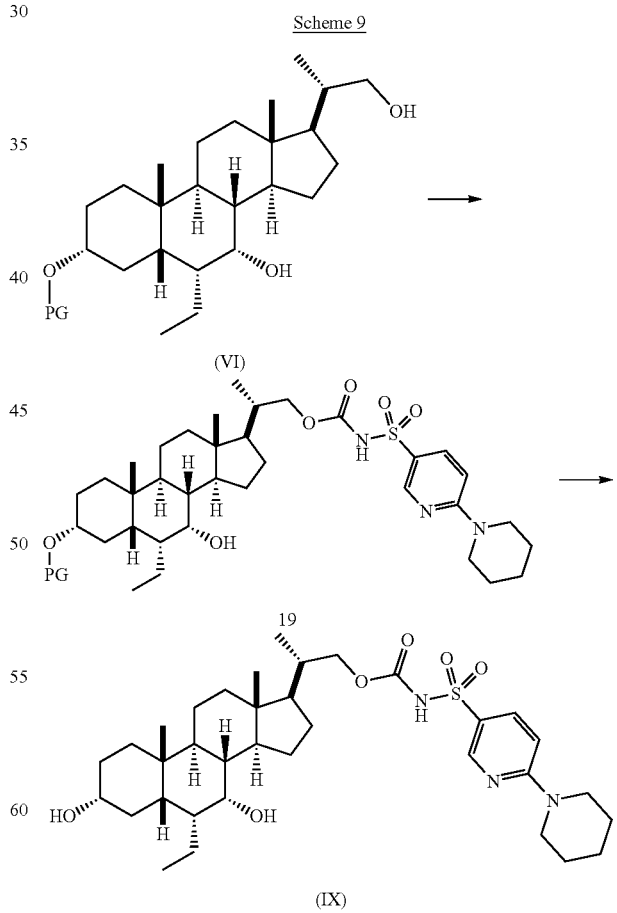

The process involves the conversion of alcohol the compound (VI) or compound (VIb) to a sulfonyl carbamate compound (19) with an appropriate reagent, for example one of compounds 20A, 20B, 20C or 20D, in the presence of organic base.

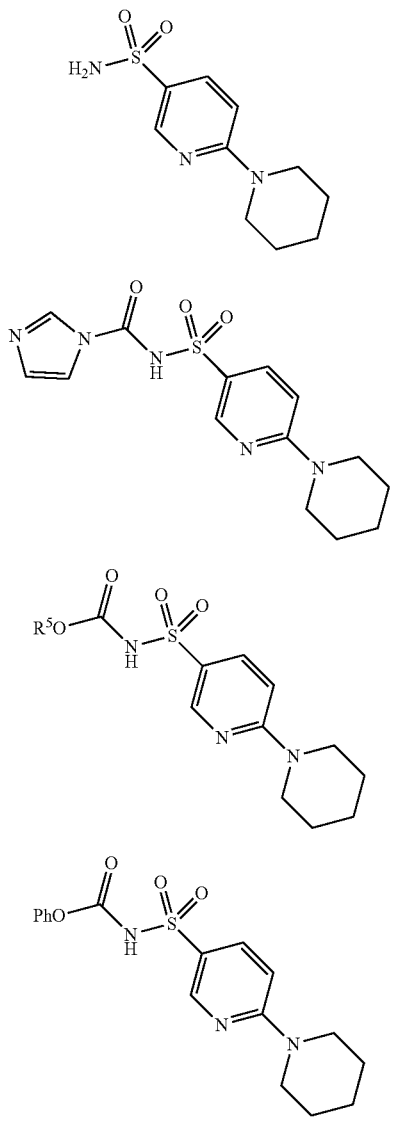

20A

20B

20C

20D

In one aspect, the reagent is 20B which can be formed by reacting sulfonamide compound 20A with CDI.

In another aspect, the reagent can be sulfonylcarbamate compound 20C, wherein $R^5$ is alkyl or aryl, preferably methyl, ethyl, or phenyl. The preferred reagent is 20D.

In one aspect, the alcohol the compound (VI) reacts with 20D in an aprotic solvent, such as, but not limited to, THF, DCM or toluene. In one preferred aspect, the reaction solvent is THF. Suitable organic bases include, but are not limited to, triethylamine, diisopropylethylamine, and DMAP. The reaction temperature preferably ranges from about 0° C. to about 80° C. In one aspect, the reaction is carried out at about 0° C. In another aspect, the reaction is carried out at about room temperature (about 25° C.). In yet another aspect, the reaction is carried out at a 50° C. Compound 19 can be purified by column chromatography to provide compound 19 with purity greater than 95%.

In one aspect, compound 19 reacts with a deprotecting reagent such as, but not limited to, TBAF, or an acid such as HCl. Preferably compound 19 is treated with an acid in a protic solvent. Preferably compound 19 is treated with an acid, such as HCl, in a protic solvent such as, but not limited to, MeOH, EtOH, i-PrOH, H$_2$O, or a mixture of two. The preferred solvent is MeOH. The reaction can be carried out at a temperature ranging from −10° C. to 50° C. In a preferred aspect, the reaction temperature is from 0° C. to 30° C. In another preferred aspect, the reaction temperature is about 25° C. Compound (IX) can be purified by column chromatography to provide compound (IX) with purity greater than 95%.

In another embodiment, the current invention also includes a process for preparing a compound of formula (II) starting with the compound (VIb) as shown in Scheme 10, and preparing compound (VIb) is as shown in Scheme 11.

Scheme 10

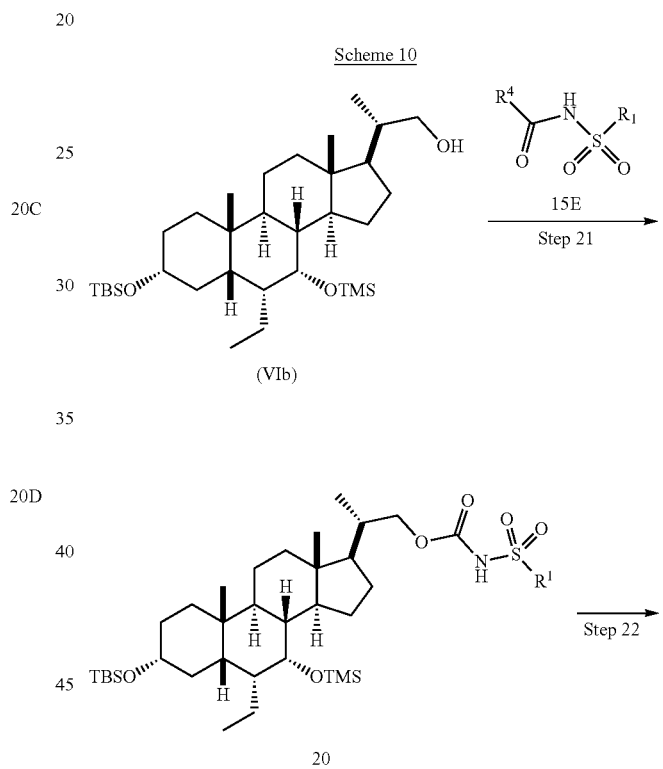

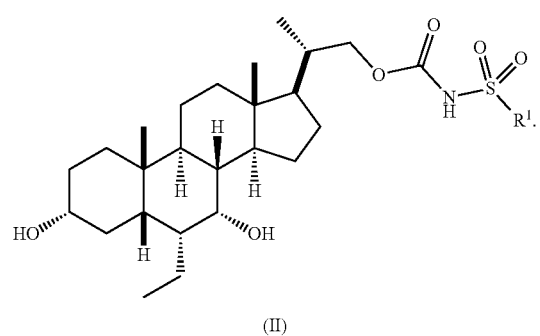

43

Scheme 11

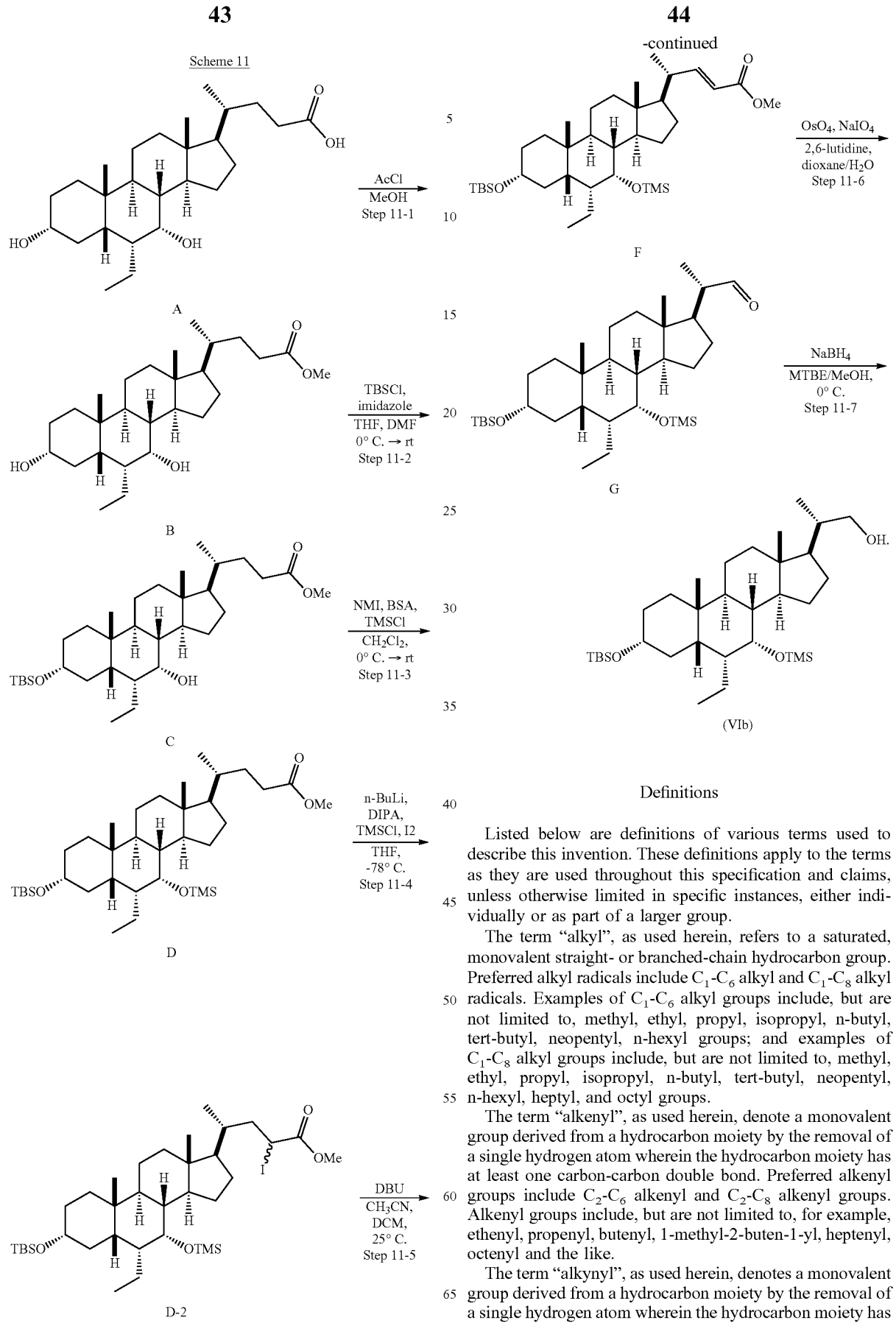

44

Definitions

Listed below are definitions of various terms used to describe this invention. These definitions apply to the terms as they are used throughout this specification and claims, unless otherwise limited in specific instances, either individually or as part of a larger group.

The term "alkyl", as used herein, refers to a saturated, monovalent straight- or branched-chain hydrocarbon group. Preferred alkyl radicals include $C_1$-$C_6$ alkyl and $C_1$-$C_8$ alkyl radicals. Examples of $C_1$-$C_6$ alkyl groups include, but are not limited to, methyl, ethyl, propyl, isopropyl, n-butyl, tert-butyl, neopentyl, n-hexyl groups; and examples of $C_1$-$C_8$ alkyl groups include, but are not limited to, methyl, ethyl, propyl, isopropyl, n-butyl, tert-butyl, neopentyl, n-hexyl, heptyl, and octyl groups.

The term "alkenyl", as used herein, denote a monovalent group derived from a hydrocarbon moiety by the removal of a single hydrogen atom wherein the hydrocarbon moiety has at least one carbon-carbon double bond. Preferred alkenyl groups include $C_2$-$C_6$ alkenyl and $C_2$-$C_8$ alkenyl groups. Alkenyl groups include, but are not limited to, for example, ethenyl, propenyl, butenyl, 1-methyl-2-buten-1-yl, heptenyl, octenyl and the like.

The term "alkynyl", as used herein, denotes a monovalent group derived from a hydrocarbon moiety by the removal of a single hydrogen atom wherein the hydrocarbon moiety has at least one carbon-carbon triple bond. Preferred alkynyl groups include $C_2$-$C_6$ alkynyl and $C_2$-$C_8$ alkynyl groups. Representative alkynyl groups include, but are not limited to, for example, ethynyl, 1-propynyl, 1-butynyl, heptynyl, octynyl and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic double bond. Preferred cycloalkyl groups include $C_3$-$C_8$ cycloalkyl and $C_3$-$C_{12}$ cycloalkyl groups. Examples of $C_3$-$C_8$-cycloalkyl include, but are not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, cyclooctyl, bicyclo[2.2.1]heptyl, bicyclo[2.2.2]octyl, spiro[2.5]octyl, 3-methylenebicyclo[3.2.1]octyl, spiro[4.4]nonanyl, bicycle[3.1.0]hexanyl, spiro[2.3]hexanyl, bicycle[3.1.1]heptanyl, spiro[2.5]octanyl, bicycle[4.1.0]heptanyl, bicycle[3.1.0]hexan-6-yl, spiro[2.3]hexan-5-yl, bicycle[3.1.1]heptan-3-yl, spiro[2.5]octan-4-yl, and bicycle[4.1.0]heptan-3-yl and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic double bond. Preferred cycloalkenyl groups include $C_3$-$C_8$ cycloalkenyl and $C_3$-$C_{12}$ cycloalkenyl groups. Examples of $C_3$-$C_8$-cycloalkenyl include, but are not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

The terms "heterocyclic" or "heterocycloalkyl" can be used interchangeably and referred to a non-aromatic ring or a bi- or tri-cyclic group fused, bridged or spiro system, wherein (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "arylalkyl," as used herein, refers to a functional group wherein an alkylene chain is attached to an aryl group, e.g., —$CH_2CH_2$-phenyl. The term "substituted arylalkyl" means an arylalkyl functional group in which the aryl group is substituted. Examples include, but are not limited to, benzyl, phenethyl and the like. Preferred arylalkyl groups include aryl-$C_1$-$C_8$-alkyl groups.

The term "heteroaryl," as used herein, refers to a mono-, bi-, or tri-cyclic group comprising at least one 5- or 6-membered aromatic ring comprising at least one ring atom selected from S, O and N. Preferred heteroaryl groups are monocyclic or bicyclic. Heteroaryl groups include monocyclic groups having 5 or 6 ring atoms and fused bicyclic groups comprising 8 to 10 ring atoms. Heteroaryl groups include, but are not limited to, pyridinyl, pyrazolyl, pyrazinyl, pyrimidinyl, pyrrolyl, pyrazolyl, imidazolyl, thiazolyl, thienyl, triazolyl, isothiazolyl, oxazolyl, isoxazolyl, thiadiazolyl, oxadiazolyl, thiophenyl, furanyl, quinolinyl, isoquinolinyl, benzimidazolyl, benzooxazolyl, benzothienyl, quinoxalyl, indolyl, indazolyl, benzisoxazolyl, benzofuranyl, benzotriazolyl, benzothiazolyl, and the like.

The term "heteroarylalkyl," as used herein, refers to an alkylene chain is attached to a heteroaryl group. The tem "substituted heteroarylalkyl" means a heteroarylalkyl functional group in which the heteroaryl group is substituted. Examples include, but are not limited to, pyridinylmethyl, pyrimidinylethyl and the like. Preferred heteroarylalkyl groups include heteroaryl-$C_1$-$C_8$-alkyl groups.

The term "biaryl", as used herein, refers to a moiety consisting of two aryl groups, two heteroaryl groups or an aryl group and a heteroaryl group, wherein the two groups are connected by a single bond. A substituted biaryl group is a biaryl moiety in which at least one of the connected groups has at least one non-hydrogen substituent. Examples of biaryl groups include biphenyl, pyridylphenyl, pyrimidylphenyl, pyrimidypyridyl, and pyrimidyloxadizolyl groups.

The term 'aryl-heterocyclyl" refers to a bicyclic group comprising a monocyclic aryl or heteroaryl group connected to a heterocyclic group by a single bond. Examples of aryl-heterocyclyl groups include phenyl-piperidinyl and pyridyl-piperidinyl groups.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, protected hydroxy, —$NO_2$, —$N_3$, —CN, —$NH_2$, protected amino, oxo, thioxo, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)— heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_2$-$C_8$-alkenyl, —$OCO_2$—$C_2$-$C_8$-alkynyl, —OCO$_2$—C$_3$-C$_{12}$-cycloalkyl, —OCO$_2$-aryl, —OCO$_2$-heteroaryl, —OCO$_2$-heterocycloalkyl, —OO$_2$—C$_1$-C$_{12}$ alkyl, —OCO$_2$—C$_2$-C$_8$ alkenyl, —OCO$_2$—C$_2$-C$_8$ alkynyl, CO$_2$—C$_3$-C$_{12}$-cycloalkyl, —CO$_2$— aryl, CO$_2$-heteroaryl, CO$_2$-heterocyloalkyl, —OCONH$_2$, —OCONH—C$_1$-C$_{12}$-alkyl, —OCONH—C$_2$-C$_8$-alkenyl, —OCONH—C$_2$-C$_8$-alkynyl, —OCONH—C$_3$-C$_{12}$-cycloalkyl, —OCONH-aryl, —OCONH-heteroaryl, —OCONH— heterocyclo-alkyl, —NHC(O)H, —NHC(O)—C$_1$-C$_{12}$-alkyl, —NHC(O)—C$_2$-C$_8$-alkenyl, —NHC(O)—C$_2$-C$_8$-alkynyl, —NHC(O)—C$_3$-C$_{12}$-cycloalkyl, —NHC(O)-aryl, —NHC(O)-heteroaryl, —NHC(O)-heterocyclo-alkyl, —NHCO$_2$—C$_1$-C$_{12}$-alkyl, —NHCO$_2$—C$_2$-C$_8$-alkenyl, —NHCO$_2$— C$_2$-C$_8$-alkynyl, —NHCO$_2$—C$_3$-C$_{12}$-cycloalkyl, —NHCO$_2$-aryl, —NHCO$_2$-heteroaryl, —NHCO$_2$— heterocycloalkyl, —NHC(O)NH$_2$, —NHC(O)NH—C$_1$-C$_{12}$-alkyl, —NHC(O)NH—C$_2$-C$_8$-alkenyl, —NHC(O)NH—C$_2$-C$_8$-alkynyl, —NHC(O)NH—C$_3$-C$_{12}$-cycloalkyl, —NHC(O)NH-aryl, —NHC(O)NH-heteroaryl, —NHC(O)NH— heterocycloalkyl, NHC(S)NH$_2$, —NHC(S)NH—C$_1$-C$_{12}$-alkyl, —NHC(S)NH—C$_2$-C$_8$-alkenyl, —NHC(S)NH—C$_2$-C$_8$-alkynyl, —NHC(S)NH—C$_3$-C$_{12}$-cycloalkyl, —NHC(S)NH-aryl, —NHC(S)NH— heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_8$-alkenyl, —NHC(NH)NH—C$_2$-C$_8$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_8$-alkenyl, —NHC(NH)—C$_2$-C$_8$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_8$-alkenyl, —C(NH)NH—C$_2$-C$_8$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_8$-alkenyl, —S(O)—C$_2$-C$_8$-alkynyl, —S(O)—C$_3$-C$_{12}$-cycloalkyl, —S(O)-aryl, —S(O)-heteroaryl, —S(O)-heterocycloalkyl, —SO$_2$NH$_2$, —SO$_2$NH—C$_1$-C$_{12}$-alkyl, —SO$_2$NH—C$_2$-C$_8$-alkenyl, —SO$_2$NH—C$_2$-C$_8$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_8$-alkenyl, —NHSO$_2$—C$_2$-C$_8$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_8$-alkenyl, —S—C$_2$-C$_8$-alkynyl, —S—C$_3$-C$_{12}$-cycloalkyl, —S-aryl, —S-heteroaryl, —S— heterocycloalkyl, or methylthio-methyl. It is understood that the aryls, heteroaryls, alkyls, cycloalkyls and the like can be further substituted. In some cases, each substituent in a substituted moiety is additionally optionally substituted with one or more groups, each group being independently selected from —F, —Cl, —Br, —I, —OH, —NO$_2$, —CN, or —NH$_2$.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic," as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl. Such alicyclic groups may be further substituted.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycoaklylene, cycloalkenylene, cycloalkynylene, arylalkylene, heteroarylalkylene and heterocycloalkylene groups are to be included in the above definitions, and are applicable to provide the Formulas herein with proper valency.

The term "hydroxyl protecting agent", as used herein, is a compound represented by PG-X, PG$^1$-X or PG$^3$-X, where PG, PG$^1$ and PG$^3$ are as defined herein and X is a suitable leaving group, preferably a halogen, an alkyl sulfonate or a fluoroalkylsulfonate. Preferably, X is Cl, Br, I, or triflate (OTf). A hydroxyl protecting agent wherein PG, PG$^1$ or PG$^3$ is a silyl group is alternatively referred to herein as a "silylating agent".

The terms "halo" and "halogen," as used herein, refer to an atom selected from fluorine, chlorine, bromine and iodine.

The term "hydrogen" includes hydrogen and deuterium. In addition, the recitation of an atom includes other isotopes of that atom so long as the resulting compound is pharmaceutically acceptable.

The term "hydroxyl protecting group," as used herein, refers to a labile chemical moiety which is known in the art to protect a hydroxyl group against undesired reactions during synthetic procedures. After said synthetic procedure(s) the hydroxyl protecting group as described herein may be selectively removed. Hydroxyl protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxyl," as used herein, refers to a hydroxyl group protected with a hydroxyl protecting group, as defined above, including benzoyl, acetyl, trimethylsilyl, triethylsilyl, methoxymethyl groups, for example.

When the compounds described herein contain one or more asymmetric centers they give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus, a carbon-carbon double bond depicted arbitrarily herein as trans may be cis, trans, or a mixture of the two in any proportion.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Berge, et al. describes pharmaceutically acceptable salts in detail in J. Pharmaceutical Sciences, 66: 1-19 (1977). The salts can be prepared in situ during the final isolation and purification of the compounds of the invention, or separately by reaction of the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

The term "treating", as used herein, means relieving, lessening, reducing, eliminating, modulating, or ameliorating, i.e., causing regression of the disease state or condition. Treating can also include inhibiting, i.e., arresting the development, of an existing disease state or condition, and relieving or ameliorating, i.e., causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "Lewis acid" refers to a substance that accepts an electron pair from a base, forming a covalent bond with the base. Also defined in literature such as "Advanced Organic Chemistry" Jerry March, 4th edition, published by Wiely Interscience.

"Solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired isoxazole products of the present invention. Synthetic chemistry transformations and protecting group methodologies (protection and deprotection) useful in synthesizing the compounds described herein include, for example, those described in R. Larock, *Comprehensive Organic Transformations,* VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Abbreviations

Abbreviations which have been used in the descriptions of the schemes and the examples that follow are:
Ac for acetyl;
AcOH for acetic acid;
ACN for acetonitrile;
aq. for aqueous;
BA for bile acid;
Brine for sodium chloride solution in water;
n-BuLi for n-butyl lithium;
cAMP for cyclic adenosine monophosphate;
CDCA for chenodeoxycholic acid;
CDI for carbonyldiimidazole;
CTX for cerebrotendinous xanthomatosis;
D2 for type 2 iodothyronine deiodinase;
DABCO for 1,4-diazabicyclo[2.2.2]octane;
DBN for 1,5-Diazabicyclo[4.3.0]non-5-ene;
DBU for 1,8-diazabicyclo[5.4.0]undec-7-ene;
DCM for dichloromethane;
DIBAL for diisobutylaluminium hydride;
DIPEA or (i-Pr)$_2$EtN for N,N-diisopropylethyl amine;
Dess-Martin periodinane for 1,1,1-tris(acetyloxy)-1,1-dihydro-1,2-benziodoxol-3-(1H)-one;
DMAP for 4-dimethylamino-pyridine;
DMF for N,N-dimethylformamide;
DMSO for dimethyl sulfoxide;
DPPA for diphenyl phosphoryl azide;
EtOAc for ethyl acetate;
EtOH for ethanol;
Et$_2$O for diethyl ether;
eq. for equivalent;
FXR for farnesoid x receptor;
GLP-1 for glucagon-like peptide 1
hrs for hours;
IBX for 2-iodoxybenzoic acid;
KHMDS for potassium bis(trimethylsilyl)amide;
KLCA for 7-ketolithocholic acid;
OTf or triflate for trifluoromethanesulfonate;
Ph for phenyl;
LDA for lithium diisopropylamide;
LiHMDS for lithium bis(trimethylsilyl)amide;
min for minutes;
MOM for methoxymethyl;
MEM for methoxyethoxymethyl;
NAFLD for nonalcoholic fatty liver disease;
NaHMDS for sodium bis(trimethylsilyl)amide;
NASH for nonalcoholic steatohepatitis;
NBS for N-bromosuccinimide;
NIS for N-iodosuccinimide;
NMO for N-methylmorpholine N-oxide;
o/n for overnight;
PBC for primary biliary cirrhosis;
PCC for pyridinium chlorochromate;
PDC for pyridinium dichromate;
Pd/C for palladium on carbon;
PNAC for parenteral nutrition associated cholestasis;
PSC for primary sclerosing cholangitis;
i-PrOAc for isopropyl acetate;
psi for pounds per square inch;
rt for room temperature;
sat. for saturated;
SEM for 2-trimethylsilylethoxymethyl;
TBAF for tetrabutylammonium fluoride;
TBDPS: for tert-butyl diphenylsilyl;
TBS for tert-butyl dimethylsilyl;
TEA or Et$_3$N for triethylamine;
TES for triethylsilyl;
TFA or CF$_3$COOH for trifluoroacetic acid;
THF for tetrahydrofuran;
THP for tetrahydropyranyl;
TIPS for triisopropylsilyl;
TMS for trimethylsilyl;
TMSCl for trimethylsilyl chloride;
TMSOTf for trimethylsilyl trifluoromethanesulfonate;
TBME or MTBE for tert-butyl methyl ether;
TLC for thin layer chromatography.

All other abbreviations used herein, which are not specifically delineated above, shall be accorded the meaning which one of ordinary skill in the art would attach.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1. Preparation of Compound 2 from Compound 1

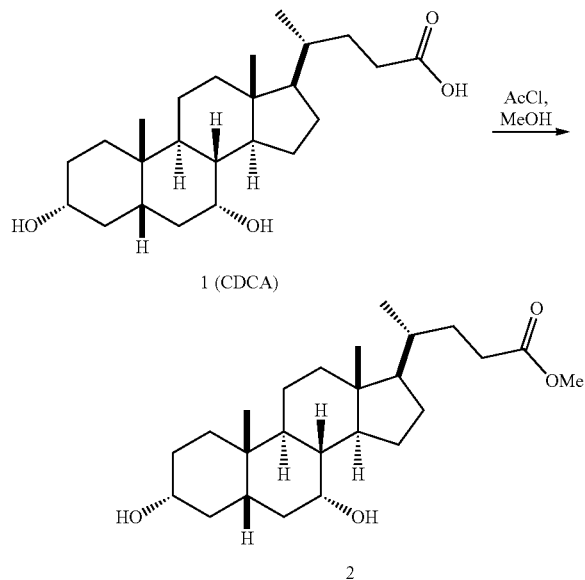

To a solution of compound 1 (101.2 g, 258 mmol, 1.0 eq) in MeOH (607 mL, 6 v) in a 2 L flask was charged acetyl chloride (2.0 g, 1.8 mL, 25.8 mmol, 0.1 eq) and the reaction was stirred for 18 h. The reaction was concentrated under reduced pressure and co-distilled with THF (2×300 mL). The resultant residue was dried under vacuum to give 105 g of crude compound 2 (HPLC purity: 99.6%) as a colorless amorphous solid containing THF. This material was used in the next step without further purification. $^1$H NMR (400 MHz, Chloroform-d) δ 3.84 (q, J=3.1 Hz, 1H), 3.65 (s, 3H), 3.45 (tt, J=11.1, 4.4 Hz, 1H), 2.34 (ddd, J=15.3, 10.1, 5.2 Hz, 1H), 2.28-2.13 (comp, 2H), 2.03-1.92 (comp, 3H), 1.87-1.76 (comp, 4H), 1.74-1.58 (comp, 5H), 1.55-1.04 (comp, 10H), 0.99 (dd, J=14.2, 3.4 Hz, 1H), 0.91 (d, J=6.4 Hz, 3H), 0.89 (s, 3H), 0.65 (s, 3H).

Example 2. Preparation of Compound 3 from Compound 2

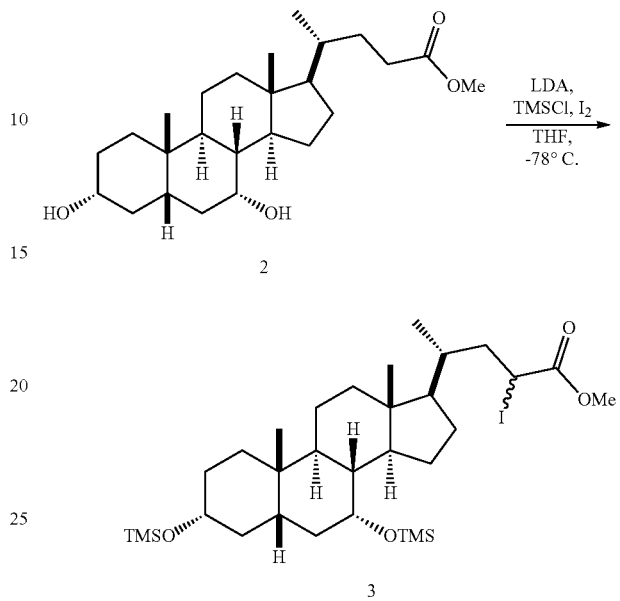

To a solution of diisopropylamine (53.5 g, 75.0 mL, 529 mmol, 4.1 eq) in anhydrous THF (143 mL, 2.7 v) at −78° C. was charged n-BuLi (206 mL of a 2.5M solution in hexanes, 516 mmol, 4.0 eq) dropwise. The reaction was stirred for 15 min at −78° C., whereupon TMSCl (84.0 g, 99.0 mL, 774 mmol, 6.0 eq) was added. A solution of compound 2 (52.5 g, 129 mmol, 1.0 eq) in anhydrous THF (322 mL, 6.2 v) was added dropwise at −78° C. The reaction was warmed to room temperature and stirred for 3 hrs. The reaction was cooled to −78° C. and a solution of $I_2$ (45.8 g, 181 mmol, 1.4 eq) in anhydrous THF (401 mL, 7.6 v) was added dropwise. The reaction was stirred for 0.5 hrs at −78° C. The reaction was poured into an aqueous 10% $NH_4Cl$ solution (600 mL) and diluted with MTBE (600 mL). The layers were separated and the aqueous layer was extracted with MTBE (2×300 mL). The combined organic layers were washed with an aqueous 10% $Na_2S_2O_3$ solution (2×400 mL), brine (400 mL), dried ($MgSO_4$), filtered, and concentrated to give 118 g crude compound 3 as a yellow gum. This material was used in the next step without further purification. Compound 3 was isolated as a ~1:1 mixture of diastereomers: $^1$H NMR (400 MHz, Chloroform-d) δ 4.48 (dd, J=12.3, 3.8 Hz, 0.5H), 4.37 (dd, J=11.2, 4.0 Hz, 0.5H), 3.79-3.72 (comp, 6H), 3.41 (tt, J=10.2, 4.5 Hz, 1H), 2.60-2.47 (m, 0.5H), 2.32 (q, J=13.1 Hz, 1H), 2.18 (ddd, J=14.4, 11.1, 2.7 Hz, 0.5H), 1.99-1.71 (comp, 6 H), 1.70-0.95 (comp, 14H), 0.92 (d, J=6.4 Hz, 1.5H), 0.89 (d, J=6.5 Hz, 1.5H), 0.86 (d, J=5.1 Hz, 3H), 0.67 (s, 1.5H), 0.59 (s, 1.5H), 0.16 (s, 9H), 0.10 (s, 9H).

Example 3. Preparation of Compound 4 from Compound 3

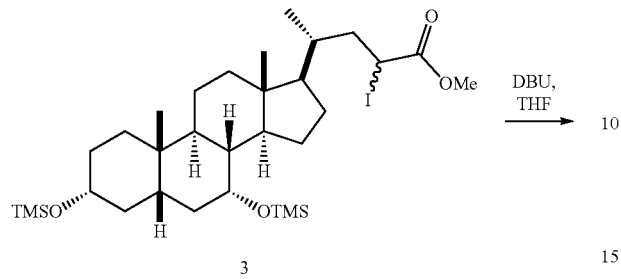

3

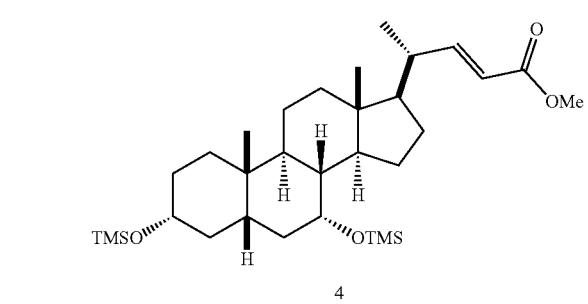

4

To a solution of crude compound 3 (87 g, 129 mmol, 1.0 eq) in anhydrous THF (1071 mL, 12.3 v) was charged DBU (58.7 g, 58.1 mL, 386 mmol, 3.0 eq) and the reaction was stirred for 48 hrs. The reaction was quenched with aqueous 10% NH$_4$C$_1$ (600 mL) and diluted with MTBE (600 mL). The layers were separated and the aqueous layer was extracted with MTBE (2×300 mL,). The combined organic layers were dried (MgSO$_4$), filtered, and concentrated to give 80 g crude compound 4 as a brown gum. This material was used in the next step without further purification. $^1$H NMR (400 MHz, Chloroform-d) δ 6.84 (dd, J=15.6, 9.0 Hz, 1H), 5.72 (d, J=15.6 Hz, 1H), 3.76 (qd, J=6.8, 6.0, 3.3 Hz, 1H), 3.71 (s, 3H), 3.40 (tt, J=10.8, 4.6 Hz, 1H), 2.39-2.18 (comp, 2H), 2.00-1.11 (m, 18H), 1.07 (d, J=6.6 Hz, 3H), 1.04-0.90 (comp, 2H), 0.86 (s, 3H), 0.65 (s, 3H), 0.10 (s, 9H), 0.07 (s, 9H).

Example 4. Preparation of Compound 5 from Compound 4

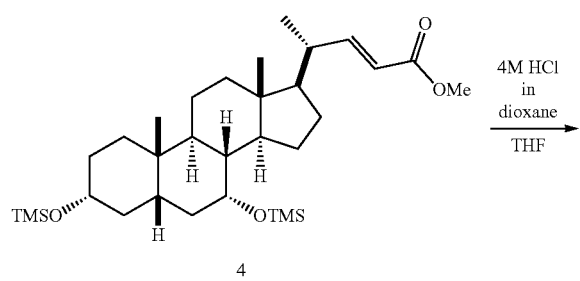

4

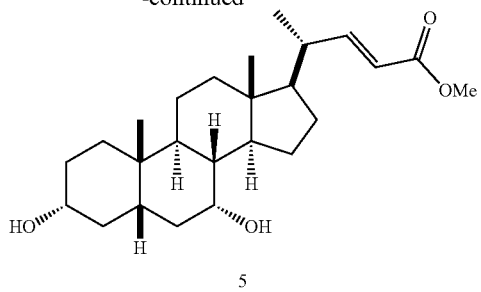

5

To a solution of crude compound 4 (70.6 g, 129 mmol, 1.0 eq) in anhydrous THF (334 mL, 4.7 v) was charged 4M HCl in 1,4-dioxane (33.4 mL, 0.47 v) and the reaction was stirred for 16 hrs. The reaction was concentrated under reduced pressure and co-distilled with DCM (1×400 mL). The resultant brown gum was purified by column chromatography eluting with hexanes/acetone (5% acetone 35% acetone, 2×330 g column) to give compound 5 (32.2 g, 80.0 mmol, 62% yield over 4 steps. $^1$H NMR (400 MHz, Chloroform-d) δ 6.83 (dd, J=15.6, 9.0 Hz, 1H), 5.73 (dd, J=15.6, 0.9 Hz, 1H), 3.84 (q, J=3.1 Hz, 1H), 3.71 (s, 3H), 3.51-3.40 (m, 1H), 2.33-2.13 (comp, 2H), 2.03-1.91 (comp, 2H), 1.91-1.78 (comp, 2H), 1.78-1.57 (comp, 4H), 1.55-1.11 (comp, 11H), 1.08 (d, J=6.6 Hz, 3H), 0.98 (td, J=14.1, 3.3 Hz, 1H), 0.90 (s, 3H), 0.69 (s, 3H).

Example 5. Preparation of Compound 6 from Compound 5

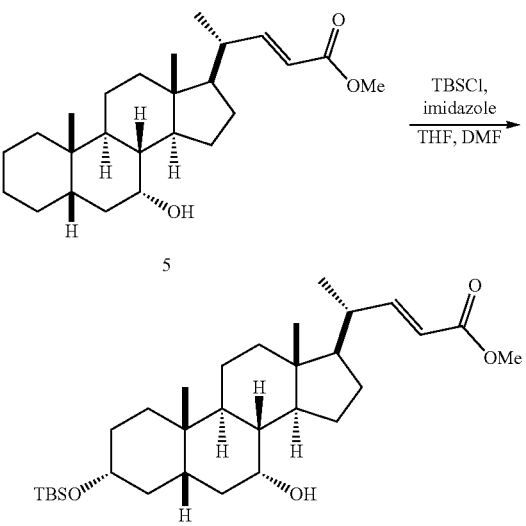

To a solution of compound 5 (32.2 g, 80.0 mmol, 1.0 eq) and imidazole (10.8 g, 159 mmol, 2.0 eq) in anhydrous THF (166 mL, 5.2 v) and DMF (33.2 mL, 1v) at 0° C. was charged TBSCl (13.2 g, 88.0 mmol, 1.2 eq). The reaction was warmed to room temperature and stirred for 3 hrs. Upon completion, the reaction was concentrated to remove most of the THF. Diluted with MTBE (300 mL) and H$_2$O (300 mL). The layers were separated and the organic layer was washed with aqueous 10% citric acid (150 mL), H$_2$O (150 mL), saturated aqueous NaHCO$_3$ (150 mL), H$_2$O (150 mL), and brine (150 mL). The organic layer was dried (MgSO$_4$), filtered, and concentrated to give crude compound 6 (44 g). as a colorless amorphous solid. This material was used in the next step without further purification. $^1$H NMR (500 MHz, Chloroform-d) δ 6.83 (dd, J=15.6, 9.0 Hz, 1H), 5.73 (d, J=15.5 Hz, 1H), 3.83-3.81 (m, 1H), 3.71 (s, 3H), 3.48-3.38 (m, 1H), 2.26 (td, J=8.8, 6.2 Hz, 1H), 2.19 (td, J=13.3, 11.1 Hz, 1H), 2.02-1.10 (comp, 19H), 1.08 (d, J=6.6 Hz, 3H), 0.98-0.91 (m, 1H), 0.89 (s, 3H), 0.87 (s, 9H), 0.68 (s, 3H), 0.04 (s, 6H).

Example 6. Preparation of Compound (III) from Compound 6

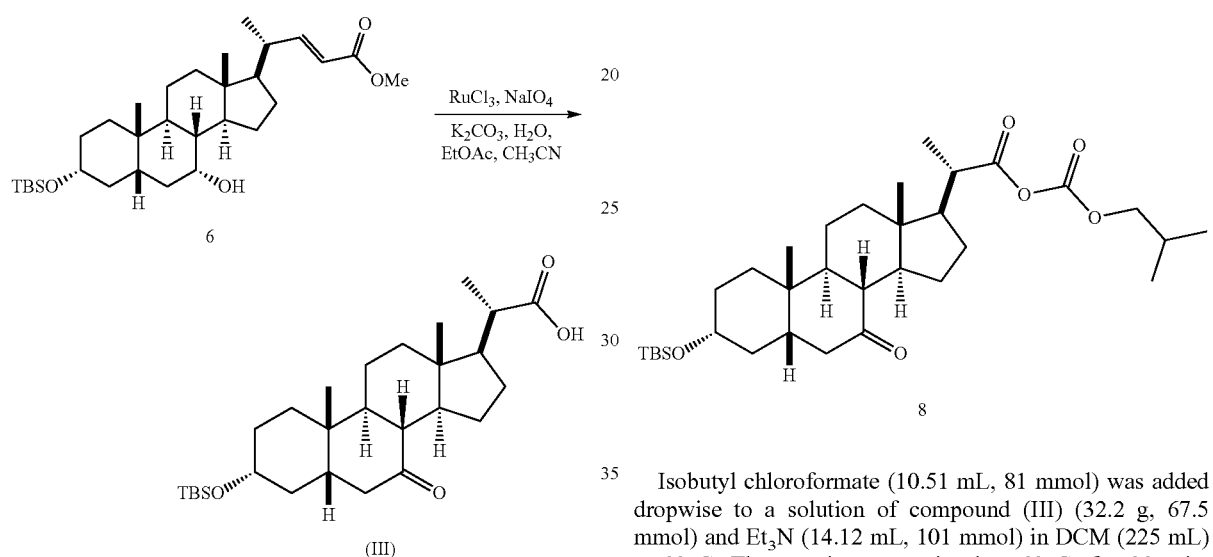

To a solution of compound 6 (41.3 g, 80.0 mmol, 1.0 eq) in EtOAc (227 mL, 5.4 v) and CH$_3$CN (227 mL, 5.4 v) was added a solution of K$_2$CO$_3$ (110 g, 796 mmol, 10.0 eq) in H$_2$O (341 mL, 8.3 v). RuCl$_3$ hydrate (0.90 g, 4.0 mmol, 0.05 eq) was added, followed by NaIO$_4$ (170 g, 796 mmol, 10.0 eq) and the reaction was stirred vigorously o/n until no starting material remains by HPLC. The reaction mixture was filtered and the solid was rinsed with EtOAc. The filtrate was quenched with aqueous 10% citric acid (600 mL). The layers were separated and the aqueous layer was extracted with EtOAc (250 mL). The combined organic layers were washed with water (2×400 mL), brine (400 mL), dried (Na$_2$SO$_4$) and concentrated to about 400 mL. About 400 mL of heptane was added and the mixture was concentrated under reduced pressure slowly at 38° C. to reduce the total volume to about 100 mL. The resultant mixture was cooled to room temperature and filtered to collect the solid, rinsing with hexanes. This crystallization procedure was repeated once to produce a second lot of material. In total compound (III) (12.0 g, 25.1 mmol, 76% yield) as a tan solid. $^1$H NMR (400 MHz, Chloroform-d) δ 3.56 (tt, J=10.4, 4.7 Hz, 1H), 2.82 (dd, J=12.3, 5.7 Hz, 1H), 2.45-2.39 (m, 1H), 2.39-2.32 (m, 1H), 2.27 (dtt, J=10.1, 7.2, 3.6 Hz, 1H), 1.99-1.75 (m, 5H), 1.67-1.25 (comp, 11H), 1.23 (d, J=6.8 Hz, 3H), 1.17 (s, 3H), 1.16-1.07 (m, 1H), 0.99 (qd, J=12.1, 6.3 Hz, 1H), 0.86 (s, 9H), 0.67 (s, 3H), 0.03 (s, 6H).

Example 7. Preparation of Compound 8 from Compound (III)

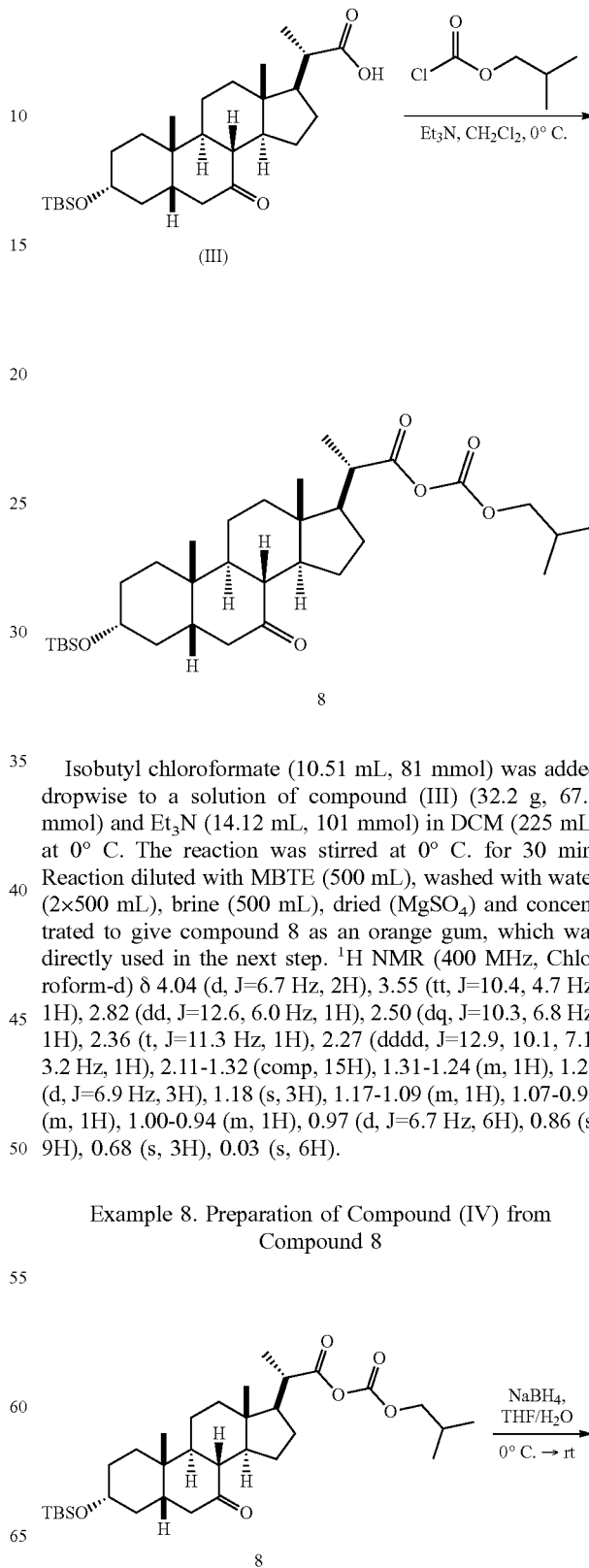

Isobutyl chloroformate (10.51 mL, 81 mmol) was added dropwise to a solution of compound (III) (32.2 g, 67.5 mmol) and Et$_3$N (14.12 mL, 101 mmol) in DCM (225 mL) at 0° C. The reaction was stirred at 0° C. for 30 min. Reaction diluted with MBTE (500 mL), washed with water (2×500 mL), brine (500 mL), dried (MgSO$_4$) and concentrated to give compound 8 as an orange gum, which was directly used in the next step. $^1$H NMR (400 MHz, Chloroform-d) δ 4.04 (d, J=6.7 Hz, 2H), 3.55 (tt, J=10.4, 4.7 Hz, 1H), 2.82 (dd, J=12.6, 6.0 Hz, 1H), 2.50 (dq, J=10.3, 6.8 Hz, 1H), 2.36 (t, J=11.3 Hz, 1H), 2.27 (dddd, J=12.9, 10.1, 7.1, 3.2 Hz, 1H), 2.11-1.32 (comp, 15H), 1.31-1.24 (m, 1H), 1.28 (d, J=6.9 Hz, 3H), 1.18 (s, 3H), 1.17-1.09 (m, 1H), 1.07-0.99 (m, 1H), 1.00-0.94 (m, 1H), 0.97 (d, J=6.7 Hz, 6H), 0.86 (s, 9H), 0.68 (s, 3H), 0.03 (s, 6H).

Example 8. Preparation of Compound (IV) from Compound 8

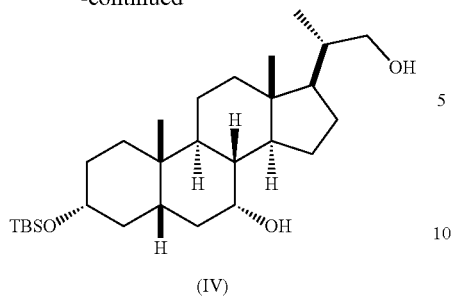

(IV)

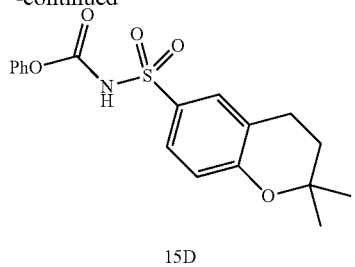

15D

NaBH$_4$ (5.11 g, 135 mmol) was added to a solution of compound 8 (38.9 g, 67.5 mmol) in THF (270 ml)/H$_2$O (67.5 ml) at 0° C. The reaction was stirred at 0° C. for 0.5 h and a second portion of NaBH$_4$ (5.11 g, 135 mmol) was added. The reaction was stirred overnight, warming slowly to rt. Reaction complete by TLC and HPLC. The reaction was cooled to 0° C., diluted with EtOAc (300 mL) and quenched with 10% citric acid (300 mL). The layers were separated and the aqueous layer extracted with EtOAc (2×150 mL). The combined organic layers were washed with brine (300 mL), dried (MgSO$_4$), filtered, and concentrated to give the crude product which was purified by column chromatography eluting with hexanes/acetone (0% acetone→25% acetone, 330 g column) to give compound (IV) (26.2 g, 56.4 mmol, 84% yield) as a colorless amorphous solid. $^1$H NMR (400 MHz, Chloroform-d) δ 3.83 (q, J=3.1 Hz, 1H), 3.64 (dd, J=10.4, 3.3 Hz, 1H), 3.48-3.38 (m, 1H), 3.35 (dd, J=10.5, 7.1 Hz, 1H), 2.19 (td, J=13.3, 11.0 Hz, 1H), 2.03-1.73 (comp, 5H), 1.72-1.08 (comp, 15H), 1.04 (d, J=6.6 Hz, 3H), 0.94 (td, J=14.5, 3.3 Hz, 1H), 0.89 (s, 3H), 0.88 (s, 9H), 0.67 (s, 3H), 0.04 (s, 6H).

Example 9. Synthesis of Compound 15D

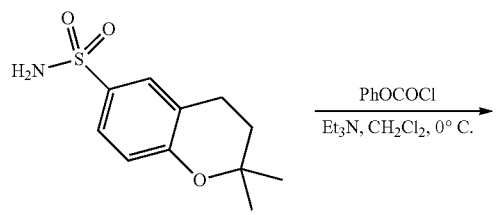

To a suspension of 2,2-dimethylchromane-6-sulfonamide (65 g, 269 mmol, 1.0 eq) and Et$_3$N (82 g, 113 mL, 808 mmol, 3.0 eq) in anhydrous CH$_2$Cl$_2$ (673 mL, 10 v) at 0° C. was charged PhOCOCl (50.6 g, 40.6 mL, 323 mmol, 1.2 eq). The reaction was stirred at 0° C. for 3 hrs. Upon completion, the reaction was diluted with CH$_2$Cl$_2$ (400 mL). The mixture was washed with cold H$_2$O (1000 mL), cold aqueous 10% citric acid (2×500 mL), and brine (1000 mL). The organic layer was dried (Na$_2$SO$_4$), filtered, and concentrated to about 500 mL total volume. Hexanes (500 mL) was added and the solution was concentrated to about 250 mL total volume. The mixture was cooled to rt. The resultant precipitate was collected by filtration, rinsing with hexanes (3×100 mL), and dried under vacuum to give compound 15D (72.5 g, HPLC, ELSD purity: 98.8%, HPLC UV$_{240}$ purity: 85.7%) as a tan solid. $^1$H NMR (400 MHz, Chloroform-d) δ 7.85-7.74 (m, 2H), 7.58 (s, 1H), 7.40-7.29 (m, 2H), 7.27-7.18 (m, 1H), 7.11-7.02 (m, 2H), 6.86 (t, J=8.6 Hz, 1H), 2.82 (t, J=6.7 Hz, 2H), 1.84 (t, J=6.7 Hz, 2H), 1.36 (d, J=2.1 Hz, 6H).

Example 10. Preparation of Compound 17 from Compound (IV)

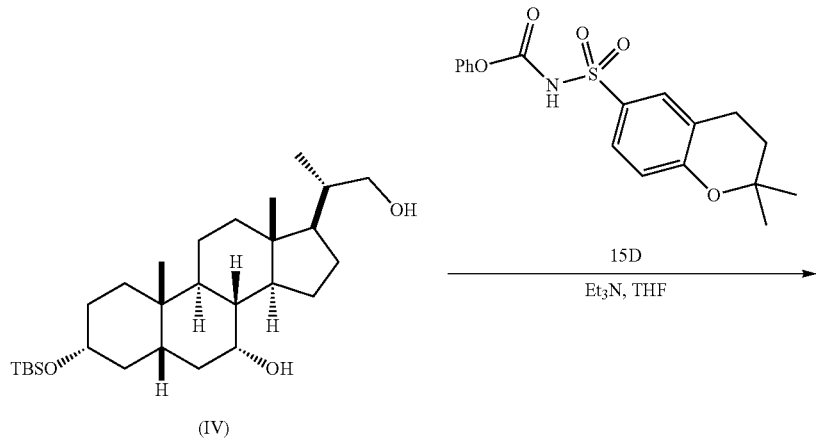

(IV)

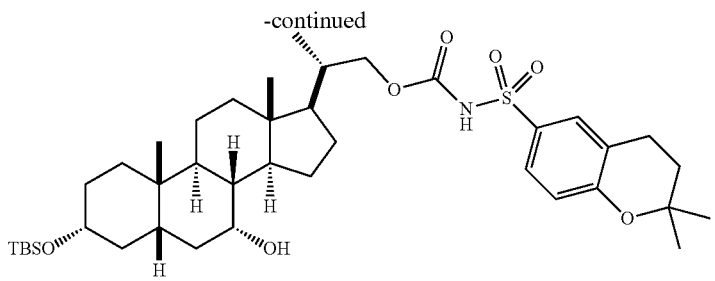

17

Compound 15D (17.46 g, 48.3 mmol) was added to a solution of compound (IV) (21.8 g, 46.9 mmol) and triethylamine (19.61 ml, 141 mmol) in dry THF (188 mL) at rt. The reaction mixture started at a clear solution. After about a hour, lots of solid precipitation formed. After stirring at rt for ~2 hours, the reaction mixture was diluted with MTBE (150 mL) and stirred at 35° C. for ~45 mins to allow the solid precipitate to age. Then the slurry mixture was concentrated slowly under reduced vacuum to remove ~80 mL of the solvent. The remaining solution with solid precipitate was cooled down to rt slowly and aged overnight. The solid was then collected by filtration, rinsed with MTBE, and dried under high vacuum to provide ~30 g of nice solid compound 17 as the NEt₃ salt form. The obtained compound 17, NEt₃ salt (~30 g) was partitioned in EtOAc 500 mL/10% citric acid (300 mL). The organic layer was separated and washed with water, sat. NaHCO₃, brine dried and concentrated to afford compound 17 (27.7 g, 87% yield). $^1$H NMR (400 MHz, Chloroform-d) δ 7.75-7.64 (m, 2H), 7.36 (s, 1H), 6.82 (d, J=8.6 Hz, 1H), 4.08 (m, 1H), 3.81-3.68 (m, 2H), 3.39 (m, 1H), 2.79 (t, J=6.7 Hz, 2H), 2.14 (td, J=13.2, 11.1 Hz, 1H), 1.97-1.67 (m, 6H), 1.67-1.32 (m, 10H), 1.31 (s, 6H), 1.31-0.99 (m, 6H), 0.97-0.87 (m, 4H), 0.84 (s, 12H), 0.60 (s, 3H), 0.00 (s, 6H).

Example 11. Preparation of Compound (VII) from Compound 17

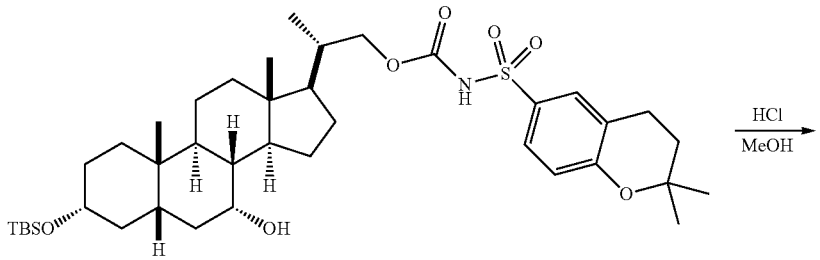

17

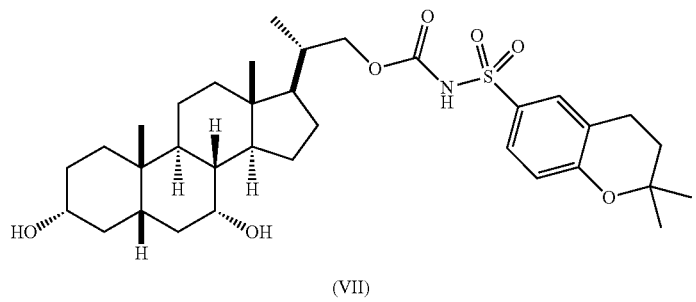

(VII)

A premixed solution of conc. HCl (294 mg, 2.98 mmol) in MeOH (5 mL) was added dropwise to a solution of compound 17 (21.84 g, 29.8 mmol) in MeOH (120 mL) at rt. The reaction was stirred at rt for ~30 min and monitored by TCL and HPCL. Upon completion, a solution of 50% NaOH (239 mg, 2.98 mmol) in water (1 mL) was added and the reaction mixture was concentrated to dryness. The crude solid was purified by silica gel chromatography with (220 g SiO2, 100% hexanes to 50% acetone/hexanes, product came out around 50% acetone/hexanes) to give compound (VII) (15 g, 81% yield). LC-MS (m/z, ES−): 616.33 [M−1]. $^1$H NMR (400 MHz, Chloroform-d) δ 7.79-7.68 (m, 2H), 7.32 (s, 1H), 6.87 (d, J=8.7 Hz, 1H), 4.12 (dd, J=10.5, 3.3 Hz, 1H), 3.87-3.74 (m, 2H), 3.48 (m, 1H), 2.83 (t, J=6.7 Hz, 2H), 2.28-2.13 (m, 1H), 2.04-1.89 (m, 2H), 1.88-1.79 (m, 4H), 1.78-1.59 (m, 4H), 1.55 (s, 3H), 1.48-1.36 (m, 3H), 1.36 (s, 6H), 1.37-1.23 (m, 3H), 1.25-1.06 (m, 3H), 1.05-0.92 (m, 4H), 0.90 (s, 3H), 0.65 (s, 3H).

Example 12. Preparation of Compound 9 from Compound (III)

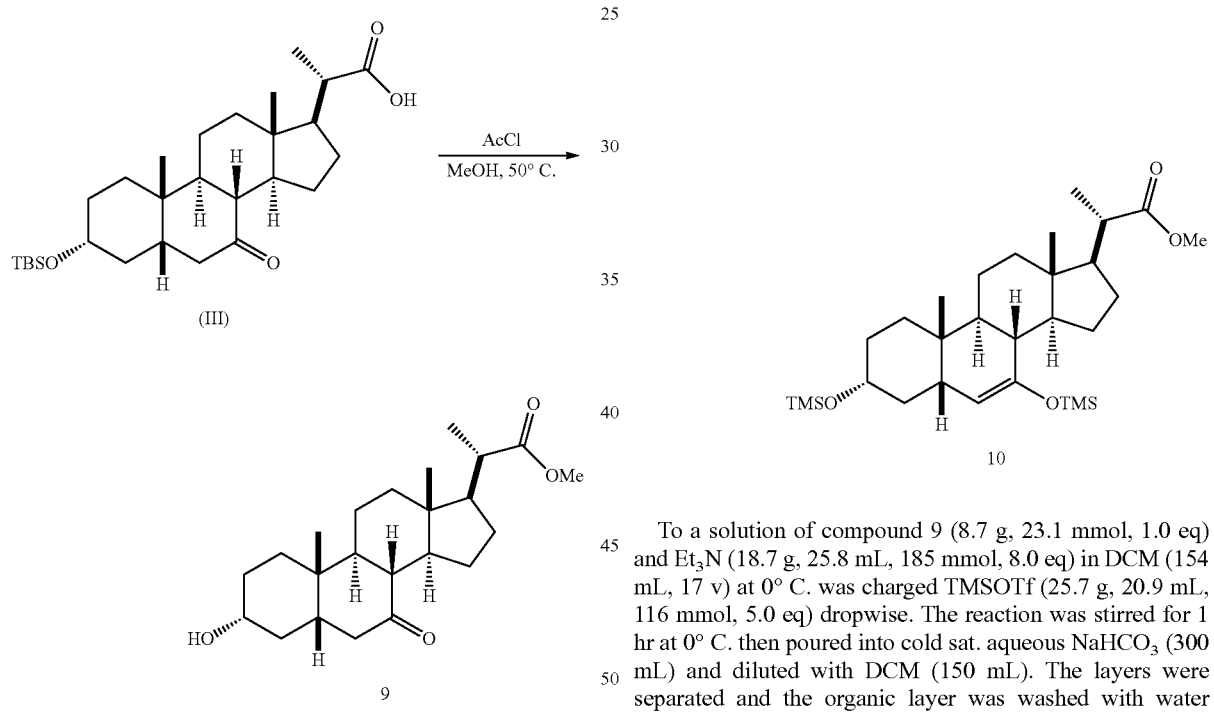

To a suspension of compound (III) (15.2 g, 31.9 mmol, 1.0 eq) in MeOH (91 mL, 6 v) at 0° C. was charged AcCl (12.5 g, 11.3 mL, 159 mmol, 5.0 eq) dropwise. The resulting solution was heated at 50° C. for 24 hrs. The reaction was concentrated and the resultant brown solid was partitioned between EtOAc (250 mL) and sat. aqueous NaHCO$_3$ (250 mL). The layers were separated and the organic layer was washed with H$_2$O (200 mL) and brine (200 mL). The organic layer was dried (MgSO$_4$), filtered, and concentrated to about 100 mL. Hexanes (150 mL) was added and the mixture concentrated at 40° C. to about 100 mL total volume. The resulting suspension was cooled to room temperature and allowed to age o/n. The precipitate was filtered, rinsing with hexanes, to give compound 9 (8.9 g, 23.6 mmol, 74% yield) as a colorless solid. $^1$H NMR (500 MHz, Chloroform-d) δ 3.65 (s, 3H), 3.67-3.58 (m, 1H), 2.85 (ddd, J=12.7, 6.1, 1.1 Hz, 1H), 2.48-2.33 (m, 2H), 2.22 (dddd, J=13.0, 10.2, 7.2, 3.3 Hz, 1H), 2.01-1.66 (m, 7H), 1.66-1.53 (m, 3H), 1.54-1.45 (m, 3H), 1.45-1.11 (m, 10H), 1.04-0.92 (m, 1H), 0.92-0.80 (m, 1H), 0.67 (s, 3H).

Example 13. Preparation of Compound 10 from Compound 9

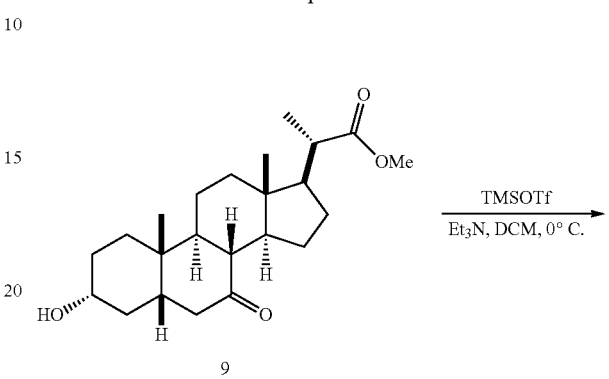

To a solution of compound 9 (8.7 g, 23.1 mmol, 1.0 eq) and Et$_3$N (18.7 g, 25.8 mL, 185 mmol, 8.0 eq) in DCM (154 mL, 17 v) at 0° C. was charged TMSOTf (25.7 g, 20.9 mL, 116 mmol, 5.0 eq) dropwise. The reaction was stirred for 1 hr at 0° C. then poured into cold sat. aqueous NaHCO$_3$ (300 mL) and diluted with DCM (150 mL). The layers were separated and the organic layer was washed with water (2×150 mL) and brine (150 mL), dried (MgSO$_4$), filtered, and concentrated under reduced pressure. The resultant residue was partitioned between hexanes (300 mL) and water (150 mL). The layers were separated and the organic layer was washed with brine (150 mL), dried (MgSO$_4$), filtered, and concentrated to give crude compound 10 (11.1 g) as a colorless amorphous solid. This material was used in the next step without further purification. The CDCl$_3$ used for H-NMR was be pre-treated with K$_2$CO$_3$ to avoid acid-mediated decomposition of compound 10. $^1$H NMR (400 MHz, Chloroform-d) δ 4.61 (dd, J=5.9, 1.9 Hz, 1H), 3.53 (s, 3H), 3.44-3.35 (m, 1H), 2.31 (dq, J=10.2, 6.9 Hz, 1H), 1.88-1.75 (m, 3H), 1.73-1.64 (m, 2H), 1.62-1.50 (m, 3H), 1.48-1.37 (m, 3H), 1.37-1.02 (m, 7H), 1.08 (d, J=6.8 Hz, 3H), 0.94 (td, J=14.2, 3.2 Hz, 1H), 0.72 (s, 3H), 0.58 (s, 3H), 0.04 (s, 9H), −0.00 (s, 9H).

Example 14. Preparation of Compound 11 from Compound 10

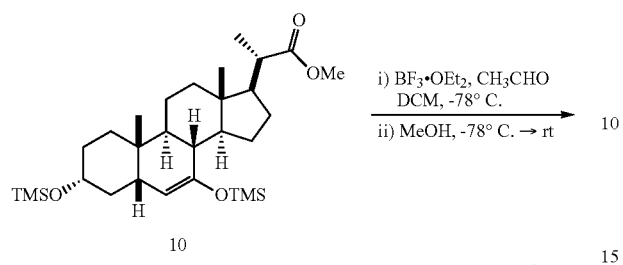

10

To a solution of compound 10 (11.1 g, 21.3 mmol, 1.0 eq) and acetaldehyde (2.3 g, 3.0 mL, 53.3 mmol, 2.5 eq) in DCM (107 mL, 10 v) at −78° C. was charged BF$_3$.OEt$_2$ (13.2 mL, 107 mmol, 5.0 eq) dropwise. The reaction was stirred at −78° C. for 4 hrs, whereupon MeOH (40 mL) was added dropwise. The reaction was warmed to room temperature and stirred o/n. The reaction was cooled to 0° C. and carefully quenched with aqueous sat. NaHCO$_3$ (250 mL) and diluted with DCM (150 mL). The layers were separated and the aqueous layer was extracted with DCM (1×150 mL). The combined organic layers were washed with brine (250 mL), dried (MgSO$_4$), filtered, and concentrated to give crude compound 11 (8.7 g, HPLC purity: 98.7%, mixture of E/Z isomers) as a yellow amorphous solid. This material was used in the next step without further purification. LC-MS (m/z, ES$^+$): 403.29 [M+H].

Example 15. Preparation of Compound 12 from Compound 11

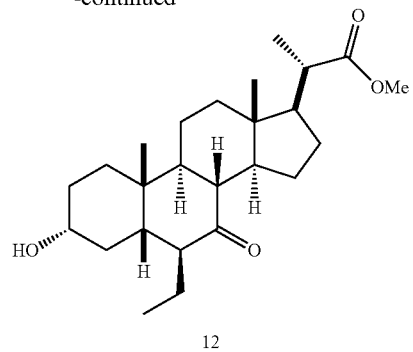

12

To a solution of crude compound 11 (8.6 g, 21.3 mmol, 1.0 eq) in MeOH (71 mL, 12.4 v) was charged 10% Pd/C (50% H$_2$O, 2.3 g, 0.25 wt). The reaction was evacuated and backfilled with H$_2$ (3×). The reaction was stirred for 72 hrs, diluted with EtOAc, and filtered through CELITE®. The filtrate was concentrated to give crude compound 12 (8.1 g, HPLC purity: 98.0%) as a colorless amorphous solid. This material was used in the next step without further purification. $^1$H NMR (400 MHz, Chloroform-d) δ 3.58 (s, 3H), 3.53-3.47 (m, 1H), 2.49 (dd, J=12.0, 10.7 Hz, 1H), 2.35 (dq, J=10.4, 6.8 Hz, 1H), 2.19-2.04 (m, 1H), 1.93-1.79 (m, 3H), 1.79-1.64 (m, 4H), 1.64-1.54 (m, 3H), 1.53-1.35 (m, 4H), 1.32-1.15 (m, 3H), 1.15 (s, 3H), 1.13 (q, J=7.2 Hz, 2H), 0.92-0.82 (m, 1H), 0.78 (t, J=7.2 Hz, 3H), 0.61 (s, 3H).

Example 16. Preparation of Compound 13 from Compound 12

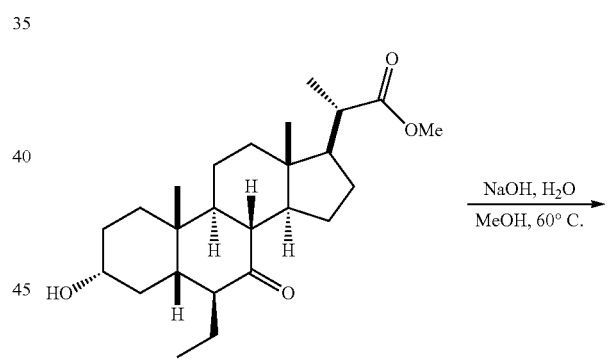

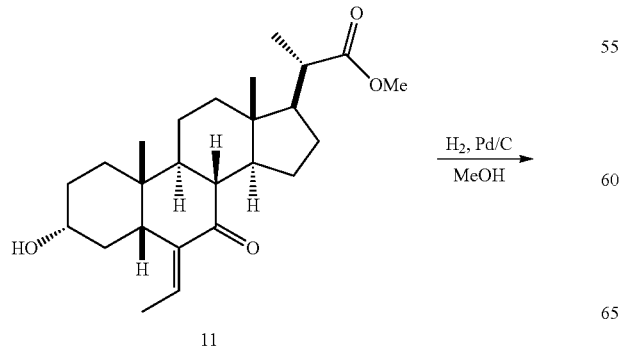

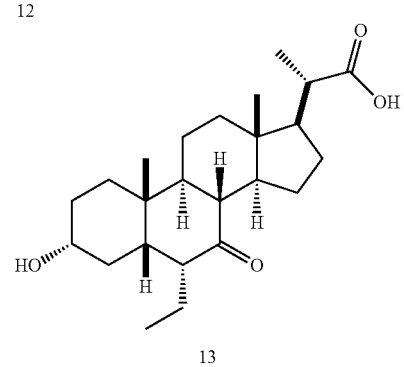

To a solution of crude compound 12 (8.0 g, 19.8 mmol, 1.0 eq) in MeOH (99 mL, 12.3 v) and H$_2$O (24.7 mL, 3.1 v) was charged 50% ageous NaOH (7.9 mL, 98.9 mmol, 5.0 eq) and the reaction was stirred at 60° C. for 24 hrs. The reaction was cooled to 0° C. and made acidic (pH ~1-2) with 1M HCl. The aqueous mixture was extracted with EtOAc (3×200 mL). The combined organic layers were dried (MgSO₄), filtered, and concentrated to give crude compound 13 (7.5 g, HPLC purity: 98.0%) as a pale yellow amorphous solid. This material was used in the next step without further purification. $^1$H NMR (400 MHz, Chloroform-d) δ 3.45-3.36 (m, 1H), 2.55 (q, J=6.2 Hz, 1H), 2.34-2.16 (m, 1H), 2.14-2.05 (m, 1H), 1.85-1.52 (m, 8H), 1.36 (dddt, J=23.7, 9.8, 5.5, 3.3 Hz, 3H), 1.29-1.18 (m, 1H), 1.17-1.06 (m, 9H), 1.06-0.91 (m, 2H), 0.90-0.72 (m, 2H), 0.66 (t, J=7.4 Hz, 3H), 0.54 (s, 3H).

Example 17. Preparation of Compound (V) from Compound 13

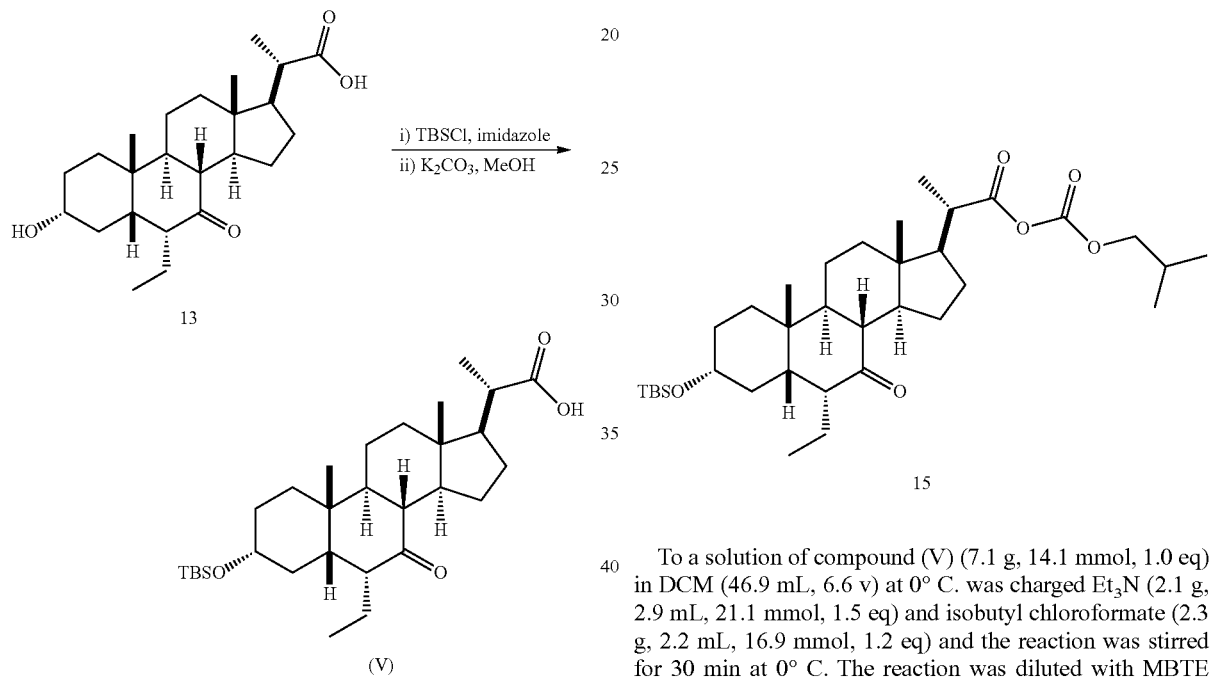

To a solution of crude compound 13 (7.7 g, 19.8 mmol, 1.0 eq) in THF (65.9 mL, 8.5 v) and DMF (16.5 mL, 2.1 v) at 0° C. was charged imidazole (8.1 g, 119 mmol, 6.0 eq) and TBSCl (6.6 g, 43.5 mmol, 2.2 eq). The ice bath was removed, and the reaction was stirred at room temperature for 18 hrs. Methanol (16.5 mL, 2.1 v) and K₂CO₃ (1.4 g, 9.9 mmol, 0.5 eq) were added and the reaction was stirred for 2 hrs. The reaction was carefully acidified with 10% aqueous citric acid (200 mL) and diluted with EtOAc (200 mL). The layers were separated and the aqueous layer was extracted with EtOAc (2×200 mL). The combined organic layers were washed with H₂O (3×100 mL) and brine (100 mL), then dried (MgSO₄), filtered, and concentrated to give a yellow solid. This solid was recrystallized from CH₂Cl₁₂/hexanes to give compound (V) (7.1 g, 71% yield over 5 steps HPLC purity: 98.2%). $^1$H NMR (500 MHz, Chloroform-d) δ 9.78 (bs, 1H), 3.50-3.43 (m, 1H), 2.63 (q, J=6.3 Hz, 1H), 2.41-2.34 (m, 1H), 2.26-2.19 (m, 1H), 1.91-1.82 (m, 3H), 1.81-1.65 (m, 3H), 1.64-1.27 (m, 8H), 1.25-1.16 (7H), 1.14-1.07 (m, 2H), 1.01-0.86 (m, 3H), 0.83 (s, 9H), 0.78 (t, J=7.4 Hz, 3H), 0.65 (s, 3H), −0.00 (s, 6H).

Example 18. Preparation of Compound 15 from Compound (V)

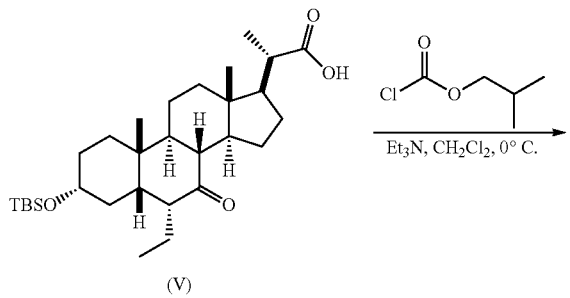

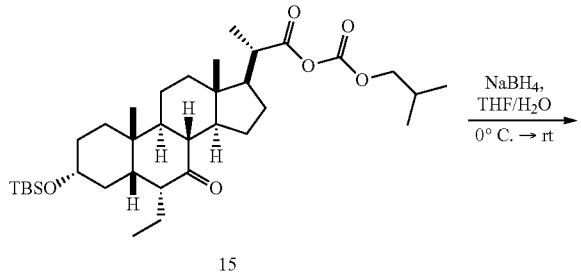

To a solution of compound (V) (7.1 g, 14.1 mmol, 1.0 eq) in DCM (46.9 mL, 6.6 v) at 0° C. was charged Et₃N (2.1 g, 2.9 mL, 21.1 mmol, 1.5 eq) and isobutyl chloroformate (2.3 g, 2.2 mL, 16.9 mmol, 1.2 eq) and the reaction was stirred for 30 min at 0° C. The reaction was diluted with MBTE (150 mL) and washed with water (2×100 mL), brine (100 mL), dried (MgSO₄) and concentrated to give crude compound 15 (9.0 g, HPLC purity: 99.1%) as an orange amorphous solid. The crude sample was used directly in the next step without further purification.

Example 19. Preparation of Compound (VI) from Compound 15

-continued

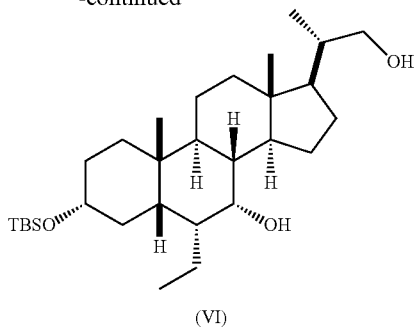

(VI)

To a solution of crude compound 15 (8.5 g, 14.1 mmol, 1.0 eq) in THF (47 mL, 5.5 v) and H₂O (23 mL, 2.7 v) at 0° C. was charged NaBH₄ (1.1 g, 28.1 mmol, 2.0 eq) and the reaction was stirred for 30 min at 0° C. NaBH₄ (1.1 g, 28.1 mmol, 2.0 eq) was added and the reaction was stirred overnight, warming slowly to rt. The reaction was cooled to 0° C., diluted with EtOAc (85 mL) and quenched carefully with 10% citric acid (85 mL). The layers were separated and the aqueous layer was extracted with EtOAc (2×40 mL). The combined organic layers were dried (MgSO₄), filtered, and concentrated to give crude compound (VI) (6.9 g, HPLC purity: 95.8%) as a pale yellow amorphous solid. ¹H NMR (400 MHz, Chloroform-d) δ 3.71-3.52 (m, 2H), 3.44-3.20 (m, 2H), 1.91 (dt, J=12.3, 2.9 Hz, 1H), 1.76 (dtd, J=20.6, 10.0, 4.5 Hz, 4H), 1.62 (ddp, J=9.8, 6.8, 3.8, 3.0 Hz, 2H), 1.58-1.27 (m, 8H), 1.27-1.05 (m, 5H), 1.00 (d, J=6.6 Hz, 2H), 0.94 (dd, J=14.3, 3.6 Hz, 1H), 0.90-0.85 (m, 4H), 0.84 (s, 9H), 0.63 (s, 3H), −0.00 (s, 6H).

Example 20. Preparation of Compound 18b from Compound (VIb)

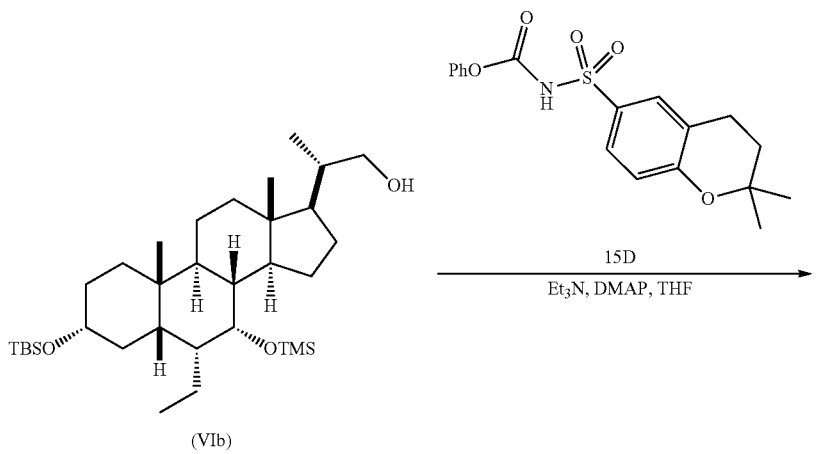

(VIb)

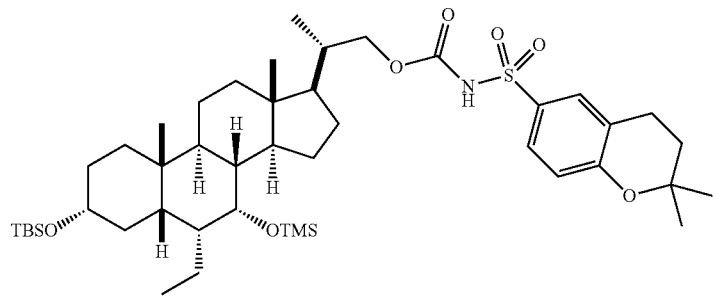

18b

To a stirred solution of (VIb) (22.33 g, 39.5 mmol) and 15D (20 g, 55.3 mmol) in THF (180 mL) at RT was added TEA (8.26 ml, 59.3 mmol), followed by DMAP (0.966 g, 7.91 mmol). The resulting mixture was heated to 50° C. and stirred for 2 h at 50° C., cooled down to RT, quenched with 3% citric acid, and extracted with EtOAc. The combined organic layers were washed with brine and concentrated in vacuo, and the residue was purified by chromatography on silica gel using hexane/EtOAc (100/0 to 70/30, 15 min) to give a product as a white foam. 32.2 g of compound 18b. $^1$H NMR (500 MHz, Chloroform-d) δ 7.71-7.61 (m, 2H), 7.19-7.16 (m, 1H), 6.83-6.72 (m, 1H), 4.06 (dd, J=10.3, 3.4 Hz, 1H), 3.65 (dd, J=10.5, 8.1 Hz, 1H), 3.56 (s, 1H), 3.26 (dt, J=10.9, 6.7 Hz, 1H), 2.75 (t, J=6.7 Hz, 2H), 1.88-1.70 (m, 5H), 1.74-1.46 (m, 4H), 1.46-1.36 (m, 4H), 1.35-1.13 (m, 12H), 1.09 (m, 4H), 0.99-0.91 (m, 2H), 0.95-0.76 (m, 9H), 0.92-0.74 (m, 21H), 0.81 (s, 9H), 0.54 (s, 3H), 0.00 (s, 9H), −0.03 (s, 6H).

Example 21. Preparation of Compound (VIII) from Compound 18b

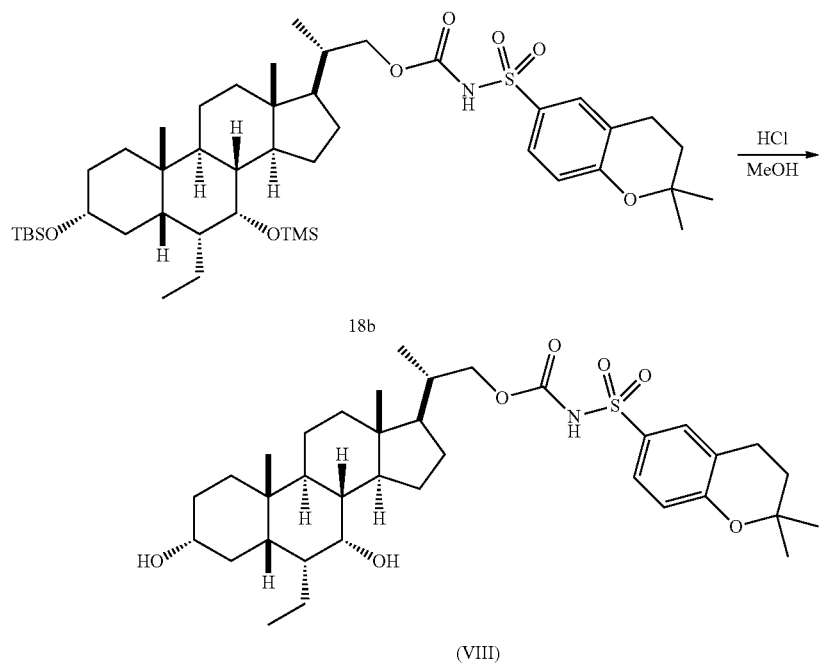

To a stirred solution of 18b (32 g, 38.4 mmol) in MeOH (180 ml) at RT was added HCl (0.316 ml, 3.84 mmol). The mixture was stirred at RT for 1 h, and then quenched with 0.6 ml of 6N NaOH and concentrated in vacuo. The residue was purified by chromatography on silics gel using hexane/acetone (100/0 to 50/50, 20 min) to give compound (VIII) as a white solid (21 g, 85%). LC-MS (m/z, ES$^-$): 644.36 [M−1]. $^1$H NMR (400 MHz, Chloroform-d) δ 7.71-7.55 (m, 3H), 6.79 (d, J=8.7 Hz, 1H), 4.04 (dd, J=10.4, 3.3 Hz, 1H), 3.76-3.57 (m, 2H), 3.34 (tt, J=10.5, 5.1 Hz, 1H), 2.75 (t, J=6.7 Hz, 2H), 1.88-1.70 (m, 5H), 1.74-1.46 (m, 4H), 1.46-1.36 (m, 4H), 1.35-1.13 (m, 12H), 1.09 (m, 4H), 0.99-0.91 (m, 2H), 0.95-0.76 (m, 9H), 0.57 (s, 3H).

Example 22. Synthesis of 20A

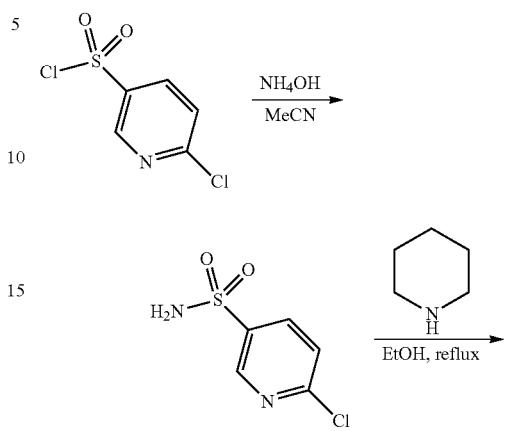

-continued

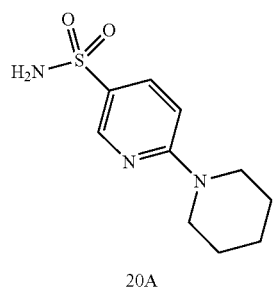

20A

A solution of 6-chloropyridine-3-sulfonyl chloride (50 g) in MeCN (75 ml) was added dropwise to aq NH$_4$OH (28-30%, 125 ml) at 0° C. (ice bath) (exthothermic). After addition, the ice bath was removed and the reaction mixture was stirred for another 45 min, and then cooled down to 0° C. again, quenched with water and acidified with 37% HCl (120 ml) to pH 1-2. The mixture was extracted with EtOAc, and the combined organic layers were washed with brine, dried over $Na_2SO_4$, filtered, and concentrated. The crude product (40 g) was dried overnight under high vacuum and used directly for the next step.

The crude product, 6-chloropyridine-3-sulfonamide (79 g), was first suspended in EtOH (560 ml), and then piperidine (85 ml) was added slowly. The resulting mixture was refluxed for 22 h, cooled down to rt, and the precipitated solids (after 3 h aging) were collected by filtration and rinsed with EtOH, and dried. The solids were further purified by mixing with water, filtration, and washing with water, and then dried to give compound 20A as a white solid (94 g, 95% yield). $^1$H NMR (400 MHz, DMSO-$d_6$) δ 8.42 (d, J=2.5 Hz, 1H), 7.79 (dd, J=9.2, 2.6 Hz, 1H), 7.15 (s, 2H), 6.91 (d, J=9.1 Hz, 1H), 3.64 (dd, J=6.5, 4.4 Hz, 4H), 1.64 (qd, J=6.2, 5.8, 3.4 Hz, 2H), 1.53 (tq, J=7.9, 4.8, 4.1 Hz, 4H).

Example 23. Preparation of Compound 20D from 20A

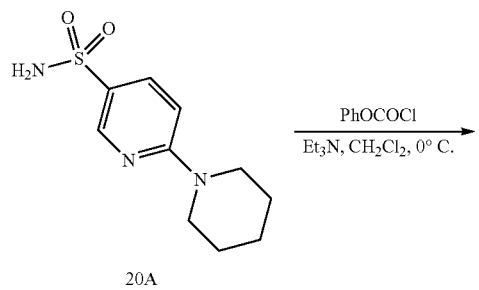

20A

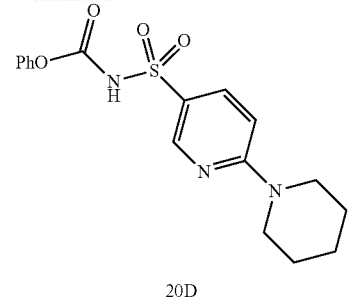

20D

Phenyl chloroformate (24.95 ml, 199 mmol) was added dropwise to a suspension of 20A (40 g, 166 mmol) and TEA (69.3 ml, 497 mmol) in DCM (400 ml) at 0° C. The suspension slowly became clear during the addition of phenyl chloroformate (about half way) then cloudy again. The reaction mixture was stirred at 0° C. for 2 h, then diluted with DCM (700 mL), washed with water (2×700 mL) and 10% citric acid (2×400 ml), the organic layer was separated quickly (precipitation formed quickly after second wash with 10% citric acid) and the formed solids (after 30 min aging) were filtered off and rinsed with DCM, and dried to give 29 g of compound 20D. The filtrate was concentrated to 200 mL and the solids were filtered and rinsed with DCM, and dried to afford another 19 g of compound 20D (48 g in total, 80% yield). $^1$H NMR (400 MHz, Chloroform-d) δ 8.71 (dd, J=2.6, 0.7 Hz, 1H), 7.96 (dd, J=9.3, 2.6 Hz, 1H), 7.66 (s, 1H), 7.40-7.30 (m, 2H), 7.27-7.18 (m, 1H), 7.13-7.05 (m, 2H), 6.58 (dd, J=9.4, 0.7 Hz, 1H), 3.70 (t, J=5.4 Hz, 4H), 1.77-1.59 (m, 6H).

Example 24. Preparation of Compound 19b from Compound (VIb)

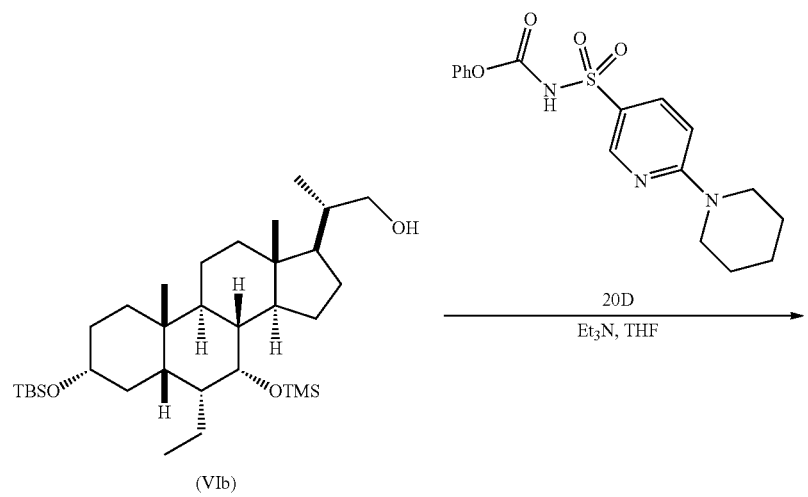

(VIb)

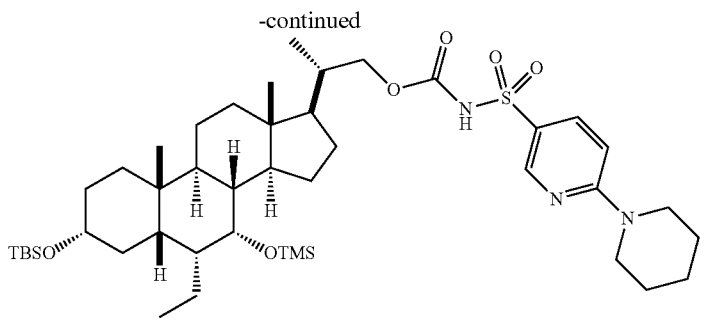

19b

To a solution of 20D (22.83 g, 63.2 mmol) in THF (354 mL) at rt was added compound (VIb) (34 g, 60.2 mmol), triethylamine (25.2 ml, 181 mmol), and DMAP (0.735 g, 6.02 mmol). The resulting slurry was heated to 50° C. and stirred for 4 hrs (the mixture was almost clear), then cooled down to rt, and diluted with EtOAc (1000 mL). The mixture was washed with 3% citric acid and brine, dried over $Na_2SO_4$, and concentrated. The residue was purified by chromatography on silica gel using hexane/acetone (100/0 to 65/35, 25 min) to give compound 19b (49 g, ~93% yield) as a white foam containing a small amount of phenol (side product). $^1$H NMR (400 MHz, Chloroform-d) δ 8.62 (d, J=2.5 Hz, 1H), 7.99-7.94 (m, 1H), 7.19-7.14 (m, 1H), 6.62 (d, J=9.4 Hz, 1H), 4.08 (dd, J=10.4, 3.6 Hz, 1H), 3.69 (s, 3H), 3.73-3.61 (m, 1H), 3.56 (d, J=2.6 Hz, 1H), 3.51 (s, 1H), 3.27 (td, J=10.8, 5.3 Hz, 1H), 1.94-1.58 (m, 12H), 1.54-1.45 (m, 2H), 1.44 (s, 1H), 1.38 (s, 1H), 1.39-1.25 (m, 2H), 1.28-1.11 (m, 3H), 1.14-0.93 (m, 3H), 0.97-0.84 (m, 4H), 0.79 (d, J=10.3 Hz, 16H), 0.78-0.74 (m, 6H), 0.57 (d, J=11.6 Hz, 1H), 0.55 (s, 2H), 0.00 (s, 9H), −0.03 (s, 6H).

Example 25. Preparation of Compound (IX) from Compound 19b

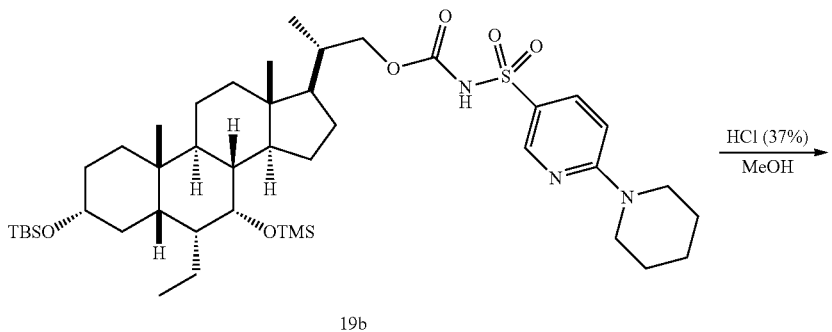

19b

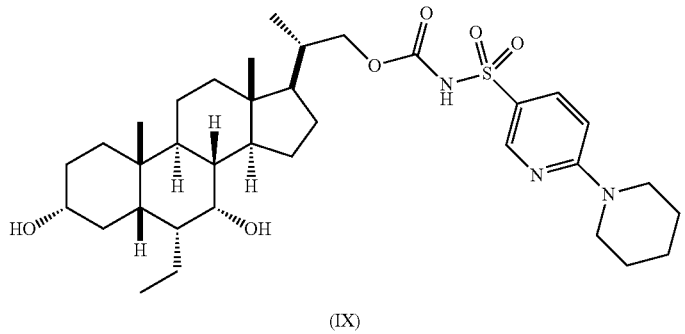

(IX)

To a solution of 19b (49 g, 58.9 mmol) in MeOH (294 ml) at rt was added HCl (37%) (1.450 ml, 17.66 mmol). The resulting mixture was stirred for 3 h, then neutralized with sodium hydroxide (50%) (0.933 ml, 17.66 mmol) in 2 ml of water, and concentrated. The residue was purified by chromatography on silica gel using hexane/acetone (100/0 to 50/50, 15 min) to give a product as a white foam, which was chased 3 times with ethanol to remove the residual acetone. The resulting white foam was lyophilized for 7 days to afford compound (IX) (32 g, 84%). LC-MS (m/z, ES$^+$): 646.39 [M+1]. $^1$H NMR (400 MHz, DMSO-d$_6$) δ 11.70 (s, 1H), 8.46 (d, J=2.6 Hz, 1H), 7.78 (dd, J=9.3, 2.7 Hz, 1H), 6.93 (d, J=9.3 Hz, 1H), 4.33 (d, J=18.4 Hz, 1H), 4.05 (d, J=5.1 Hz, 1H), 3.98 (dd, J=10.6, 3.4 Hz, 1H), 3.74 (dd, J=10.6, 7.0 Hz, 1H), 3.68 (t, J=5.5 Hz, 4H), 3.52-3.41 (m, 2H), 3.14 (s, 1H), 1.89-1.74 (m, 2H), 1.74-1.60 (m, 6H), 1.61-1.51 (m, 6H), 1.44 (td, J=14.7, 8.4 Hz, 4H), 1.41-1.25 (m, 2H), 1.28-1.00 (m, 7H), 1.02-0.88 (m, 2H), 0.92-0.79 (m, 9H), 0.59 (s, 3H).

While this invention has been particularly shown and described with references to preferred embodiments thereof, it will be understood by those skilled in the art that various changes in form and details may be made therein without departing from the scope of the invention encompassed by the appended claims.

What is claimed:

1. A process for preparing a compound of Formula (II):

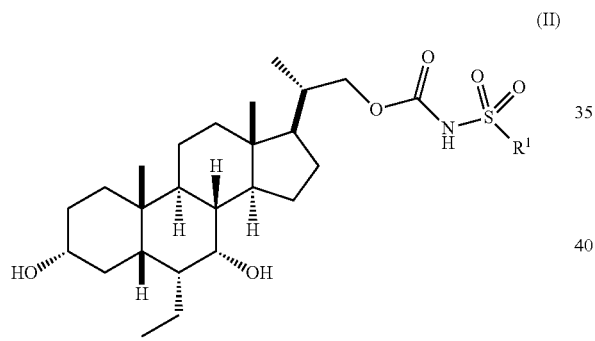

wherein
R$^1$ is selected from the group consisting of:
1) substituted or unsubstituted —C$_1$-C$_8$ alkyl;
2) substituted or unsubstituted —C$_2$-C$_8$ alkenyl;
3) substituted or unsubstituted —C$_2$-C$_8$ alkynyl;
4) substituted or unsubstituted —C$_3$-C$_8$ cycloalkyl;
5) substituted or unsubstituted aryl;
6) substituted or unsubstituted arylalkyl;
7) substituted or unsubstituted 3- to 12-membered heterocycloalkyl;
8) substituted or unsubstituted heteroaryl;
9) substituted or unsubstituted heteroarylalkyl; and
10) NR$_a$R$_b$, wherein, R$_a$ and R$_b$ are each independently selected from hydrogen, substituted or unsubstituted —C$_1$-C$_8$ alkyl, substituted or unsubstituted —C$_2$-C$_8$ alkenyl, substituted or unsubstituted —C$_2$-C$_8$ alkynyl, substituted or unsubstituted —C$_3$-C$_8$ cycloalkyl; alternatively R$_a$ and R$_b$ are taken together with the nitrogen atom to which they are attached to form a 3- to 12-membered hetercyclic ring;

said process comprising the steps of:
(1ai) reacting compound 1,

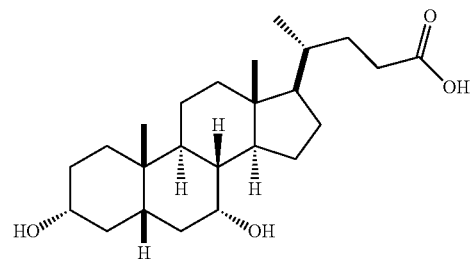

with a C$_1$-C$_6$-alkanol under acid catalysis to produce compound 2,

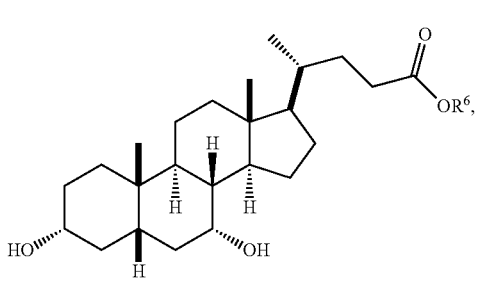

wherein R$^6$ is C$_1$-C$_6$-alkyl;
(1aii) reacting compound 2 with a strong base in the presence of a hydroxyl protecting agent to produce a compound of Formula 2a,

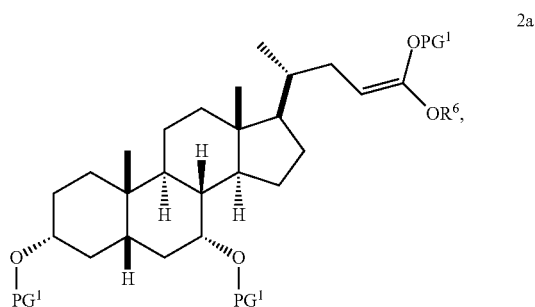

and reacting the compound of Formula 2a with a halogenating agent to produce compound 3,

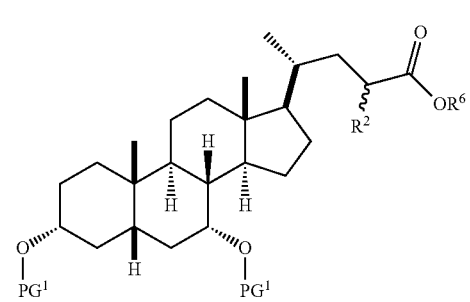

wherein
PG$^1$ is a hydroxyl protecting group; and
R$^2$ is selected from Br, I, and C$_1$;

(1aiii) reacting compound 3 with an organic base to eliminate HR$^2$ and produce compound 4,

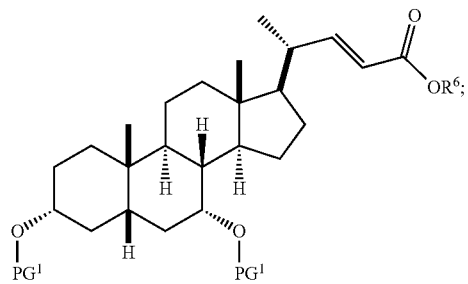

(1aiv) deprotecting compound 4 to produce compound 5,

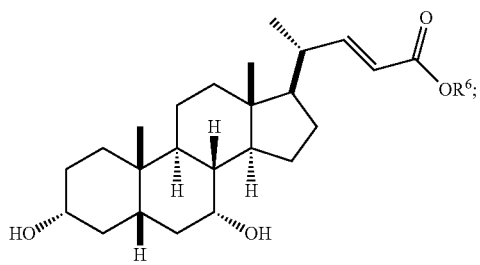

(1av) reacting compound 5 with a hydroxyl protecting agent to produce compound 6:

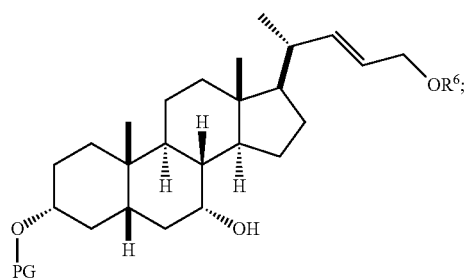

(1avi) oxidatively cleaving and oxidizing compound 6 in the presence of a base to produce a compound of Formula (III):

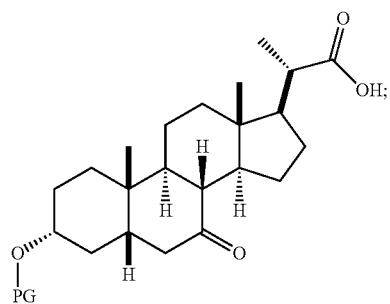

(2bi) reacting the compound of Formula (III) with a C$_1$-C$_6$-alkanol under acid catalysis to produce compound 8,

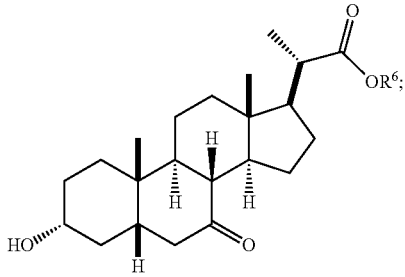

(2bii) reacting compound 8 with a silylating agent in the presence of a base to produce compound 9:

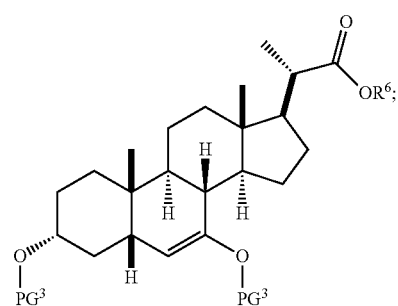

wherein PG$^3$ is a silyl group;

(2biii) reacting compound 9 with acetaldehyde in the presence of a Lewis acid to produce compound 10:

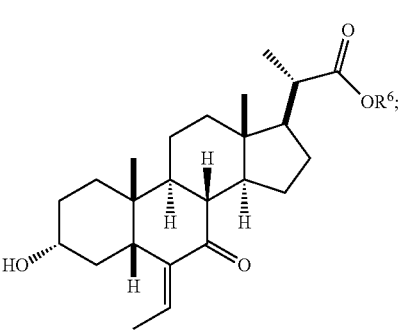

(2biv) hydrogenating compound 10 to produce compound 11:

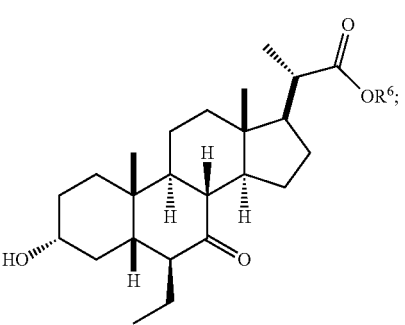

(2bv) reacting compound 11 with a base in a protic solvent or a mixture of a protic solvent and a non-protic solvent to produce compound 12:

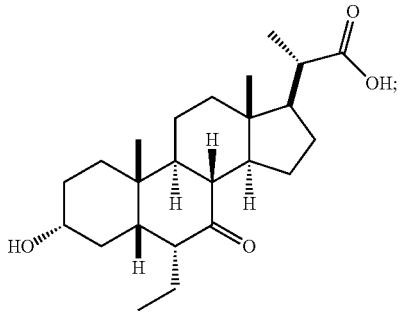

2b(vi) reacting compound 12 with a hydroxyl protecting agent to produce the compound of Formula (V),

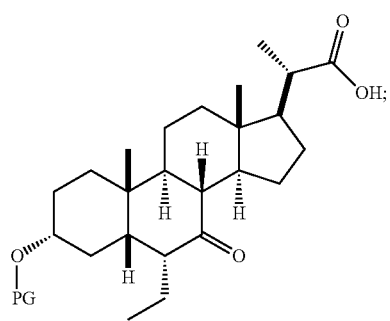

(3bi) reacting the compound of Formula (V) with a compound of the formula R³OC(O)Cl to produce compound 13:

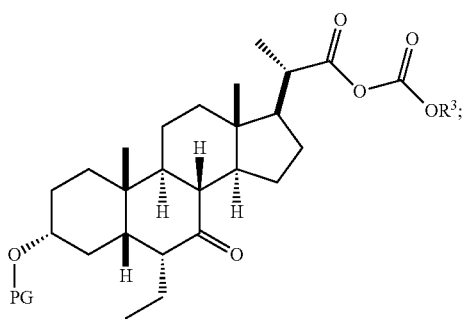

wherein R³ is an alkyl group; and
(3bii) reducing compound 13 to produce the compound of Formula (VI),

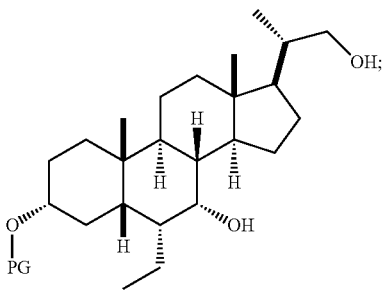

(4bi) reacting the compound of Formula (VI) with a compound of Formula 15E,

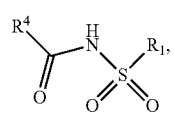

wherein R⁴ is imidazol-1-yl, alkyl-O, aryl-O, Cl, or —CCl₃, in the presence of an organic base, to produce compound 17,

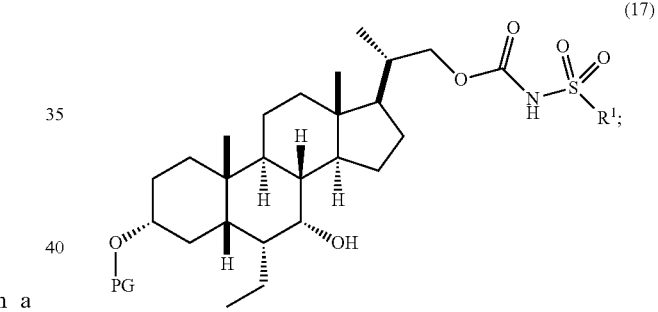

and
(4bii) deprotecting the compound of Formula 17 to produce the compound of Formula (II).
2. The process of claim 1, wherein R₁ is

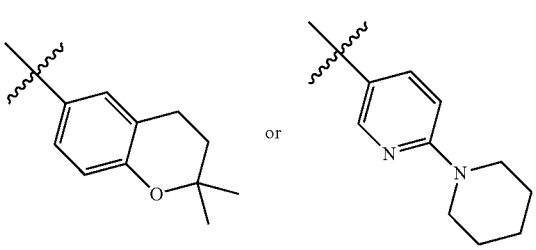

3. The process of claim 1, wherein step (4bii) is conducted in an aprotic solvent at a temperature from about 0° C. to about 80° C.
4. The process of claim 1, wherein the compound of Formula 15E is selected from compounds 15B, 15C and 15D:

15B
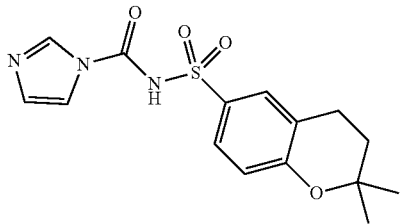
15C
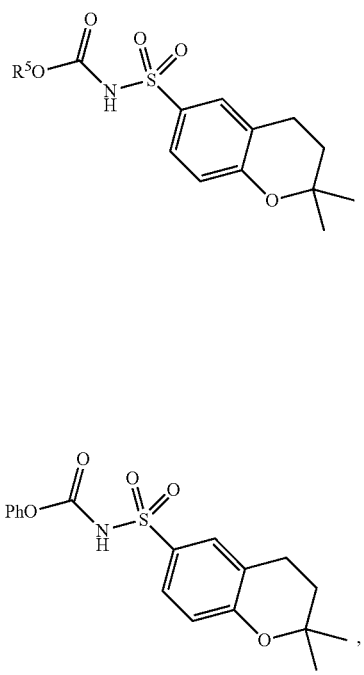
15D
wherein R⁵ is alkyl or aryl.
5. The process of claim 1, wherein the compound of Formula 15E is selected from compounds 20B, 20C and 20D:
20B
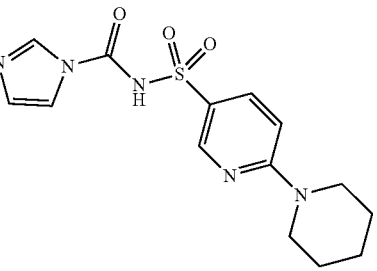
20C
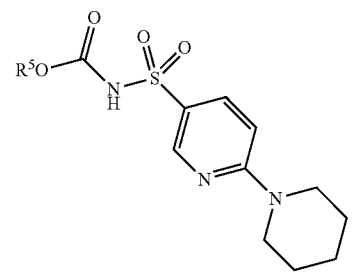
20D
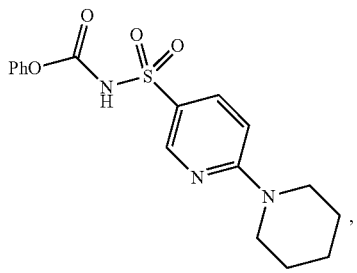
wherein $R^5$ is alkyl or aryl.
6. The process of claim 1 wherein PG is TBS.
7. The process of claim 1 wherein $R^6$ is methyl.
8. The process according to claim 1 wherein $R^6$ is methyl and $PG^1$ is TBS.
* * * * *

UNITED STATES PATENT AND TRADEMARK OFFICE
CERTIFICATE OF CORRECTION

PATENT NO. : 10,676,500 B2
APPLICATION NO. : 15/948370
DATED : June 9, 2020
INVENTOR(S) : Guoqiang Wang et al.

Page 1 of 1

It is certified that error appears in the above-identified patent and that said Letters Patent is hereby corrected as shown below:

<u>At Column 79</u>
In Claim 1, at Line 3, after and delete "$C_1$" and insert -- Cl --.

Signed and Sealed this
Tenth Day of November, 2020

Andrei Iancu
*Director of the United States Patent and Trademark Office*